US009505779B2

(12) United States Patent
Yoon et al.

(10) Patent No.: US 9,505,779 B2
(45) Date of Patent: Nov. 29, 2016

(54) TACROLIMUS ANALOGUES, A NEUROPROTECTIVE COMPOSITION COMPRISING THE SAME, AN IMMUNOSUPPRESSIVE COMPOSITION COMPRISING THE SAME, A METHOD FOR PREPARING THE SAME, AND A MUTANT FOR PRODUCING THE SAME

(71) Applicant: EWHA University—Industry Collaboration Foundation, Seoul (KR)

(72) Inventors: Yeo Joon Yoon, Seoul (KR); Jae Jong Kim, Daejeon (KR); Si Kyu Lim, Daegu (KR)

(73) Assignee: Intron Biotechnology, Inc., Seongnam-Si, Gyeonggi-Do (KR)

( * ) Notice: Subject to any disclaimer, the term of this patent is extended or adjusted under 35 U.S.C. 154(b) by 29 days.

(21) Appl. No.: 13/774,899

(22) Filed: Feb. 22, 2013

(65) Prior Publication Data
US 2013/0230559 A1  Sep. 5, 2013

Related U.S. Application Data

(63) Continuation-in-part of application No. PCT/KR2011/003644, filed on May 17, 2011.

(30) Foreign Application Priority Data

Aug. 24, 2010 (KR) .................. 10-2010-0082059
Apr. 7, 2011 (KR) .................. 10-2011-0032278

(51) Int. Cl.
| C07D 491/12 | (2006.01) |
| C12N 9/10 | (2006.01) |
| A61K 31/00 | (2006.01) |
| C07D 493/16 | (2006.01) |
| C12P 17/18 | (2006.01) |
| C07D 498/18 | (2006.01) |
| C12N 15/52 | (2006.01) |

(52) U.S. Cl.
CPC ........... *C07D 493/16* (2013.01); *C07D 498/18* (2013.01); *C12N 9/1029* (2013.01); *C12N 15/52* (2013.01); *C12P 17/188* (2013.01); *Y02P 20/52* (2015.11)

(58) Field of Classification Search
None
See application file for complete search history.

(56) References Cited

U.S. PATENT DOCUMENTS

| 4,894,366 | A | 1/1990 | Okuhara et al. |
| 5,116,756 | A | 5/1992 | Dumont et al. |
| 7,704,725 | B2 * | 4/2010 | Kulkarni et al. ........ 435/252.35 |
| 2007/0142424 | A1 | 6/2007 | Vaid |
| 2007/0191415 | A1 | 8/2007 | Kumar et al. |
| 2008/0160586 | A1 | 7/2008 | Cabri et al. |
| 2008/0286842 | A1 | 11/2008 | Kulkarni et al. |

FOREIGN PATENT DOCUMENTS

| EP | 1751272 | 12/2008 | |
| KR | 1004858770000 | 4/2005 | |
| WO | WO2005063963 | 7/2005 | |
| WO | WO 2010106366 A1 * | 9/2010 | |
| WO | WO 2011021036 A1 * | 2/2011 | ........... C07D 498/18 |
| WO | WO2012/026665 | 3/2012 | |

OTHER PUBLICATIONS

Mo et al. 2010 (Biosynthesis of the Allylmalonyl-CoA Extender Unit for the FK506 Polyketide Synthase Proceeds through a Dedicated Polyketide Synthase and Facilitates the Mutasynthesis of Analogues; JACS 133:976-985).*
Goranovic et al. 2010 (Origin of the Allyl Group in FK506 Biosynthesis; Journal of Biological Chemistry, 285:14292-14300; published online Mar. 1, 2010).*
Andexer et al. 2011 (Biosynthesis of the immunosuppressants FK506, FK520, and rapamycin involves a previously undescribed family of enzymes acting on chorismate; PNAS Early Edition 10.1073/1015773108; Feb. 8, 2011; pp. 1-6).*
Estaquio et al. 2010 (Engineering Fluorometabolite Production: Fluorinase Expression in Salinispora tropica Yields Fluorosalinosporamide; J. Nat. Prod. 73:378-382).*
Eustaquio et al. 2010 (Engineering Fluorometabolite Production: Fluorinase Expression in Salinispora tropica Yields Fluorosalinosporamide; J. Nat. Prod. 73:378-382).*
Box, S. J. et al., "27-O-Demethyhapamycin, an Immunosuppressant Compound Produced by a New Strain of Streptomyces Hygroscopicus", The Journal of Antibiotics (1995) vol. 48, No. 11, pp. 1347-1349.
Kim, H. S. et al., "Isolation and identification of a novel microorganism producing the immunosuppressant tacrolimus", Journal of Bioscience and Bioengineering (2008) vol. 105, No. 4, pp. 418-421.
Liu, Y. et al., "Biosynthesis of Salinosporamides from α,β-Unsaturated Fatty Acids: Implications for Extending Polyketide Synthase Diversity" J.Am. Chem. Soc. 2009, 131, 10376.
Motamedi et al., "Structural Organization of a Multifunctional Polyketide Synthase Involved in the Biosynthesis of the Macrolide Immunosuppressant FK506", Eur. J. Biochem. 244, 74-80, 1997.
Muramatsu, H. et al., "Phylogenetic analysis of immunosuppressant FK506-producing streptomyces strains", Actinomycetologica (2005) vol. 19, pp. 33-39.

(Continued)

*Primary Examiner* — Gary Nickol
*Assistant Examiner* — Mary Lyons
(74) *Attorney, Agent, or Firm* — McNees Wallace & Nurick LLC

(57) ABSTRACT

The present invention relates to novel tacrolimus analogs, a composition for the prevention or treatment of neurological diseases or immune hypersensitivity disorders comprising the same, a method for preventing or treating neurological diseases or immune hypersensitivity disorders comprising administering the analogs to a subject, a method for preparing the analogs using an isolated modified *Streptomyces* sp. strain wherein the activity of one or more enzymes selected from the group consisting of TcsA, TcsB, TcsC and TcsD is reduced; and the isolated modified *Streptomyces* sp. strain for prepare the analogs.

12 Claims, 32 Drawing Sheets

(56) References Cited

OTHER PUBLICATIONS

PCT/KR2011/003644 IPRP and Written Opinion dated Feb. 26, 2013.
PCT/KR2011/003644 ISR dated Jan. 6, 2012.
Rosen, M.K., Standaert, et al , "Inhibition of FKBP Rotamase Activity by Immunosuppressant FK506, Twisted Amide Surrogate", Science 1990, vol. 248, pp. 863.
Shafiee, A. et al., "Chemical and Biological Characterization of Two FK506 Analogs Produced by Targeted Gene Disruption in *Sreptomyces* sp. MA6548", The Journal of Antibiotics (1997) vol. 50, No. 5, pp. 418-423.
Wu et al., "The FK520 gene cluster of *Streptomyces hygroscopicus* var. *ascomyceticus* (ATCC 14891) contains genes for biosynthesis of unusual polyketide extender units" Gene, vol. 251, pp. 81-90, 2000.

* cited by examiner

36-Methyl-FK506

| Position | $\delta_C$ | $\delta_H$ | COSY correlations | HMBC correlations |
|---|---|---|---|---|
| 1 | 169.08 | - | | |
| 2 | 56.62 | 4.61 | H-3b | C-1, 3, 4 |
| 3 | 27.56 | 2.08 | H-3b | |
| | | 1.94 | H-4b | |
| 4 | 21.06 | 1.75 | H-4b | C-3, 6 |
| | | 1.39 | | |
| 5 | 24.47 | 1.75 | H-5b | C-3, 6 |
| | | 1.47 | H-4b | |
| 6 | 39.30 | 4.43 | H-5a/b, H-6b | C-2, 4, 5, 8 |
| | | 3.03 | H-5a/b | C-2, 8 |
| 7 | - | - | | |
| 8 | 164.70 | - | | |
| 9 | 196.14 | - | | |
| 10 | 97.19 | - | | |
| 11 | 34.60 | 2.19 | H-12b, 38 | |
| 12 | 32.68 | 2.14 | | C-13 |
| | | 1.47 | | C-11, 13 |
| 13 | 73.57 | 3.40 | H-12a/b | |
| 14 | 72.85 | 3.68 | H-13, 15 | C-10, 12, 13, 15 |
| 15 | 75.21 | 3.58 | H-16a/b | |
| 16 | 33.15 | 1.53 | H-16b | |
| | | 1.07 | | |
| 17 | 26.00 | 1.68 | H-16a/b, 39 | C-19 |
| 18 | 48.66 | 2.14 | H-17, 18b | C-16, 17, 19, 20, 39, 40 |
| | | 1.80 | | C-16, 17, 19, 20, 39, 40 |
| 19 | 138.82 | - | | |
| 20 | 122.86 | 5.02 | H-21 | C-18, 21, 35, 40 |
| 21 | 51.61 | 3.55 | H-35a/b | C-19, 20, 22, 35, 36 |
| 22 | 212.42 | - | | |
| 23 | 43.69 | 2.78 | H-23b | C-22, 24, 25 |
| | | 2.16 | | C-21, 22 |
| 24 | 69.89 | 3.95 | H-23a/b, 25 | C-26 |
| 25 | 39.77 | 1.89 | H-41 | C-24, 41 |
| 26 | 77.68 | 5.33 | H-25 | C-24, 25, 27, 28, 41, 42 |

Fig. 15A

| Position | $\delta_C$ | $\delta_H$ | COSY correlations | HMBC correlations |
|---|---|---|---|---|
| 27 | 132.19 | - | | |
| 28 | 129.90 | 5.10 | H-29 | C-26, 29, 30, 34, 42 |
| 29 | 34.89 | 2.31 | H-30b, 34a | |
| 30 | 34.82 | 2.02 | | C-28, 31 |
|  |  | 0.96 | | C-28, 29, 31, 32, 34 |
| 31 | 84.17 | 3.02 | H-30a/b | C-32, 45 |
| 32 | 73.69 | 3.42 | H-31, 33b | C-31, 33 |
| 33 | 31.20 | 2.02 | H-33b, 34a | |
|  |  | 1.37 | H-34b | C-32 |
| 34 | 30.63 | 1.64 | | C-28, 29, 30 |
|  |  | 1.08 | | |
| 35 | 38.98 | 2.50 | | C-36methyl, 20, 21, 22, 36, 37 |
|  |  | 2.09 | | C-36methyl, 20, 21, 22, 36, 37 |
| 36 | 143.00 | - | | |
| 37 | 112.06 | 4.76 | | C-36 |
|  |  | 4.66 | | |
| 38 | 16.24 | 1.00 | | C-10, 12 |
| 39 | 20.37 | 0.93 | | C-16, 17, 18 |
| 40 | 15.94 | 1.61 | | C-18, 19, 20 |
| 41 | 9.45 | 0.88 | | C-24, 25, 26 |
| 42 | 14.13 | 1.64 | | C-26, 27, 28 |
| 43 | 56.31 | 3.42 | | C-13 |
| 44 | 57.06 | 3.31 | | C-15 |
| 45 | 56.58 | 3.42 | | C-31 |
| 36-methyl | 22.77 | 1.72 | | C-36 |

Fig. 15B

36-Fluoro-FK520

| Position | $\delta_C$ | $\delta_H$ | COSY correlations | HMBC correlations |
|---|---|---|---|---|
| 1 | 168.84 | - | - | |
| 2 | 56.61 | 4.65 | H-3a/b | C-1, 3, 4, 6, 8 |
| 3 | 27.71 | 2.09 | H-2, 3b, 4a | |
| | | 1.98 | H-2, 4a/b | C-1, 2 |
| 4 | 21.15 | 1.75 | H-3a, 4b, 5b | C-2, 3, 6 |
| | | 1.40 | H-3a/b, 4a, 5a/b | |
| 5 | 24.55 | 1.75 | H-4b, 5b, 6a/b | C-3, 6 |
| | | 1.47 | H-4a, 5a, 6a/b | |
| 6 | 39.29 | 4.45 | H-5a/b | C-2, 8, 4, 5 |
| | | 3.02 | H-5a/b | C-2, 8 |
| 7 | - | - | | |
| 8 | 164.45 | - | | |
| 9 | 195.88 | - | | |
| 10 | 97.04 | - | | |
| 11 | 34.63 | 2.16 | H-12b | C-10 |
| 12 | 32.60 | 2.16 | | C-13 |
| | | 1.50 | | C-11, 13 |
| 13 | 73.55 | 3.41 | H-12a/b | |
| 14 | 72.65 | 3.75 | H-13, 15 | C-10, 12, 13, 15 |
| 15 | 75.12 | 3.62 | H-16a/b | C-16 |
| 16 | 33.02 | 1.63 | H-16b | C-14 |
| | | 1.10 | | C-14, 15, 17 |
| 17 | 25.98 | 1.79 | | C-16, 19, 38 |
| 18 | 48.23 | 2.16 | H-17 | C-17, 19 |
| | | 1.81 | | C-16, 17, 19, 20, 39, 38 |
| 19 | 139.77 | - | | |
| 20 | 121.23 | 5.10 | H-21 | C-18, 21, 22, 35, 39 |
| 21 | 48.40 | 3.58 | H-20, 35 | C-19, 20, 22, 35, 36 |

Fig. 23A

| Position | $\delta_C$ | $\delta_H$ | COSY correlations | HMBC correlations |
|---|---|---|---|---|
| 22 | 212.91 | - | | |
| 23 | 43.02 | 2.86 | H-23b, 24 | C-22, 24, 25 |
|  |  | 2.08 | H-23a, 24 | C-22, 24 |
| 24 | 70.19 | 3.91 | H-23a/b, 25 | C-26 |
| 25 | 39.94 | 1.90 | H-24, 26 | C-24, 40 |
| 26 | 76.67 | 5.34 | H-25 | C-24, 25, 27, 28, 40, 41 |
| 27 | 132.44 | - | | |
| 28 | 129.48 | 5.10 | H-29 | C-26, 27, 29, 30, 34, 41 |
| 29 | 34.87 | 2.29 | H-30a/b, 34a/b | |
| 30 | 34.84 | 2.04 | H-29, 31 | |
|  |  | 0.97 | H-29, 30a, 31 | C-28, 29, 31, 32, 34 |
| 31 | 84.15 | 3.02 | H-30a/b, 32 | C-32, 44 |
| 32 | 73.51 | 3.41 | H-31, 33a/b | C-31 |
| 33 | 31.18 | 2.00 | H-32, 33b, 34a | |
|  |  | 1.38 | H-32, 33a, 34a/b | C-29, 32, 34 |
| 34 | 30.62 | 1.64 | H-29, 33a/b, 34b | C-28, 29, 30 |
|  |  | 1.06 | H-29, 33a/b | |
| 35 | 31.05 | 2.25 | H-36 | C-20, 21, 22, 36 |
| 36 | 81.57 | 4.42 | H-35 | C-21 |
| 37 | 16.28 | 1.01 | H-11 | C-10, 11, 12 |
| 38 | 20.45 | 0.95 | H-17 | C-16, 17, 18 |
| 39 | 15.95 | 1.60 | | C-18, 19, 20 |
| 40 | 9.56 | 0.87 | H-25 | C-24, 25, 26 |
| 41 | 14.20 | 1.65 | | C-26, 27, 28 |
| 42 | 56.27 | 3.40 | | C-13 |
| 43 | 56.61 | 3.32 | | C-15 |
| 44 | 56.60 | 3.42 | | C-31 |

Fig. 23B

| Com-pound | $\Delta G_{elec}$ | $\Delta G_{vdw}$ | $\Delta G_{nonpol,sol}$ | $\Delta G_{elec,sol}$ | $-T\Delta S$ | $\Delta G_{bind}$ |
|---|---|---|---|---|---|---|
| 1 | -11.83±0.12 | -25.08±0.09 | -2.93±0.01 | 21.53±0.09 | 12.61±0.41 | -6.42±0.05 |
| 2 | -14.36±0.13 | -23.53±0.10 | -3.03±0.01 | 23.13±0.06 | 11.76±0.56 | -6.03±0.05 |
| 33 | -12.20±0.12 | -25.45±0.09 | -2.90±0.01 | 20.40±0.08 | 12.37±0.54 | -7.78±0.04 |
| 34 | -11.75±0.07 | -24.78±0.09 | -3.05±0.01 | 21.45±0.08 | 12.31±0.56 | -5.82±0.09 |

Fig. 24

SEQUENCE LISTING

<160> NUMBER OF SEQ ID NOS: 48

<210> SEQ ID NO 1
<211> LENGTH: 2391
<212> TYPE: DNA
<213> ORGANISM: Streptomyces sp.

<400> SEQUENCE: 1

```
gtgatctccc gtgctccgga cggggagggg ccgcacgacg acagggtcgc cgtcgtcggg      60
atgggtgtcg ccgtgccggg cgcctgcgac ccggaggagc tgtggaagct gctgtgcggt     120
gacagacccg tgttcgatga gccgtcggac cgcttccggc tcgattcctt ctggtccgcg     180
gatccggccg ccgaggaccg cggctatgtc cgcacttcgg gttttctgca cgacttccgt     240
ccgcaccccg cactggccgc ggagatcgcg gccggaacgc tctcggccgc cgcgcagaac     300
ccggtctggc tgcggcactg cctgctgcag gcgcgggaca ccgtcaccgc ccgcagcacc     360
gaccgatacg cctaccacgt cgggaccagc gccctggtcg gccagcgcac cgacgaggcg     420
gtgctggccg agtgcgttcc ccgggccgtc gccgagcggc tgcaccgcga cgagcccgcc     480
cggatggccg aggccgaggc acggctgcgc gccctgctga gaagccacca cgggtacggc     540
gccgaagagc cgcgggacac actgcccgac cgggtcgtac gggccgcggc ggccggactg     600
ttacccgacg actgcgagtt ctccgtggtc gacgcggcct gctcgtcctc gctgtacgcg     660
atcggtctgg gtgtcgcgag cctgctggcg ggcgcctgcg atatcgccta ctgcggcggg     720
gtgtcgggag tgacgccgcg ttacaacgtc acgttctcca aactgcacgg gctgagcccc     780
agcggcgacg tccgcgcgtt cgacgacgac gccgacggaa cgctgttctc ggacggagcg     840
ggcgttgtcg cgctgaagcg cctggaccgg gccgtcgagg acggggaccc ggtgttcggc     900
gtcctcgtgg gattcggcgg gtcgtcggac ggccgggaa cggcgatcta cgcccccaac     960
cccgtcggtc agcgccgctg cctggaccgc gcccggcagg catcgggtct cacggcggac    1020
gatgtcgact gggtcatcgc gcacgggacg ggcacggccg tcgtgacgc ggtcgagctg    1080 cggaccctcg ccgccgccac cgatccgggc agcgtctggt gcggatccaa caagtccctg    1140
ctcggtcata ccgggtggag ctccggagtg gtctcggtcg tccaggccct cacggcgctg    1200
cggcagggca cgataccggc acagcgacgc ttcaccggtc ccgggctcac cgcgcagacc    1260
ggcgaccggg tacgcatacc ttcggcggac gttccctggc atgcgggcgg ccggcgttcc    1320
aggaccgcag gcgtctccgc cttcggcttc ggcggcacca acgccatct gctgatcacc    1380
```

```
gaccgagagc cgtgcggac gggcccgcgc ccgcccgca ccgggcccga tccggtggtc    1440
gtcctcgcct ggaccgcgca cctgcccggc gaccccggcc cgaggcgac ggagcggctg    1500 ctgcgcgaag gccgcatccc cgggccgcgt accttcggcc cccgctatcc ggcgccccg    1560 tttccggacg tccgtctccc tccgccacc gtacggtcca cggacgcggg ccagctcatg    1620
gccctgcggg tggcgggcct gttcgccgcc gaacacggtg agctgtgggc gccggtacgg    1680
gcgaccaccg gggtcttcgc ggccgccacc ggtccgccgc cgtcctccat ggatcatctg    1740
gtgcgctgtc atgccgccga cgtacaccgc attctcgacg aacccgaccg gacggcgttc    1800
accgaatggc tcgccgacct gcgggccacg accccggcga ccaccaagga cacgctgccg    1860
gggctgctgc ccaacatcat cccggcgcgt atcgccaacc gctacgacct gggcggcccc    1920
accatgctgg tcgacacggg caccaccagc gggctcaccg ccgtgcacac cgccgtccgc    1980
caactggcgg ccggtgccgt cgacatggcg ctcgtcctcg gtgtcagcgc gaccggccga    2040
cccgagttcg cccgcttcat gggcgtcgcg gccgagcgga tcgcggaggg ggcgttcctc    2100
ctcgcgctga gtcgcgagtc cgtcgccctc gcgcacggcc tgaccccct cgtccgcctc    2160 cgcacggact ggaccggcag ccctcaggcg tctgcggatg ccgtcccgg cgggccggt    2220 gcggcggagg acaccttcct cggcgccgac ggcgtcctcg ccgtgatccg tgccctgcac    2280
tccaccgcgt ccggcgtcac cgtgggaccc gcggacggcg aaccgggccc ggtgatcacc    2340
ctctcccccg ccgacggctc acctcttcgg cagacaagga ccagccgatg a    2391
```

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
gacaagctta tgctggcggt gaaggcg                                       27

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
ccgtctagac cagaaggaat cgagccggaa                                    30

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
cagtctagag tgatccgtgc cctgcactcc                                    30

<210> SEQ ID NO 5
<211> LENGTH: 28
<212> TYPE: DNA
<213> ORGANISM: Artificial
<220> FEATURE:
<223> OTHER INFORMATION: primer

<400> SEQUENCE: 5

-continued gccgaattcg atgacgatgt ccgggtcg                                          28

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
tttaagcttc cgtcggatcg gggcggcag                                         29

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
aaaggatccg aagaggaacg ccaccccac                                         29

<210> SEQ ID NO 8
<211> LENGTH: 29
<212> TYPE: DNA
<213> ORGANISM: Artificial
<220> FEATURE:
<223> OTHER INFORMATION: primer

<400> SEQUENCE: 8
tttagatctt gatccggtcg tgatctccc                                         29

<210> SEQ ID NO 9
<211> LENGTH: 27
<212> TYPE: DNA
<213> ORGANISM: Artificial
<220> FEATURE:
<223> OTHER INFORMATION: primer

<400> SEQUENCE: 9
aaagaattcg tcgccgggca ggtgcgc                                           27

<210> SEQ ID NO 10
<211> LENGTH: 29
<212> TYPE: DNA
<213> ORGANISM: Artificial
<220> FEATURE:
<223> OTHER INFORMATION: primer

<400> SEQUENCE: 10
tttaagctta acaagtccct gctcggtca                                         29

<210> SEQ ID NO 11
<211> LENGTH: 29
<212> TYPE: DNA
<213> ORGANISM: Artificial
<220> FEATURE:
<223> OTHER INFORMATION: primer

<400> SEQUENCE: 11
aacggatccg tcttcgacgg ggctcccgg                                         29

<210> SEQ ID NO 12
<211> LENGTH: 29
<212> TYPE: DNA

```
<213> ORGANISM: Artificial
<220> FEATURE:
<223> OTHER INFORMATION: primer

<400> SEQUENCE: 12
aaaagatctt cccgggtcta cccctcga                                      29

<210> SEQ ID NO 13
<211> LENGTH: 28
<212> TYPE: DNA
<213> ORGANISM: Artificial
<220> FEATURE:
<223> OTHER INFORMATION: primer

<400> SEQUENCE: 13
tttgaattcc tcacccaggc cctgacgc                                      28

<210> SEQ ID NO 14
<211> LENGTH: 28
<212> TYPE: DNA
<213> ORGANISM: Artificial
<220> FEATURE:
<223> OTHER INFORMATION: primer

<400> SEQUENCE: 14
gctaagcttc tcaggcgtct gcggatgc                                      28

<210> SEQ ID NO 15
<211> LENGTH: 28
<212> TYPE: DNA
<213> ORGANISM: Artificial
<220> FEATURE:
<223> OTHER INFORMATION: primer

<400> SEQUENCE: 15
atcggatcct tcgctcaccg gggctgcc                                      28

<210> SEQ ID NO 16
<211> LENGTH: 28
<212> TYPE: DNA
<213> ORGANISM: Artificial
<220> FEATURE:
<223> OTHER INFORMATION: primer

<400> SEQUENCE: 16
agcagatctg gcatgttctg gtcagtcc                                      28

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
gtcgaattcc atgccacgaa cgggtcga                                      28

<210> SEQ ID NO 18
<211> LENGTH: 28
<212> TYPE: DNA
<213> ORGANISM: Artificial
<220> FEATURE:
<223> OTHER INFORMATION: primer

<400> SEQUENCE: 18
tataagctta ctcgtcgcac gcggcagc                                      28
```

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
atatctagac tcacccaggc cctgacgc                                       28

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
atatctagac cagtgatgcg aaggcatg                                       28

<210> SEQ ID NO 21
<211> LENGTH: 28
<212> TYPE: DNA
<213> ORGANISM: Artificial
<220> FEATURE:
<223> OTHER INFORMATION: primer

<400> SEQUENCE: 21
gacgaattcc aggaggttga cggtggtt                                       28

<210> SEQ ID NO 22
<211> LENGTH: 27
<212> TYPE: DNA
<213> ORGANISM: Artificial
<220> FEATURE:
<223> OTHER INFORMATION: primer

<400> SEQUENCE: 22
attaagcttg ggcgaactcc tcgttcg                                        27

<210> SEQ ID NO 23
<211> LENGTH: 27
<212> TYPE: DNA
<213> ORGANISM: Artificial
<220> FEATURE:
<223> OTHER INFORMATION: primer

<400> SEQUENCE: 23
atttttggat cccgcacgag tctcggg                                        27

<210> SEQ ID NO 24
<211> LENGTH: 27
<212> TYPE: DNA
<213> ORGANISM: Artificial
<220> FEATURE:
<223> OTHER INFORMATION: primer

<400> SEQUENCE: 24
gacggatcct ctgaatcgga gattcgt                                        27

<210> SEQ ID NO 25
<211> LENGTH: 27
<212> TYPE: DNA
<213> ORGANISM: Artificial
<220> FEATURE:

<223> OTHER INFORMATION: primer

<400> SEQUENCE: 25
ttagaattcg tggccgttgg agatgaa                                      27

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
agcaagctta gtcctctgag gagctggtag                                   30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
tcgagatctc acgaggtctc cttggagaca                                   30

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28
aaaggatccg tcatcatcga cccgtag                                      27

<210> SEQ ID NO 29
<211> LENGTH: 27
<212> TYPE: DNA
<213> ORGANISM: Artificial
<220> FEATURE:
<223> OTHER INFORMATION: primer

<400> SEQUENCE: 29
tttgaattct ccttgctggt ctggacg                                      27

<210> SEQ ID NO 30
<211> LENGTH: 28
<212> TYPE: DNA
<213> ORGANISM: Artificial
<220> FEATURE:
<223> OTHER INFORMATION: primer

<400> SEQUENCE: 30
tttaagcttc ggcgtggagg cgtggtcg                                     28

<210> SEQ ID NO 31
<211> LENGTH: 28
<212> TYPE: DNA
<213> ORGANISM: Artificial
<220> FEATURE:
<223> OTHER INFORMATION: primer

<400> SEQUENCE: 31
aaaggatccc gtgaggccct cggcgaca                                     28

```
<210> SEQ ID NO 32
<211> LENGTH: 28
<212> TYPE: DNA
<213> ORGANISM: Artificial
<220> FEATURE:
<223> OTHER INFORMATION: primer

<400> SEQUENCE: 32
aaaggatccg acgaggtgga ctcccacg                                              28

<210> SEQ ID NO 33
<211> LENGTH: 28
<212> TYPE: DNA
<213> ORGANISM: Artificial
<220> FEATURE:
<223> OTHER INFORMATION: primer

<400> SEQUENCE: 33
tttgaattcc cagcaccctg tcgtcccg                                              28

<210> SEQ ID NO 34
<211> LENGTH: 28
<212> TYPE: DNA
<213> ORGANISM: Artificial
<220> FEATURE:
<223> OTHER INFORMATION: primer

<400> SEQUENCE: 34
ccgaagctta cagcacgggg atactctg                                              28

<210> SEQ ID NO 35
<211> LENGTH: 28
<212> TYPE: DNA
<213> ORGANISM: Artificial
<220> FEATURE:
<223> OTHER INFORMATION: primer

<400> SEQUENCE: 35
ggatctagac agccgttcgg cgatcgcg                                              28

<210> SEQ ID NO 36
<211> LENGTH: 28
<212> TYPE: DNA
<213> ORGANISM: Artificial
<220> FEATURE:
<223> OTHER INFORMATION: primer

<400> SEQUENCE: 36
aaatctagaa tgcgctgacg cggccccg                                              28

<210> SEQ ID NO 37
<211> LENGTH: 28
<212> TYPE: DNA
<213> ORGANISM: Artificial
<220> FEATURE:
<223> OTHER INFORMATION: primer

<400> SEQUENCE: 37
tttggatcca cggtcgactc acgccgcc                                              28

<210> SEQ ID NO 38
<211> LENGTH: 30
<212> TYPE: DNA
<213> ORGANISM: Artificial
<220> FEATURE:
<223> OTHER INFORMATION: primer
```

```
<400> SEQUENCE: 38
gttaccaagc ttgtaccgag gaccacgtac                                              30

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
gaatccggat ccgaccgttt tgtcctgttc                                              30

<210> SEQ ID NO 40
<211> LENGTH: 30
<212> TYPE: DNA
<213> ORGANISM: Artificial
<220> FEATURE:
<223> OTHER INFORMATION: primer

<400> SEQUENCE: 40
tttaccggat tcttcaccgg ctccaccgat                                              30

<210> SEQ ID NO 41
<211> LENGTH: 32
<212> TYPE: DNA
<213> ORGANISM: Artificial
<220> FEATURE:
<223> OTHER INFORMATION: primer

<400> SEQUENCE: 41
gggtcctcta aagagagtg tcgaggagat cg                                            32

<210> SEQ ID NO 42
<211> LENGTH: 796
<212> TYPE: PRT
<213> ORGANISM: Streptomyces sp.

<400> SEQUENCE: 42
```

Met Ile Ser Arg Ala Pro Asp Gly Glu Gly Pro His Asp Asp Arg Val
1               5                   10                  15

Ala Val Val Gly Met Gly Val Ala Val Pro Gly Ala Cys Asp Pro Glu
            20                  25                  30

Glu Leu Trp Lys Leu Leu Cys Gly Asp Arg Pro Val Phe Asp Glu Pro
        35                  40                  45

Ser Asp Arg Phe Arg Leu Asp Ser Phe Trp Ser Ala Asp Pro Ala Ala
    50                  55                  60

Glu Asp Arg Gly Tyr Val Arg Thr Ser Gly Phe Leu His Asp Phe Arg
65                  70                  75                  80

Pro His Pro Ala Leu Ala Ala Glu Ile Ala Ala Gly Thr Leu Ser Ala
                85                  90                  95

Ala Ala Gln Asn Pro Val Trp Leu Arg His Cys Leu Leu Gln Ala Arg
            100                 105                 110

Asp Thr Val Thr Ala Arg Ser Thr Asp Arg Tyr Ala Tyr His Val Gly
        115                 120                 125

Thr Ser Ala Leu Val Gly Gln Arg Thr Asp Glu Ala Val Leu Ala Glu
    130                 135                 140

Cys Val Pro Arg Ala Val Ala Glu Arg Leu His Arg Asp Glu Pro Ala
145                 150                 155                 160

Arg Met Ala Glu Ala Glu Ala Arg Leu Arg Ala Leu Leu Arg Ser His

```
                165                 170                 175
His Gly Tyr Gly Ala Glu Glu Pro Arg Asp Thr Leu Pro Asp Arg Val
            180                 185                 190

Val Arg Ala Ala Ala Gly Leu Leu Pro Asp Asp Cys Glu Phe Ser
            195                 200                 205

Val Val Asp Ala Ala Cys Ser Ser Leu Tyr Ala Ile Gly Leu Gly
        210                 215                 220

Val Ala Ser Leu Leu Ala Gly Ala Cys Asp Ile Ala Tyr Cys Gly Gly
225                 230                 235                 240

Val Ser Gly Val Thr Pro Arg Tyr Asn Val Thr Phe Ser Lys Leu His
                245                 250                 255

Gly Leu Ser Pro Ser Gly Asp Val Arg Ala Phe Asp Asp Ala Asp
            260                 265                 270

Gly Thr Leu Phe Ser Asp Gly Ala Gly Val Val Ala Leu Lys Arg Leu
            275                 280                 285

Asp Arg Ala Val Glu Asp Gly Asp Pro Val Phe Gly Val Leu Val Gly
        290                 295                 300

Phe Gly Gly Ser Ser Asp Gly Arg Gly Thr Ala Ile Tyr Ala Pro Asn
305                 310                 315                 320

Pro Val Gly Gln Arg Arg Cys Leu Asp Arg Ala Arg Gln Ala Ser Gly
                325                 330                 335

Leu Thr Ala Asp Asp Val Asp Trp Val Ile Ala His Gly Thr Gly Thr
            340                 345                 350

Ala Val Gly Asp Ala Val Glu Leu Arg Thr Leu Ala Ala Ala Thr Asp
        355                 360                 365

Pro Gly Ser Val Trp Cys Gly Ser Asn Lys Ser Leu Leu Gly His Thr
    370                 375                 380

Gly Trp Ser Ser Gly Val Val Ser Val Val Gln Ala Leu Thr Ala Leu
385                 390                 395                 400

Arg Gln Gly Thr Ile Pro Ala Gln Arg Phe Thr Gly Pro Gly Leu
                405                 410                 415

Thr Ala Gln Thr Gly Asp Arg Val Arg Ile Pro Ser Ala Asp Val Pro
            420                 425                 430

Trp His Ala Gly Gly Arg Arg Ser Arg Thr Ala Gly Val Ser Ala Phe
        435                 440                 445

Gly Phe Gly Gly Thr Asn Ala His Leu Leu Ile Thr Asp Arg Glu Pro
    450                 455                 460

Val Arg Thr Gly Pro Arg Pro Ala Arg Thr Gly Pro Asp Pro Val Val
465                 470                 475                 480

Val Leu Ala Trp Thr Ala His Leu Pro Gly Asp Pro Gly Pro Glu Ala
                485                 490                 495

Thr Glu Arg Leu Leu Arg Glu Gly Arg Ile Pro Gly Pro Arg Thr Phe
            500                 505                 510

Gly Pro Arg Tyr Pro Ala Pro Pro Phe Pro Asp Val Arg Leu Pro Pro
        515                 520                 525

Pro Thr Val Arg Ser Thr Asp Ala Gly Gln Leu Met Ala Leu Arg Val
    530                 535                 540

Ala Gly Leu Phe Ala Ala Glu His Gly Glu Leu Trp Ala Pro Val Arg
545                 550                 555                 560

Ala Thr Thr Gly Val Phe Ala Ala Ala Thr Gly Pro Pro Ser Ser
                565                 570                 575

Met Asp His Leu Val Arg Cys His Ala Ala Asp Val His Arg Ile Leu
            580                 585                 590
```

Asp Glu Pro Asp Arg Thr Ala Phe Thr Glu Trp Leu Ala Asp Leu Arg
            595                 600                 605

Ala Thr Thr Pro Ala Thr Thr Lys Asp Thr Leu Pro Gly Leu Leu Pro
        610                 615                 620

Asn Ile Ile Pro Ala Arg Ile Ala Asn Arg Tyr Asp Leu Gly Gly Pro
625                 630                 635                 640

Thr Met Leu Val Asp Thr Gly Thr Thr Ser Gly Leu Thr Ala Val His
            645                 650                 655

Thr Ala Val Arg Gln Leu Ala Ala Gly Ala Val Asp Met Ala Leu Val
            660                 665                 670

Leu Gly Val Ser Ala Thr Gly Arg Pro Glu Phe Ala Arg Phe Met Gly
            675                 680                 685

Val Ala Ala Glu Arg Ile Ala Glu Gly Ala Phe Leu Leu Ala Leu Ser
        690                 695                 700

Arg Glu Ser Val Ala Leu Ala His Gly Leu Thr Pro Leu Val Arg Leu
705                 710                 715                 720

Arg Thr Asp Trp Thr Gly Ser Pro Gln Ala Ser Ala Asp Ala Val Pro
            725                 730                 735

Gly Gly Pro Gly Ala Ala Glu Asp Thr Phe Leu Gly Ala Asp Gly Val
            740                 745                 750

Leu Ala Val Ile Arg Ala Leu His Ser Thr Ala Ser Gly Val Thr Val
        755                 760                 765

Gly Pro Ala Asp Gly Glu Pro Gly Pro Val Ile Thr Leu Ser Pro Ala
            770                 775                 780

Asp Gly Ser Pro Leu Arg Gln Thr Arg Thr Ser Arg
785                 790                 795

<210> SEQ ID NO 43
<211> LENGTH: 1284
<212> TYPE: DNA
<213> ORGANISM: Streptomyces sp.

<400> SEQUENCE: 43
gtggcgttcc tcttccccgg ccaagggtcg tacgtaccgg gcgtcttcgc cggtctgggt    60
gccgatgccg gcgggtggc gaccctcgtc gcggagatcg acgcggccgt cgaggagttc   120
cggctgaagc cggtccggcc gcttctgttc tccccggacg ctccggcgct ggcggagctg   180
ctcgaatccg atcacgagcg gctcgacgtg gccatcctgg caacctccat cgccctggcg   240
gagcttctgg agtcacggca cgggatgagt cccgaccatg tcgccgggca cagtctcggg   300
gagttcggag ccctcgccgt cgccggtgtc ttcaccccgg gcgacgcggc cagggcggtc   360
tgcgaacgcc acgccacgct cgcaaggcg ccgccgccca cgggcgggat gctggcggtg   420
aaggcggacg cggcccgcgc cggggagctg atcgctgccg cgcgggccgg gacgtcggcc   480
gtatcggcgc tgaactcccc cagccagacg gtgatcagcg gcgcggaagc ggatctggtg   540
aaggtgcagc agctggcacg ggaggaaggc atccgtacct cccggctgca tgtccccggc   600
cccttccacg tcccgcagct ggccgacgcg agcgccctgt acgcgacgac gatgcgcacc   660
atacggatat ccgcgccccg ggagcgcttc ttctactccc acggtctggg ccgcttcctg   720
acggcgcagg acgatgtcgt cgacctgatg gtgaacgaca tgacccgtcc ggtgcggttc   780
cacgactccg tacgcgcgct gaacgcggag ggcgtcacga cctatgtgga gtgcggtgcg   840
ctggacgtcc tcacccggat cgtgtccgga tcgctgcccc gcgccgtgac cctggcaccg   900 ctccggagg ccacgacgac accggatctg tccgcccggc tgcggccccgc cggcacccg   960

```
gccgtgaacg gcgtcgctgc gcccgcgggc ccggcgccgg ccgccgaggt cgacccggag   1020
gtgctcgcgg gggtacgtgc ggtgtgcgcc gaggtcctgg agtatccgct ggaggtgatc   1080
accgacgacg cggacttcca ggccgatctc ggtgtcgact ccctggcgat gaccgagctg   1140
caggcccacg cgctgcagcg gttcggtctg aaggagacgc tgcaggacgc ggatacggga   1200
acgtacggca cggtttccgg tctggccgcg tacatcacgg gcctgctgag tgagggcacc   1260
ggttccgttt ccgggcggcg gtga                                          1284

<210> SEQ ID NO 44
<211> LENGTH: 1338
<212> TYPE: DNA
<213> ORGANISM: Streptomyces sp.

<400> SEQUENCE: 44
atgacccacg ttcgcgacgc cgcggccacc gacgacccgc aggccatcgc cgcctgcgag     60 gtccccggccg gctaccgggc cgccgttgtc ctcgcggccg accaccaggc actcgccggg    120
agccccgtcg aagaccggga cccccgcaag acggtccagg tccaggaggt ccccaccccc    180
gaaccggacc acgcgaggt gctcatcgcc accatggcga gctccatcaa ctacaacacc     240
gtgtggtcgg cgctcttcga gcccgttccc accttccgct ttctgcgcac cctcggccgt    300
acctcaccgg aggcggcccg ccacgaccag ccgtaccacg tgctcggctc cgacctgtcc    360
ggagtggtgc tgcgcaccgg accgggtgta cgggagtgga agcccggcga cgaagtcgtc    420
gcgcactgtc tgcaaccgga cctgcagacg ccgggcgggc acgacgacac cctgctcgac    480
cccggccagc gggtctgggg ctacgagacg aacttcggcg gcctcgccga actctccctg    540
gtcaaggcga accagctgat gccgaagccc gcccatctca cctggaggag gcggcctcc    600 ctggggtgg cgctctccac ggcctaccgt cagctggtgt cccaccacgg ggcggcgatg    660
aagcagggcg agcgcgtcct ggtctggggt gccgccggtg gcgtcggcgc ctacgcgacc    720
cagctggccc tcaacggcgg cgccgttccg atctgtgtgg tgtcgtcgca ggccaaggcc    780
gacctgtgcc ggcagatggg cgcggagctc gtcatcgacc gtgctgcgga gggcttctcg    840
ttctgggagg ggcgggaccg cccgcggctg agcgagtgga gccgcttccg cggtgccgtc    900
cggtccctgg cgggtgacga cccggacatc gtcatcgagc accccggccg ggacaccttc    960
ggcgtcagcg tcatgatcgc cgcccggggc ggaaaggtgg tcacctgcgc atcgaccacc   1020
ggctaccagc acacctacga caaccgccat ctgtggatgc gcgtcaaacg catcatcggg   1080
tcacatatgg cgaactaccg ggaagcctgg gccgcgaacg aactcgtcgc acgcggcagc   1140
atccaccccg tgctctcccg ggtctacccc ctcgacgcca caggcgacgc cacgcacgcc   1200
gtcgccaaca acagccacca cggcaaggtg ggcgtgctct gcctcgccga ccgcccggc   1260 atgggagtgc gcgaccccga gctgcggcc cggaaactcg acagcatcaa cctgttccgg   1320 aagggcagc cccggtga                                                  1338

<210> SEQ ID NO 45
<211> LENGTH: 1161
<212> TYPE: DNA
<213> ORGANISM: Streptomyces sp.

<400> SEQUENCE: 45
gtgagcgaat ccgaacgcct cggtatcgtc agggatttcg tcgcccggga gatcctgggc     60
cgcgaaggca tcctcgactc gctggcggac gcaccactgg ccctgtacga acgcttcgcc    120
```

```
gagacgggcc tgatgaactg gtgggtcccc aaggagcacg gcggtcttgg gctcggcctg      180
gaagagagtg tgcggatcgt ctccgaactc gcctacgggg acgccggggt ggcgttcacc      240
ctgtttctgc ccgtcctgac gaccagcatg atcggctggt acggcagcga ggagctcaag      300
gagagattcc tcggccctct cgtggcccgg cggggcttct cgccacgct gggcagcgag       360 cacgaggccg gcagcgaact ggcccggatc tccaccacgg tccgccgtga cggcgacacg      420
ctggtactcg acggcaccaa ggccttctcc accagcaccg acttcgcccg gttcctcgtc      480
gtcatcgccc gttcggcgga cgacccggcc cggtacacgg cggtcaccgt accgcgggac      540
gcgccggggc tgcgggtcga caaacgctgg gacgtcatcg ggatgcgcgc tccgcgacc       600 tatcaggtgt cgttctccga ctgccgggtg ccggggggaca acgcgctgaa cggcaatggg     660
ctgcggctgc tggagatcgg cctcaacgcc agcagaatcc tgatcgccgc atccgctctg      720
ggtgtcgccc gcaggatccg cgatgtgtgc atggagtacg ggaagacgaa gtcgctcaag      780
ggcgctccgc tcgtcaagga cggcgtgttc gccgggcggc tcggccagtt cgagatgcag      840
atcgacgtga tggcgaacca gtgcctggcg ccgcacgggg cctacgacgc gaccgcggcc      900 cggccccgacg ccgccagggt gctgctgcgg cagggcgccc agaagtcggc actgaccgcg    960
aagatgttct gcgggcagac ggcctggcag atcgcgtcca ccgcgtcgga gatgttcggc     1020
ggcatcgggt acacgcacga catggtgatc gggaagctgc tgcgggatgt gcggcacgct     1080
tcgatcatcg agggcggcga cgacgtcctg cgcgatctcg tctaccagcg cttcgtcgtc     1140
cccaccgcga aacgtaccta g                                              1161
```

<210> SEQ ID NO 46
<211> LENGTH: 427
<212> TYPE: PRT
<213> ORGANISM: Streptomyces sp.

<400> SEQUENCE: 46

```
Met Ala Phe Leu Phe Pro Gly Gln Gly Ser Tyr Val Pro Gly Val Phe
1               5                   10                  15

Ala Gly Leu Gly Ala Asp Ala Gly Arg Val Ala Thr Leu Val Ala Glu
            20                  25                  30

Ile Asp Ala Ala Val Glu Glu Phe Arg Leu Lys Pro Val Arg Pro Leu
        35                  40                  45

Leu Phe Ser Pro Asp Ala Pro Ala Leu Ala Glu Leu Leu Glu Ser Asp
    50                  55                  60

His Glu Arg Leu Asp Val Ala Ile Leu Ala Thr Ser Ile Ala Leu Ala
65                  70                  75                  80

Glu Leu Leu Glu Ser Arg His Gly Met Ser Pro Asp His Val Ala Gly
                85                  90                  95

His Ser Leu Gly Glu Phe Gly Ala Leu Ala Val Ala Gly Val Phe Thr
            100                 105                 110

Pro Gly Asp Ala Ala Arg Ala Val Cys Glu Arg His Ala Thr Leu Arg
        115                 120                 125

Lys Ala Pro Pro Thr Gly Gly Met Leu Ala Val Lys Ala Asp Ala
    130                 135                 140

Ala Arg Ala Gly Glu Leu Ile Ala Ala Arg Ala Gly Thr Ser Ala
145                 150                 155                 160

Val Ser Ala Leu Asn Ser Pro Ser Gln Thr Val Ile Ser Gly Ala Glu
                165                 170                 175

Ala Asp Leu Val Lys Val Gln Gln Leu Ala Arg Glu Glu Gly Ile Arg
            180                 185                 190
```

```
Thr Ser Arg Leu His Val Pro Gly Pro Phe His Val Pro Gln Leu Ala
        195                 200                 205

Asp Ala Ser Ala Leu Tyr Ala Thr Thr Met Arg Thr Ile Arg Ile Ser
    210                 215                 220

Ala Pro Arg Glu Arg Phe Phe Tyr Ser His Gly Leu Gly Arg Phe Leu
225                 230                 235                 240

Thr Ala Gln Asp Asp Val Val Asp Leu Met Val Asn Asp Met Thr Arg
                245                 250                 255

Pro Val Arg Phe His Asp Ser Val Arg Ala Leu Asn Ala Glu Gly Val
            260                 265                 270

Thr Thr Tyr Val Glu Cys Gly Ala Leu Asp Val Leu Thr Arg Ile Val
        275                 280                 285

Ser Gly Ser Leu Pro Arg Ala Val Thr Leu Ala Pro Leu Arg Glu Ala
    290                 295                 300

Thr Thr Thr Pro Asp Leu Ser Ala Arg Leu Arg Pro Ala Gly Thr Pro
305                 310                 315                 320

Ala Val Asn Gly Val Ala Ala Pro Gly Pro Ala Pro Ala Ala Glu
                325                 330                 335

Val Asp Pro Glu Val Leu Ala Gly Val Arg Ala Val Cys Ala Glu Val
            340                 345                 350

Leu Glu Tyr Pro Leu Glu Val Ile Thr Asp Asp Ala Asp Phe Gln Ala
        355                 360                 365

Asp Leu Gly Val Asp Ser Leu Ala Met Thr Glu Leu Gln Ala His Ala
    370                 375                 380

Leu Gln Arg Phe Gly Leu Lys Glu Thr Leu Gln Asp Ala Asp Thr Gly
385                 390                 395                 400

Thr Tyr Gly Thr Val Ser Gly Leu Ala Ala Tyr Ile Thr Gly Leu Leu
                405                 410                 415

Ser Glu Gly Thr Gly Ser Val Ser Gly Arg Arg
            420                 425

<210> SEQ ID NO 47
<211> LENGTH: 445
<212> TYPE: PRT
<213> ORGANISM: Streptomyces sp.

<400> SEQUENCE: 47

Met Thr His Val Arg Asp Ala Ala Thr Asp Asp Pro Gln Ala Ile
1               5                   10                  15

Ala Ala Cys Glu Val Pro Ala Gly Tyr Arg Ala Val Val Leu Ala
                20                  25                  30

Ala Asp His Gln Ala Leu Ala Gly Ser Pro Val Glu Asp Arg Asp Pro
            35                  40                  45

Arg Lys Thr Val Gln Val Gln Glu Val Pro Thr Pro Glu Pro Asp His
    50                  55                  60

Gly Glu Val Leu Ile Ala Thr Met Ala Ser Ser Ile Asn Tyr Asn Thr
65                  70                  75                  80

Val Trp Ser Ala Leu Phe Glu Pro Val Pro Thr Phe Arg Phe Leu Arg
                85                  90                  95

Thr Leu Gly Arg Thr Ser Pro Glu Ala Ala Arg His Asp Gln Pro Tyr
            100                 105                 110

His Val Leu Gly Ser Asp Leu Ser Gly Val Val Leu Arg Thr Gly Pro
        115                 120                 125

Gly Val Arg Glu Trp Lys Pro Gly Asp Glu Val Val Ala His Cys Leu
```

```
            130                 135                 140
Gln Pro Asp Leu Gln Thr Pro Gly Gly His Asp Asp Thr Leu Leu Asp
145                 150                 155                 160

Pro Gly Gln Arg Val Trp Gly Tyr Glu Thr Asn Phe Gly Gly Leu Ala
            165                 170                 175

Glu Leu Ser Leu Val Lys Ala Asn Gln Leu Met Pro Lys Pro Ala His
            180                 185                 190

Leu Thr Trp Glu Glu Ala Ala Ser Leu Gly Val Ala Leu Ser Thr Ala
            195                 200                 205

Tyr Arg Gln Leu Val Ser His His Gly Ala Ala Met Lys Gln Gly Glu
            210                 215                 220

Arg Val Leu Val Trp Gly Ala Ala Gly Val Gly Ala Tyr Ala Thr
225                 230                 235                 240

Gln Leu Ala Leu Asn Gly Gly Ala Val Pro Ile Cys Val Val Ser Ser
            245                 250                 255

Gln Ala Lys Ala Asp Leu Cys Arg Gln Met Gly Ala Glu Leu Val Ile
            260                 265                 270

Asp Arg Ala Ala Glu Gly Phe Ser Phe Trp Glu Gly Arg Asp Arg Pro
            275                 280                 285

Arg Leu Ser Glu Trp Ser Arg Phe Arg Gly Ala Val Arg Ser Leu Ala
            290                 295                 300

Gly Asp Asp Pro Asp Ile Val Ile Glu His Pro Gly Arg Asp Thr Phe
305                 310                 315                 320

Gly Val Ser Val Met Ile Ala Ala Arg Gly Gly Lys Val Val Thr Cys
            325                 330                 335

Ala Ser Thr Thr Gly Tyr Gln His Thr Tyr Asp Asn Arg His Leu Trp
            340                 345                 350

Met Arg Val Lys Arg Ile Ile Gly Ser His Met Ala Asn Tyr Arg Glu
            355                 360                 365

Ala Trp Ala Ala Asn Glu Leu Val Ala Arg Gly Ser Ile His Pro Val
            370                 375                 380

Leu Ser Arg Val Tyr Pro Leu Asp Ala Thr Gly Asp Ala Thr His Ala
385                 390                 395                 400

Val Ala Asn Asn Ser His His Gly Lys Val Gly Val Leu Cys Leu Ala
            405                 410                 415

Asp Arg Pro Gly Met Gly Val Arg Asp Pro Glu Leu Arg Ala Arg Lys
            420                 425                 430

Leu Asp Ser Ile Asn Leu Phe Arg Lys Gly Gln Pro Arg
            435                 440                 445

<210> SEQ ID NO 48
<211> LENGTH: 386
<212> TYPE: PRT
<213> ORGANISM: Streptomyces sp.

<400> SEQUENCE: 48

Met Ser Glu Ser Glu Arg Leu Gly Ile Val Arg Asp Phe Val Ala Arg
1               5                   10                  15

Glu Ile Leu Gly Arg Glu Gly Ile Leu Asp Ser Leu Ala Asp Ala Pro
            20                  25                  30

Leu Ala Leu Tyr Glu Arg Phe Ala Glu Thr Gly Leu Met Asn Trp Trp
            35                  40                  45

Val Pro Lys Glu His Gly Gly Leu Gly Leu Gly Leu Glu Glu Ser Val
        50                  55                  60
```

-continued

Arg Ile Val Ser Glu Leu Ala Tyr Gly Asp Ala Gly Val Ala Phe Thr
 65                  70                  75                  80

Leu Phe Leu Pro Val Leu Thr Thr Ser Met Ile Gly Trp Tyr Gly Ser
                 85                  90                  95

Glu Glu Leu Lys Glu Arg Phe Leu Gly Pro Leu Val Ala Arg Arg Gly
             100                 105                 110

Phe Cys Ala Thr Leu Gly Ser Glu His Glu Ala Gly Ser Glu Leu Ala
             115                 120                 125

Arg Ile Ser Thr Thr Val Arg Arg Asp Gly Asp Thr Leu Val Leu Asp
         130                 135                 140

Gly Thr Lys Ala Phe Ser Thr Ser Thr Asp Phe Ala Arg Phe Leu Val
145                 150                 155                 160

Val Ile Ala Arg Ser Ala Asp Asp Pro Ala Arg Tyr Thr Ala Val Thr
                 165                 170                 175

Val Pro Arg Asp Ala Pro Gly Leu Arg Val Asp Lys Arg Trp Asp Val
             180                 185                 190

Ile Gly Met Arg Ala Ser Ala Thr Tyr Gln Val Ser Phe Ser Asp Cys
             195                 200                 205

Arg Val Pro Gly Asp Asn Ala Leu Asn Gly Asn Gly Leu Arg Leu Leu
         210                 215                 220

Glu Ile Gly Leu Asn Ala Ser Arg Ile Leu Ile Ala Ala Ser Ala Leu
225                 230                 235                 240

Gly Val Ala Arg Arg Ile Arg Asp Val Cys Met Glu Tyr Gly Lys Thr
                 245                 250                 255

Lys Ser Leu Lys Gly Ala Pro Leu Val Lys Asp Gly Val Phe Ala Gly
             260                 265                 270

Arg Leu Gly Gln Phe Glu Met Gln Ile Asp Val Met Ala Asn Gln Cys
         275                 280                 285

Leu Ala Ala Arg Ala Tyr Asp Ala Thr Ala Ala Arg Pro Asp Ala
290                 295                 300

Ala Arg Val Leu Leu Arg Gln Gly Ala Gln Lys Ser Ala Leu Thr Ala
305                 310                 315                 320

Lys Met Phe Cys Gly Gln Thr Ala Trp Gln Ile Ala Ser Thr Ala Ser
                 325                 330                 335

Glu Met Phe Gly Gly Ile Gly Tyr Thr His Asp Met Val Ile Gly Lys
             340                 345                 350

Leu Leu Arg Asp Val Arg His Ala Ser Ile Ile Glu Gly Gly Asp Asp
         355                 360                 365

Val Leu Arg Asp Leu Val Tyr Gln Arg Phe Val Val Pro Thr Ala Lys
370                 375                 380

Arg Thr
385

TACROLIMUS ANALOGUES, A NEUROPROTECTIVE COMPOSITION COMPRISING THE SAME, AN IMMUNOSUPPRESSIVE COMPOSITION COMPRISING THE SAME, A METHOD FOR PREPARING THE SAME, AND A MUTANT FOR PRODUCING THE SAME

RELATED APPLICATIONS

This application is a continuation-in-part of International Application No. PCT/KR2011/003644 filed on May 17, 2011, which claims priority to Application No. 10-2010-0082059 filed in Korea on Aug. 24, 2010 and Application No. 10-2011-0032278 filed in Korea on Apr. 7, 2011, all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created May 14, 2013, is named 42861702501.txt and is 33,319 bytes in size.

TECHNICAL FIELD

The present invention relates to novel tacrolimus analogues, a composition for the prevention or treatment of neurological diseases or immune hypersensitivity disorders comprising the same, a method for preventing or treating neurological diseases or immune hypersensitivity disorders comprising administering the analogues to a subject, a method for preparing the analogues using an isolated modified *Streptomyces* sp. strain wherein the activity of one or more enzymes selected from the group consisting of endogenous TcsA, TcsB, TcsC and TcsD is reduced; and the isolated modified *Streptomyces* sp. strain for prepare the analogues.

BACKGROUND ART

Polyketides including tacrolimus (FK506), rapamycin, and ascomycin (FK520) are natural products having a complex structure, produced by microorganisms, and more than 10,000 compounds are known. Mainly anticancer agents, antibiotics, antihypertensive agents, immunosuppressive agent or the like have been developed from these compounds, and account for approximately 50% of natural product-derived drugs currently used. Tacrolimus, rapamycin and ascomycin have a similar structure to inhibit T cell activation both in vitro as well as in vivo. It was reported that these compounds have a pyranose-pipecolinyl region, which is similar to leucine-proline peptide in the structure, and exhibit a variety of physiological activities by binding of peptidyl prolyl cis/trans isomerase.

The biosynthesis of polyketides is catalyzed by a megasynthase called polyketide synthase (PKS). These PKS complexes consist of several modules (sets of catalytic domains, each domain is responsible for one condensation step) involved in repetitive Claisen condensations from acyl-CoA, and the typical modular PKS is composed of a loading module, multiple extender modules, and a releasing module. The variation of catalytic domains within the modules affords the structural diversity in the resultant polyketide products with one-to-one correspondence. Among the modules, each extender module contains acyl transferase (AT), acyl carrier protein (ACP) and β-ketoacyl synthase (KS) domains that are directly involved in condensation of carboxylic acids, and also contains keto reductase (KR), dehydratase (DH), and enoyl reductase (ER) domains that are involved in reduction of a resultant β-keto group produced by the condensation. The addition of acyl-coA residue is mediated by one action of a module, in which AT transfers an acyl moiety to the corresponding ACP to produce acyl-ACP, and KS catalyzes the carbon-carbon bond formation via the Claisen condensation reaction of acyl group of acyl-ACP produced by the previous module, leading to an increase in the number of carbon. For instance, an action of this set mediates the addition of one acyl residue, resulting in an extension by two carbon atoms in the carbon chain backbone. During this process, KR, DH, and ER act in turn and thus, the β-keto group may be converted to an alcohol group, the alcohol group to a double bond, and the double bond to a saturated single bond.

Tacrolimus is a macrolide antibiotic having immunosuppressive properties, discovered from the culture broth of *Streptomyces tsukubaensis*, which is a bacterium found in the soil near Tsukuba, Northern Japan. Tacrolimus is an immunosuppressive agent used for the prevention of organ rejection after kidney and liver transplantation, approved by the US FDA in 1993, and is commercially available under the trade name of PROGRAF® (oral capsule or injectable) provided by Fujisawa Healthcare Inc. in 1994.

It was reported that tacrolimus is produced from strains such as *Streptomyces tsukubaensis* No. 9993 (U.S. Pat. No. 4,894,366), *Streptomyces* sp. ATCC55098, *Streptomyces* sp. MA 6858 (U.S. Pat. No. 5,116,756), *Streptomyces* sp. ATCC 53770, *Streptomyces clavuligerus* CKD1119 (Korean Patent No. 10-0485877), *Streptomyces kanamyceticus* KCC S-043 (KCTC 9225) or the like (Muramatsu H. et al., Actinomycetologica 19, 33-39 (2005)).

From a biosynthetic viewpoint, FK506 has a structurally unique feature in comparison with FK520 and rapamycin. FK506 is the only polyketide which carries an allyl side chain. Whereas the complete sequencing and characterization of the biosynthetic gene clusters of FK506 and FK520 were reported by Motamedi et al., (Eur. J. Biochem. 244, 528-34, 1998) and Wu et al., (Gene, 251, 81-90, 2000), respectively, only the partial sequence of FK506 gene cluster has been reported until quite recently. Consequently, the biosynthetic mechanism behind the introduction of the allyl functional group unique to FK506 has remained unresolved. The above biosynthetic pathway has to be identified first to prepare tacrolimus analogues with similar efficacy but reduced toxicity compared to tacrolimus or a tacrolimus analogue with the improved efficacy.

As FK506 analogues, FK520, dihydrotacrolimus, FK523, FK525 or the like are known, in which FK520 is a 23-membered macrolide compound and an ethyl analog of FK506 (Hatanaka H. et al., 1998), dihydrotacrolimus is a C21-propyl analogue of FK506, FK523 is a C21-methyl analogue of FK506, and FK525 is a prolyl analogue of FK506.

DISCLOSURE

Technical Problem

The present inventors systematically investigated the biosynthetic route generating the unique C21 allyl moiety of FK506. They also investigated a method for preparing novel tacrolimus analogues by deletion of a gene which is involved in the generation of the unique C21 allyl moiety of FK506.

Technical Solution

The present invention provides an isolated modified *Streptomyces* sp. strain in which the activity of endogenous TcsB is reduced.

Further, the present invention provides a method for preparing a tacrolimus analogue using the isolated modified *Streptomyces* sp. strain.

Further, the present invention provides a tacrolimus analogue represented by the following Formula 1, an isomer thereof, a pharmaceutically acceptable salt thereof, or a combination thereof.

[Formula 1]

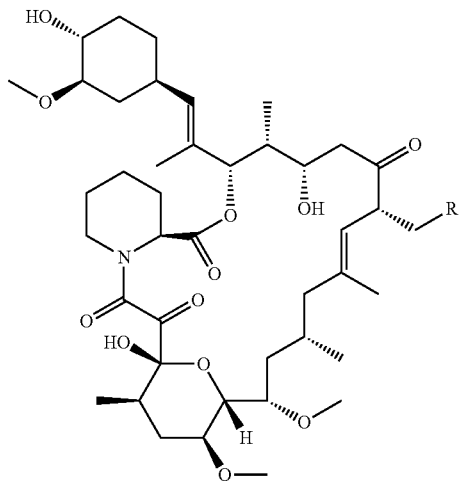

wherein R is

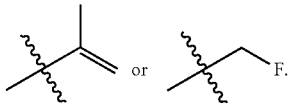

Further, the present invention provides a pharmaceutical composition, comprising the tacrolimus analogue represented by the Formula 1, an isomer thereof, or a pharmaceutically acceptable salt thereof.

Further, the present invention provides a method for treating neurological diseases comprising administering the composition to a subject in need thereof.

Further, the present invention provides a method for treating immune hypersensitivity disorders comprising administering the composition to a subject in need thereof.

Further, the present invention provides a method for suppressing immune responses comprising administering the composition to a subject in need thereof.

Furthermore, the present invention provides a method for preparing a tacrolimus analogue using a *Streptomyces* sp. strain wherein the activity of one or more enzymes selected from the group consisting of endogenous TcsA, TcsB, TcsC and TcsD is reduced.

Advantageous Effects

The biosynthetic route of tacrolimus can be understood through the present invention, and novel tacrolimus analogues, which are more excellent in neuroprotective and immunosuppressive effects than tacrolimus, can be produced by using the method of the present invention.

DESCRIPTION OF DRAWINGS

FIGS. 15A and B show NMR data for the novel FK506 analogue, 36-methyl-FK506;

FIGS. 23A and B show NMR data for the novel FK506 analogue, 36-fluoro-FK520;

FIG. 24 shows binding free energies of calcineurin-FKBP12 complex with FK506 analogues, in which the binding free energies were based on molecular dynamics simulation, all energies are given in units of kcal/mol, and each of ΔGelec, ΔGvdw, ΔGnonp/sol, ΔGelec/sol, and ΔGbind represents electrostatic, van der Waals, nonpolar solvation, electrostatic solvation, and binding free energies (1, FK506; 2, FK520; 33, 36-methyl-FK506; 34, 36-fluoro-FK520).

BEST MODE

Figure 1:
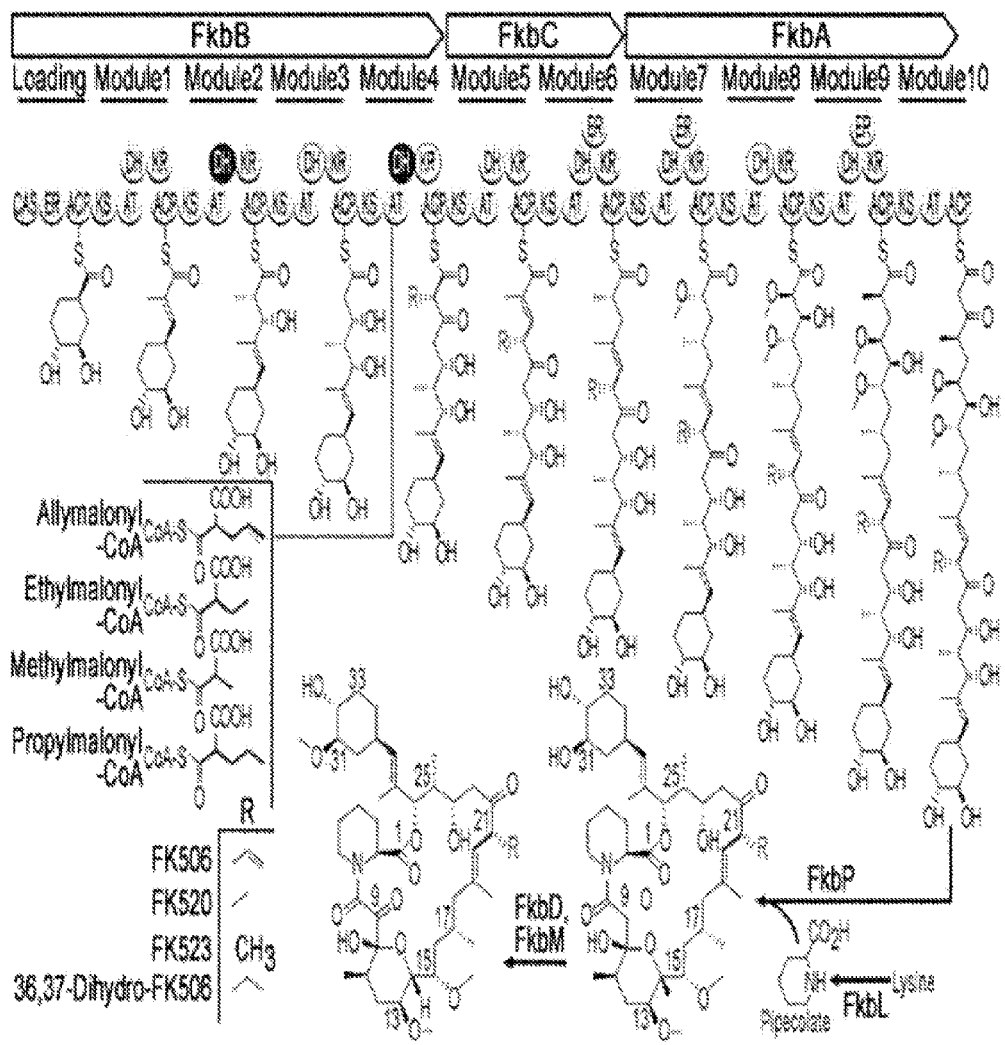
FIG. 1 is a schematic representation of the FK506 PKS and biosynthesis of FK506 and its analogues, in which domains within each module are represented by circles, and black and white circles indicate domains that are not predicted to be active from the final structure and domains that are nonfunctional due to deletions in the active sites, respectively (CAS, CoA synthetase; KS, ketoacyl synthase; AT, acyl transferase; DH, dehydratase; ER, enoyl reductase; KR, keto reductase; ACP, acyl carrier protein)

As one aspect, the present invention provides an isolated modified Streptomyces sp. strain in which the activity of endogenous TcsB is reduced.

As used herein, the term 'TcsB' refers to the enzyme involved in the synthesis of C21 allyl side chain of tacrolimus (FK506). For the purpose of the present invention, the TcsB means the enzyme which functions as a priming KS acylated by propionyl-CoA and catalyzes the condensation with malonate loaded on TcsA, but is not limited thereto.

In the present invention, based on a comprehensive chemical, biochemical and genetic interrogation of three FK506 gene clusters, four proteins (TcsA, TcsB, TcsC and TcsD) involved in the synthesis of allylmalonyl-coenzyme A(CoA), from which the FK506 allyl group is derived, and the biosynthetic pathway thereof are elucidated. Specifically, in the present invention, the dedicated involvement of TcsB in synthesis of C21 allyl moiety of tacrolimus is elucidated for the first time. Also, in the present invention, it was investigated that the TcsB catalyzes the decarboxylative Claisen condensation in the process of allylmalonyl-CoA synthesis. Thus, the tacrolimus analogues containing altered moieties at C21 can be produced by reducing the endogenous activity of TcsB and then feeding a series of carboxylic acids. In addition, the TcsB is the protein encoded by tcsB gene with SEQ ID NO. 1, for example, is the protein having an amino acid sequence of SEQ ID NO. 42, but it not limited thereto.

In addition, the TcsB may refer to the protein possessing the amino acid sequence of SEQ ID NO. 42, but also an amino acid sequence having a sequence homology of 70% or higher, preferably 80% or higher, more preferably 90% or higher, even more preferably 95% or higher, even much more preferably 98% or higher, and most preferably 99% or higher to the amino acid sequence of SEQ ID NO. 42. However, any protein can be used without limitation, as long as it has ketoacyl synthase activity. In addition, if the protein with the above sequence homology has substantially the same or corresponding bioactivity as TcsB even the variants of the protein having a portion of amino acid sequence deleted, modified, substituted, or added may be included in the scope of the present invention.

The polynucleotide that encodes the TcsB may be preferably a polynucleotide represented by a nucleotide sequence of SEQ ID NO. 1, and also includes any nucleotide sequence having a sequence homology of 70% or higher, preferably 80% or higher, more preferably 90% or higher, much more preferably 95% or higher, and most preferably 98% or higher homology to the nucleotide sequence of SEQ ID NO. 1 without limitation, as long as it is able to substantially encode a protein having TcsB activity.

As used herein, the term "homology" is intended to indicate the degree of similarity to the amino acid sequence of a wild type protein or a nucleotide sequence that encodes the same, and includes sequences having homology of the above percentage or higher with the amino acid sequence or base sequence of the present invention. Homology comparisons can be conducted by sight or by readily available sequence comparison programs.

As used herein, the term 'Tacrolimus (FK506)' refers to a 23-membered macrocyclic polyketide produced by several *Streptomyces* species that possess antifungal and immunosuppressive activities, and is represented by the following Formula 2.

Specifically, tacrolimus is distinct from other polyketides due to C21 allyl chain.

[Formula 2]

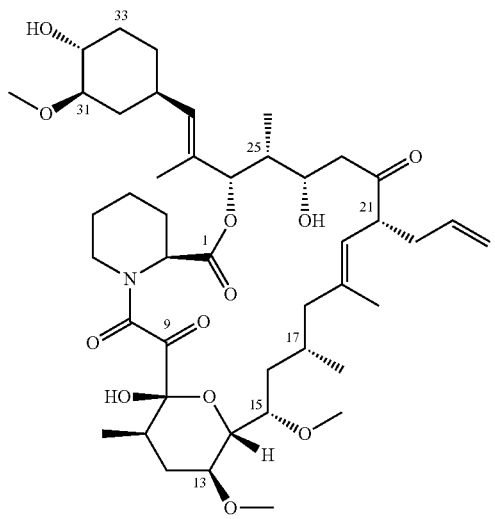

Figure 6:
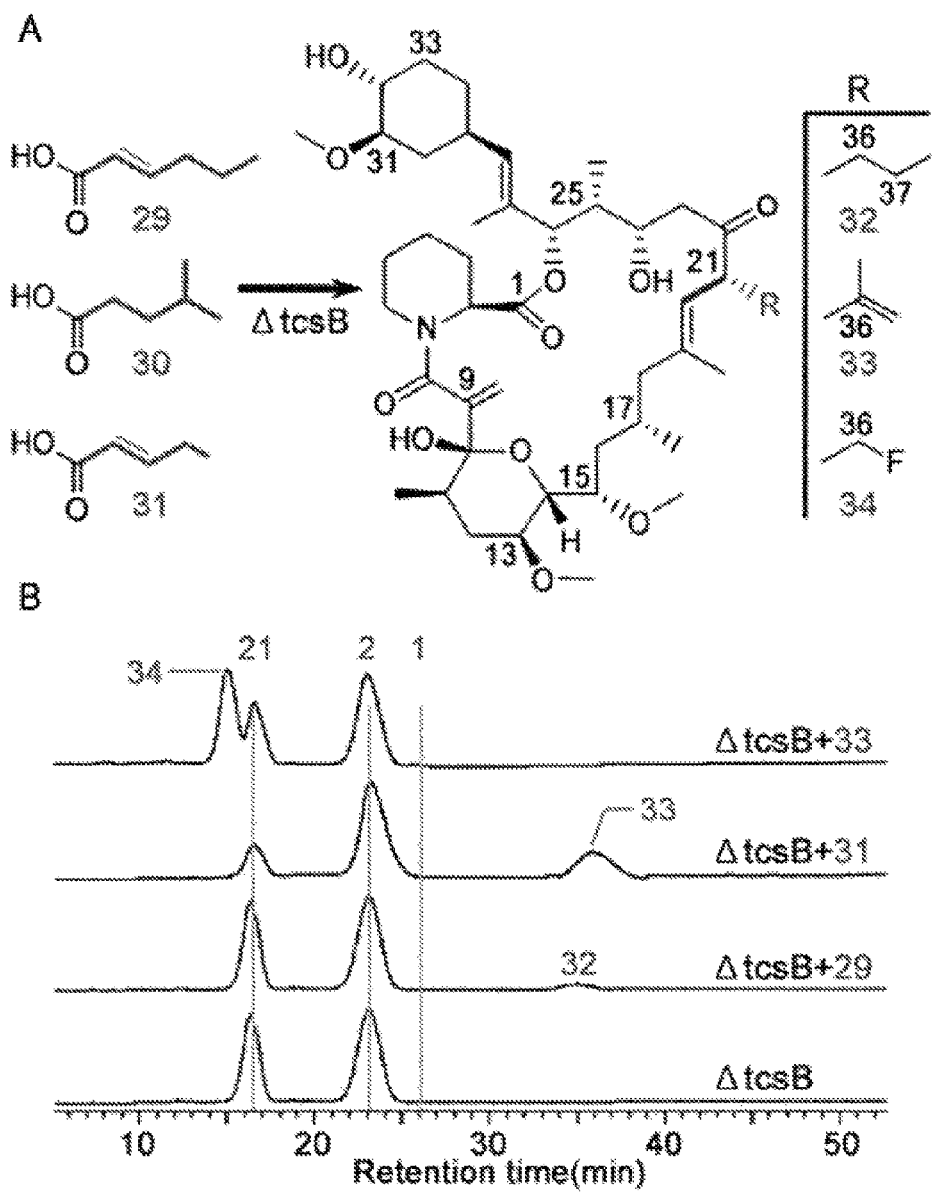
FIG. 6 shows generation of novel FK506 analogues through mutasynthesis, in which (A) chemical structure of the FK506 analogues 36,37-dihydro-37-methyl-FK506 (32), 36-methyl-FK506 (33) and 36-fluoro-FK520 (34), (B) HPLC-ESI-MS/MS chromatograms obtained from a culture of FK520- and FK523-producing tcsB deletion mutants of KCTC 11604BP (ΔtcsB strain), separately supplemented with trans-2-hexenoic acid (29), 4-methylpentanoic acid (30), or 4-fluorocrotonic acid (31), and each vertical blue dotted line indicates the identity of one of the FK506 congeners (FK523 (21), FK520 (2), or FK506 (1))

As used herein, the term 'tacrolimus analogue' refers to a compound having a structure similar to tacrolimus, but differing from it in respect of a certain component. It can differ in one or more atoms, functional groups, or substructures by substitution of the original compound with other atoms, groups, or substructures. For the purpose of the present invention, the tacrolimus analogue means a compound having C21 ally group of FK506 replaced by other side chain, but is not limited thereto. The tacrolimus analogue can be prepared by using the isolated modified *Streptomyces* sp. strain. In specific Example of the present invention, the tcsB-deleted *Streptomyces* sp. strain of the present invention was fed with 4-methylpentanoic acid or 4-fluorocrotonic acid to produce 36-methyl-FK506 or 36-fluoro-FK520, respectively (FIG. 6). The above analogues are the representative analogues which can be prepared by the method of the present invention, and are the example of the analogues containing altered side chains at C21.

As used herein, the term 'modified *Streptomyces* sp. strain' refers to a *Streptomyces* sp. strain having gene mutations. For the purpose of the present invention, the modified *Streptomyces* sp. strain refers to a *Streptomyces* sp. strain comprising a modified protein involved in the biosynthesis of C21 allyl group of tacrolimus, preferably, to a *Streptomyces* sp. strain in which the activity of one or more enzymes selected from the group consisting of TcsA, TcsB, TcsC and TcsD is reduced, more preferably to a *Streptomyces* sp. strain in which the activity of TcsB is reduced compared to the endogenous activity thereof. Further, the *Streptomyces* sp. strain may preferably be a tacrolimus-producing strain.

As used herein, the term 'tacrolimus-producing strain' refers to a *Streptomyces* sp. strain that is able to produce tacrolimus. For example, the strain can be selected from the group consisting of *Streptomyces* sp. KCTC 11604BP, *Streptomyces kanamyceticus* KCTC 9225, *Streptomyces* sp. ATCC 55098, *Streptomyces tsukubaensis* No. 9993, *Streptomyces* sp. ATCC 53770, *Streptomyces* sp. 6260, *Streptomyces* sp. 49A, *Streptomyces* sp. 94128, *Streptomyces glaucescens* MTCC 5115 and *Streptomyces* sp. BICC 7522. The strains to be used are not particularly limited, and any known tacrolimus-producing strain may be used.

The modified *Streptomyces* sp. strain may be a strain having reduced activity of endogenous TcsB, but is not limited thereto.

As used herein, the term 'endogenous activity' refers to the enzyme activity that occurs in the wild-type strain. In the present invention, the endogenous activity refers to the TcsB activity that occurs in the wild-type *Streptomyces* sp. strain.

The reduced TcsB activity means a decrease in TcsB activity, compared to that of a wild-type strain, and encompasses the disruption of TcsB. Various techniques for reduction of TcsB activity are well known in the art. Illustrative examples include the substitution of the tcsB gene with the mutated gene to reduce the endogenous TcsB activity, mutation of the regulatory region of the tcsB gene to reduce endogenouse TcsB activity, substitution of the regulatory region of the gene encoding TcsB with a regulatory element having weaker activity, deletion of the tcsB gene, introduction of an antisense oligonucleotide complementary to the mRNA sequence of the tcsB gene to inhibit the translation of the mRNA, insertion of the sequence complementary to shine-dalgarno (SD) sequence of the gene encoding TcsB on the upstream of the SD sequence of the same, and induction of reverse transcription by adding a promoter to 3' terminal of open reading frame (ORF) of the nucleotide sequence encoding TcsB, but methods for reducing the TcsB activity are not limited to these. These techniques may be applied to reduce the activity of other enzymes in the present invention.

In the present invention, the gene deletion method was used as a representative method for reducing TcsB activity. However, other methods for reduction of TcsB activity can be used for preparing the modified *Streptomyces* sp. strain capable to produce the tacrolimus analogues containing altered C21 side chain.

As used herein, the term 'gene deletion' means the loss of gene function by deletion of all or a part of the corresponding gene. The strain may have a deletion of 175 to 2,262 bases in the tcsB gene with SEQ ID NO. 1. The strain may be prepared by the method described in the detailed description and Examples of the present invention, for example, in-frame deletion, but is not limited thereto.

In addition, specific deletion of a target gene in the genome may be performed by any method established in the art, but the method is not particularly limited, and a homologous recombination method may be used. A *Streptomyces* sp. strain is transformed with a vector including a selection marker between nucleic acids encoding N- and C-terminus of the desired protein to induce recombination between the genome and the vector. The selection marker to be used is not particularly limited, and a selection marker that confers a selectable phenotype, such as drug resistance, nutritional auxotrophy, resistance to a cytotoxic agent or expression of a surface protein, can be used. In the specific example of the present invention, tcsB-deleted strain prepared by the method described in the Examples of the present invention was deposited at the Korean Collection for Type Cultures (KCTC) under the Budapest Treaty on Feb. 25, 2011 with Accession No. KCTC 11879BP.

As another aspect, the present invention provides a method for preparing a tacrolimus analogue using the isolated modified *Streptomyces* sp. strain.

To be specific, the present invention provides a method for preparing a tacrolimus analogue in which C21 allyl group is substituted, comprising (a) culturing the isolated modified *Streptomyces* sp. strain in which the activity of endogenous TcsB is reduced; and (b) feeding carboxylic acids to the strain.

[Formula 2]

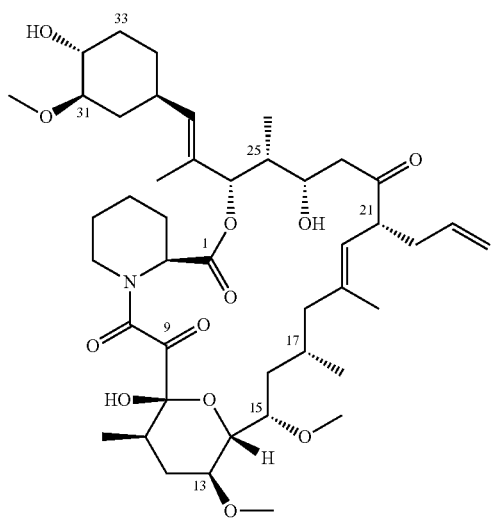

The isolated modified *Streptomyces* sp. strain, the tacrolimus and the tacrolimus analogue are the same as described above.

Further, the above method may further comprises (c) extracting the tacrolimus analogues from the culture medium of the strain.

The above method uses *Streptomyces* sp. strain wherein the enzyme activity of TcsB involved in the biosynthesis of C21 allyl group of tacrolimus is reduced, and thus depending on the type of carboxylic acid added, various types of tacrolimus analogues can be produced having C21 allyl group substituted with other functional groups.

In the method of the present invention, the step (a) is the culturing of the isolated modified *Streptomyces* sp. strain.

The strain for producing the novel tacrolimus analogues of the present invention may be cultured in the media containing nutrients typically used by microorganisms. As the nutrient sources of the strain, any nutrient source typically used in the art may be used without limitation, and the known nutrient sources used for the culture of *Streptomyces* sp. bacteria may be preferably used. For example, the culture is preferably performed in a media containing malonic acid, ethanol, methionine, carbon sources, and nitrogen sources. At this time, as the carbon source, one or more substances are preferably selected from a group consisting of starch, glucose, corn oil, glycerol, maltose, mannose and inositol, and starch, glucose and corn oil are most preferred. As the nitrogen source, one or more substances are selected preferably from a group consisting of cottonseed flour, corn steep liquor, corn steep powder, soybean flour, peptone and yeast extract, and among them, cotton seed flour and corn steep liquor are most preferred. A seed culture solution was inoculated in a fermentor containing the above-mentioned medium. The culture method may be a stationary culture or a shaking culture under aerobic conditions. The culture temperature may differ depending on the above culture conditions, and the culture is usually performed at 20-37° C., and preferably at 26-30° C. In addition, the culture may be performed for a suitable period known in the art, and if necessary, the period may be adjusted. Preferably, in the case of performing stationary culture or shaking culture, it may be performed for 4 days to 7 days. Then, the culture solution is filtered and extraction may be performed to obtain oily residue. A fraction including a target compound can be purified by column chromatography, resulting in novel pure tacrolimus analogues.

In the method of the present invention, step (b) is the feeding of carboxylic acids to the strain.

In the modified strain, the endogenous activity of TcsB involved in the biosynthesis of C21 allyl group of tacrolimus is reduced, and thus the tacrolimus containing allyl functional group at C21 cannot be produced properly. Therefore, when the strain is fed with a series of carboxylic acids, tacrolimus analogues having alternative C21 side chain can be produced.

As used herein, the term 'carboxylic acid' refers to the compound containing carboxylic acid group, as the substance supplied to *Streptomyces* sp. strain that is modified to produce tacrolimus analogues. For the purpose of the present invention, the carboxylic acid means a non-natural extender unit. As used herein the term 'non-natural extender unit' refers to any compound which can be incorporated as an extender unit in polyketide synthesis that is not the usual extender unit incorporated by the PKS. Extender units are suitably provided as the free carboxylic acid, but derivatives that may be employed include salts.

The type of carboxylic acid is not limited as long as the tacrolimus analogue having C21 allyl group substituted can be produced by feeding the carboxylic acid to the modified strain. Example of such carboxylic acid includes C4 to C7 carboxylic acids such as 4-halocrotonic acids, branched/4-halobutanoic acids, branched/unsaturated/5-halopentanoic acids, branched/unsaturated hexanoic acids, and heptanoic acid, but is not limited thereto. In addition, the carboxylic acid may be 4-methylpentanoic acid or 4-fluorocrotonic acid, but is not limited thereto.

In specific Example of the present invention, the tcsB-deleted *Streptomyces* sp. strain of the present invention was fed with 4-methylpentanoic acid or 4-fluorocrotonic acid to produce 36-methyl-FK506 or 36-fluoro-FK520, respectively.

As another aspect, the present invention provides a tacrolimus analogue represented by the following Formula 1, an isomer thereof, a pharmaceutically acceptable salt thereof, or combination thereof.

[Formula 1]

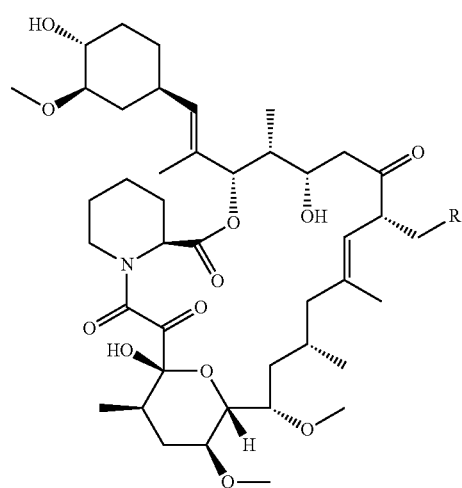

wherein R is

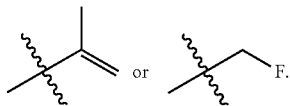

The tacrolimus and its analogues is the same as described above.

In the compound represented by Formula 1, if R is

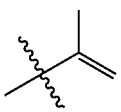

(1-propen-2-yl), the compound is 36-methyl-FK506, and if R is

(fluoromethyl), the compound is 36-fluoro-FK520. More particularly, 36-methyl-FK506 and 36-fluoro-FK520 have the following chemical structure.

36-methyl-FK506

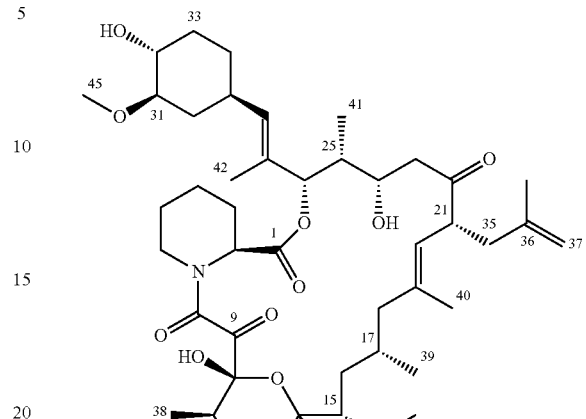

[36-methyl-FK506]

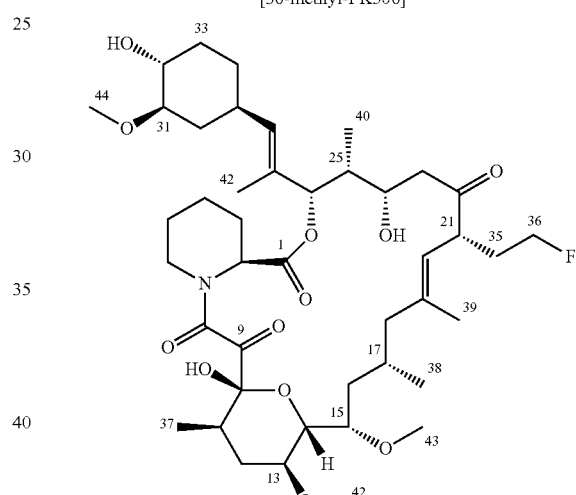

[36-fluoro-FK520]

Preferably, the compounds of the present invention include an isomer or a pharmaceutically acceptable salt thereof.

The isomer denotes the chemical relationship of having the same chemical formula but different structures, and the type of isomers includes structural isomer, geometric isomer, optical isomer and geometric isomer. Stereoisomer means that different compounds have the same chemical constitution but differ in the arrangement of their atoms or groups in space, optical isomer (mirror image isomer) means two stereoisomers of one compound, which have non-superimposable mirror images, and diastereoisomers mean stereoisomers that possess two or more chiral centers and are not mirror images. And further, the compounds of the present invention may be in the form of a solvate or pro-drug, which is included within the scope of the present invention. The solvate preferably includes a hydrate and an ethanolate.

As used herein, the term 'pharmaceutically acceptable salt' refers to a relatively non-toxic, inorganic or organic acid addition salt of a compound.

For the salts, an acid-addition salt thereof formed by a pharmaceutically acceptable free acid thereof is useful. As used herein, the term 'pharmaceutically acceptable salt' is any organic or inorganic acid addition salt, which is relatively non-toxic and harmless to a patient in a pharmaceutical dose of the salt, so that the beneficial effects inherent in the compound of Formula 1 are not deteriorated by side effects ascribable to the salt.

For example, after dissolving the compound in the excess amount of acid solution, the salts are precipitated by a water-miscible organic solvent such as methanol, ethanol, acetone or acetonitrile to prepare the acid addition salt thereof. Further, the mixture of equivalent amount of compound and diluted acid with water or alcohol (e.g., glycol monomethylether) can be heated and subsequently dried by evaporation or filtrated under reduced pressure to obtain the dried salt form thereof.

As a free acid, an organic acid or inorganic acid may be used. Examples of the inorganic acid may include hydrochloric acid, phosphoric acid, sulfuric acid, nitric acid, tartaric acid and the like, and examples of the organic acid may include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolicacid, gluconic acid, galacturonic acid, glutamic acid, glutaric acid, glucuronic acid, aspartic acid, ascorbic acid, carbonic acid, vanillic acid, and hydroiodic acid, but are not limited thereto.

In addition, a pharmaceutically acceptable metal salt may be prepared using a base. An alkali metal or alkaline earth metal salt may be obtained, for example, by dissolving a compound in an excess amount of alkali metal hydroxide or alkaline earth metal hydroxide solution, filtering the undissolved salt, and then evaporating the filtrate until dry. As the metal salts, sodium, potassium or calcium salts are pharmaceutically suitable, but the present invention is not limited thereto. Also, the corresponding silver salts may be obtained by reacting an alkali metal or alkaline earth metal salt with a proper silver salt (e.g., silver nitrate).

Pharmaceutically acceptable salts of the compound represented by Formula 1, unless otherwise indicated herein, include salts of acidic or basic groups, which may be present in the compound of Formula 1. For example, the pharmaceutically acceptable salts may include sodium, calcium and potassium salts of hydroxy group, and other pharmaceutically acceptable salts of amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate). The salts may be prepared using a salt preparation method known in the art.

The compounds of the present invention may be synthesized according to the method typically used in the art, and may be preferably produced from the mutant using the method of the present invention. Preferably, the compounds of the present invention may be produced from a *Streptomyces* sp. strain or the like, but the type of the strain that produces the compounds of the present invention is not limited to the above strains.

In the specific Example of the present invention, NMR analysis revealed that 36-methyl-FK506 and 36-fluoro-FK520 of Formula 1 were revealed as tacrolimus analogues.

As another aspect, the present invention provides a pharmaceutical composition, comprising the tacrolimus analogue represented by the Formula 1, an isomer thereof, a pharmaceutically acceptable salt thereof.

The tacrolimus analogue represented by the Formula 1, the isomer and the pharmaceutically acceptable salt is the same as the described above. In addition, the compound of Formula 1 includes all of a compound, wherein R is 1-propen-2-yl or fluoromethyl, and combination thereof.

Preferably, the pharmaceutical composition is used for prevention or treatment of neurological diseases or immune hypersensitivity disorders.

The 36-methyl-FK506 compound and 36-fluoro-FK520 compound show the neurite outgrowth activity, and thus the composition comprising the compound can be used for the prevention or treatment of neurological diseases.

As used herein, the term 'prevention or treatment' means all of the actions in which a disease is restrained or retarded, in particular, the term 'treatment' refers to alocal or systemic effect in animals, particularly mammals, and more particularly humans, caused by a pharmacologically active substance. The term thus means any substance intended for use in diagnosis, cure, mitigation, treatment or prevention of disease or in the enhancement of desirable physical or mental development and conditions in an animal or human.

As used herein, the term 'neurological diseases' refers to various neuropathological states and neurological diseases, including physical injury (e.g., spinal cord injury and trauma, sciatic or facial nerve lesion or injury, limb transplantation following amputation), nutritional disorders, ischemia, degenerative diseases, malignant diseases, infectious diseases, and damage to peripheral nerves and the central nervous system caused by drug interactions, cancer chemotherapy (e.g., acrylamide, taxol, *vinca* alkaloids and doxorubicin), toxins or poisons, asthenia, neurological damage or dysfunction, specifically, neurological damage or dysfunction caused by neurosurgery, peripheral nerve injury, burns, encephalomyelitis, HIV, herpes, cancer, radiation treatment, drug interaction, folic acid or Vitamin B-12 deficiency, and by exposure to neurotoxins or chemicals such as lead, and more specifically, allophasis (e.g., articulation disorders) associated with cerebral infarction, hemorrhage infarct, etc., clouding of consciousness, dyskinesia, trigeminal neuralgia, glossopharyngeal neuralgia, facial palsy, myasthenia gravis, muscular dystrophy, amyotrophic lateral sclerosis, progressive muscular atrophy, hereditary progressive bulbar muscular atrophy, herniated intervertebral disc (herniated), ruptured intervertebral disc (ruptured), or prolapsed intervertebral disc syndrome, cervical spondylosis, plexus disease, thoracic outlet syndrome, peripheral neuropathy, glue-sniffer's neuropathy, Guillain-Barre syndrome, Alzheimer's disease, Parkinson's disease, Huntington's chorea, polymyositis, Meniere's disease, polyneuritis, isolated neuritis, amyotrophic lateral sclerosis (ALS), radiculopathy, diabetic neuropathy, senile dementia, vascular dementia, multiple sclerosis.

Especially, Alzheimer's disease, Parkinson's disease, amyotrophic lateral sclerosis (ALS), multiple sclerosis, diabetic neuropathy, Huntington's chorea, and peripheral neuropathy are all resulted from the damage or degeneration of the nerve cells. For the treatment of the diseases induced by the damage or degeneration of the nerve cells, substance with the neurite outgrowth activity is useful. Especially for the degenerative brain disease such as Alzheimer's disease, the lack of substance contributing to neurite outgrowth can be one of the causes of the onset of the disease, and thus the substance promoting the neurite outgrowth is known to be useful for treatment of degenerative brain disease (Yuto Kamei and Atsuko Sagara, Cytotechnology. 2002 November; 40(1-3): 99-106. More S V et al., Molecules. 2012 Jun. 4; 17(6):6728-53.).

In the specific Example of the present invention, neurite outgrowth activity of the compound was evaluated. Consequently, the compound of the present invention was found to show excellent effect of promoting neuroregeneration and functional recovery by stimulation of neurite growth, compared with tacrolimus and other analogs.

Further, the pharmaceutical composition comprising 36-methyl-FK506, 36-fluoro-FK520 or combinations thereof may be used for the prevention or treatment of immune hypersensitivity disorder, but is not limited thereto.

The 36-methyl-FK506 compound and 36-fluoro-FK520 compound demonstrate the immunosuppressive activity, and thus the composition comprising the compound can be used for suppressing immune responses, in advance, for the prevention or treatment of the immune hypersensitivity disorder.

As used herein, the term 'immunosuppressive' means that immune response in an organism is reduced or depressed. The immunosuppressive composition according to the present invention can be used for the prevention or treatment of immune hypersensitivity disorders. The immune hypersensitivity disorders mean the pathologic state due to abnormal activation of immune system, and examples thereof include, but are not limited to, transplant rejection; autoimmune diseases such as lupus and rheumatoid arthritis; skin hypersensitivity including allergic diseases such as rhinitis, asthma, and atopic dermatitis. In addition, the immunosuppressive composition according to the present invention may be administered alone or in combination with other immunosuppressive agents.

In the specific Example of the present invention, the quantification of interleukin-2 secreted from T cells revealed that the level of interleukin-2 obtained from T cells activated with CD3/CD28 after treatment with the compound was significantly lower than that from the control group, indicating immunosuppressive activity of the compound.

Further, the pharmaceutical composition may further comprise pharmaceutically acceptable carrier.

As used herein, the term 'pharmaceutically acceptable carrier' refers to a pharmaceutically-acceptable material, composition or vehicle, such as a liquid or solid filler, diluent, excipient, solvent or encapsulating material, involved in carrying or transporting any subject composition or component thereof from one organ or portion of the body, to another organ or portion of the body. For administration, the composition of the present invention may further comprise a pharmaceutically acceptable carrier, excipient, or diluent, in addition to the above described active ingredients. Examples of the carriers, excipients and diluents include lactose, dextrose, sucrose, sorbitol, mannitol, xylitol, erythritol, maltitol, starch, arabic gum, alginate, gelatin, calcium phosphate, calcium silicate, cellulose, methyl cellulose, microcrystalline cellulose, polyvinyl pyrrolidine, water, methylhydroxybenzoate, propylhydroxybenzoate, talc, magnesium stearate, and mineral oil.

Further, according to the ordinary method, the composition of the present invention may be formulated for oral administration in the form of powders, granules, tablets, capsules, suspensions, emulsions, syrups or aerosols, or formulated in a form suitable for topical application, suppositories or sterile injectable solutions. In detail, a formulation may be prepared with generally used diluents or excipients, such as fillers, thickeners, binders, humectants, disintegrators and surfactants. Solid formulations for oral administration may include tablets, pills, powders, granules and capsules, but are not limited thereto. These solid formulations may be prepared by mixing the compound of Formula 1 with one or more excipients, such as starch, calcium carbonate, sucrose, lactose and gelatin. Also, the solid formulations may include, in addition to a simple excipient, a lubricant such as magnesium stearate or talc. Liquid formulations for oral administration may include suspensions, internal solutions, emulsions and syrups, but are not limited thereto. The liquid formulations may include, in addition to commonly used simple diluents, such as water and liquid paraffin, various excipients, which are exemplified by humectants, sweeteners, aromatics and preservatives. Formulations for parenteral administration may include sterile aqueous solutions, non-aqueous solutions, suspensions, emulsions, lyophilized preparations, and suppositories. Non-aqueous solutions and suspensions may be prepared with propylene glycol, polyethylene glycol, vegetable oils such as olive oil, and injectable esters such as ethyl oleate. As a base for suppositories, WITEPSOL®, macrogol, TWEEN® 61, cacao oil, laurin oil and glycerinated gelatin may be used.

AS another aspect, the present invention provides a method for treating neurological diseases comprising administering the composition to a subject in need thereof.

The neurological disease, pharmaceutical composition and treatment are the same as described above.

The composition of the present invention may be administered via any of the common routes, as long as it is able to reach a desired tissue. Therefore, the composition of the present invention may be administered by topical, oral, parenteral, intranasal, intravenous, intramuscular, subcutaneous, ocular, or transdermal route, and may be formulated into a solution, a suspension, a tablet, a pill, a capsule, a sustained-releases formulation or the like. The preferred formulation is an injectable formulation. The composition may be given by subcutaneous, intramuscular, or intravenous injection.

The composition of the present invention may be administered in a therapeutically or prophylactically effective amount. The dose may differ depending on various factors such as disease type and severity, age, sex, mode of administration, target cell, degree of expression, etc., and may be easily determined by those of ordinary skill in the art.

As another aspect, the present invention provides a method for treating immune hypersensitivity disorders comprising administering the composition to a subject in need thereof.

The immune hypersensitivity disorders, pharmaceutical composition, administering and treatment are the same as described above.

As another aspect, the present invention provides a method for suppressing immune responses comprising administering the composition to a subject in need thereof.

The suppression of the immune response, pharmaceutical composition and administering are the same as described above.

As another aspect, the present invention provides a method for preparing a tacrolimus analogue using a *Streptomyces* sp. strain in which one or more enzymes selected from the group consisting of endogenous TcsA, TcsB, TcsC and TcsD are reduced. The tacrolimus analogues having an improved immunosuppressive effect, an improved neuroprotective effect, or improved immunosuppressive and neuroprotective effects may be produced by the method.

The TcsB, the *Streptomyces* sp. strain and the tacrolimus analogues are the same as described above.

In the present invention, comparison of the entire biosynthetic gene clusters of FK506 from three different strains with that of FK520 suggested that only four genes, tcsA, tcsB, tcsC and tcsD, are involved in the biosynthesis of the unique PKS extender unit of FK506, namely allylmalonyl-CoA. In addition, in-frame gene deletion, chemical complementation, and biochemical analyses revealed the detailed biosynthetic pathway for an atypical allylmalonyl PKS extender unit. To be specific, TcsA, TcsB, TcsC and TcsD are involved in the synthesis of allylmalonyl-CoA required for the synthesis of allyl group that is specifically positioned at C21 of tacrolimus. The detailed biosynthetic pathway identified in the present invention is shown as a schematic diagram in FIG. 3. Among the above four enzymes, TcsA acts as an acyltransferase and has ACP domain. The nucleotide sequence of tcsA and amino acid sequence of the TcsA are shown as SEQ ID No. 43 and 46, respectively. In addition, the TcsA may refer to the protein possessing the amino acid sequence of SEQ ID NO. 46, but also an amino acid sequence having a sequence homology of 70% or higher, preferably 80% or higher, more preferably 90% or higher, even more preferably 95% or higher, even much more preferably 98% or higher, and most preferably 99% or higher to the amino acid sequence of SEQ ID NO. 46. However, any protein can be used without limitation, as long as it has acyltransferase activity. In addition, if the protein with the above sequence homology has substantially the same or corresponding bioactivity as TcsA even the variants of the protein having a portion of amino acid sequence deleted, modified, substituted, or added may be included in the scope of the present invention.

The polynucleotide that encodes the TcsA may be preferably a polynucleotide represented by a nucleotide sequence of SEQ ID NO. 43, and also includes any nucleotide sequence having a sequence homology of 70% or higher, preferably 80% or higher, more preferably 90% or higher, much more preferably 95% or higher, and most preferably 98% or higher homology to the nucleotide sequence of SEQ ID NO. 1 without limitation, as long as it is able to substantially encode a protein having TcsA activity.

TcsC has a function of 2-Pentenoyl-ACP carboylase/reductase. The nucleotide sequence of tcsC and the amino acid sequence of TcsC are shown as SEQ ID No. 44 and 47, respectively. In addition, the TcsC may refer to the protein possessing the amino acid sequence of SEQ ID NO. 47, but also an amino acid sequence having a sequence homology of 70% or higher, preferably 80% or higher, more preferably 90% or higher, even more preferably 95% or higher, even much more preferably 98% or higher, and most preferably 99% or higher to the amino acid sequence of SEQ ID NO. 47. However, any protein can be used without limitation, as long as it has 2-Pentenoyl-ACP carboylase/reductase activity. In addition, if the protein with the above sequence homology has substantially the same or corresponding bioactivity as TcsC even the variants of the protein having a portion of amino acid sequence deleted, modified, substituted, or added may be included in the scope of the present invention.

The polynucleotide that encodes the TcsC may be preferably a polynucleotide represented by a nucleotide sequence of SEQ ID NO. 44, and also includes any nucleotide sequence having a sequence homology of 70% or higher, preferably 80% or higher, more preferably 90% or higher, much more preferably 95% or higher, and most preferably 98% or higher homology to the nucleotide sequence of SEQ ID NO. 1 without limitation, as long as it is able to substantially encode a protein having TcsC activity.

Lastly, TcsD has a function of acyl-ACP dehydrogenase. The nucleotide sequence of tcsD and the amino acid sequence of the TcsD are shown as SEQ ID No. 45 and 48, respectively. In addition, the TcsD may refer to the protein possessing the amino acid sequence of SEQ ID NO. 48, but also an amino acid sequence having a sequence homology of 70% or higher, preferably 80% or higher, more preferably 90% or higher, even more preferably 95% or higher, even much more preferably 98% or higher, and most preferably 99% or higher to the amino acid sequence of SEQ ID NO. 48. However, any protein can be used without limitation, as long as it has acyl-ACP dehydrogenase activity. In addition, if the protein with the above sequence homology has substantially the same or corresponding bioactivity as TcsD even the variants of the protein having a portion of amino acid sequence deleted, modified, substituted, or added may be included in the scope of the present invention.

The polynucleotide that encodes the TcsD may be preferably a polynucleotide represented by a nucleotide sequence of SEQ ID NO. 45, and also includes any nucleotide sequence having a sequence homology of 70% or higher, preferably 80% or higher, more preferably 90% or higher, much more preferably 95% or higher, and most preferably 98% or higher homology to the nucleotide sequence of SEQ ID NO. 1 without limitation, as long as it is able to substantially encode a protein having TcsD activity.

In detail, the method of the present invention comprises (a) culturing the isolated modified *Streptomyces* sp. strain in which the activity of one or more enzymes selected from the group consisting of endogenous TcsA, TcsB, TcsC and TcsD are reduced; and (b) feeding carboxylic acids to the strain. Further, the above method may further comprise (c) the recovering of the tacrolimus analogue from the culture medium of the strain.

In the method of the present invention, the step (a) is the culturing of the isolated modified strain wherein the activity of one or more enzymes selected from the group consisting of TcsA, TcsB, TcsC and TcsD is reduced. The culturing condition is the same as described above.

The step (b) in the present invention is the step for feeding carboxylic acids to the strain to produce the tacrolimus analogues having altered C21 side chain. The modified strain cannot produce allylmalonyl-CoA, which is the extender unit of C21 ally side chain of FK506. Thus in order to produce tacrolimus analogues having altered C21 side chain, non-natural allyl side chain can be supplied to the strain instead of natural allyl side chain. The carboxylic acid is the same as described above.

In the specific Example of the present invention, the detail biosynthetic route generating the unique C21 allyl group in the FK506-producing *Streptomyces* sp. strain and the genes involved in the route, which are tcsA, tcsB, tcsC and tcsD, were investigated, and a mutant having the gene deletion was manufactured to prepare novel C21 side chain-modified FK506 analogs by mutasynthesis, and their biological activities were evaluated. It was also confirmed that a variety of FK506 analogues can be effectively produced by the mutasynthesis.

MODE FOR INVENTION

Hereinafter, the present invention will be described in more detail with reference to Examples. However, these Examples are for illustrative purposes only, and the invention is not intended to be limited by these Examples.

Example 1

Preparation of Materials

Strain and Fermentation

In the present invention, biosynthetic gene clusters were obtained from FK506 and FK520-producing strains. The bacteria strains used in the present invention are FK506-producing *Streptomyces* sp. KCTC 11604BP, *Streptomyces kanamyceticus* KCTC 9225, and *Streptomyces* sp. ATCC 55098, and FK520-producing *Streptomyces hygroscopicus* var. *ascomyceticus* ATCC14891.

For the production of tacrolimus or analogs thereof, the above described strains, and mutants and transformants of the above strains described herein were cultured under the following fermentation conditions.

Spores of *Streptomyces* sp. KCTC 11604BP, its gene deletion mutants, and *Streptomyces kanamyceticus* KCTC 9225 were generated on ISP4 agar plates and a seed culture was prepared in R2YE broth. 50 miligrams of vegetative cells grown in the seed culture were inoculated into a 250-ml baffled flask containing 50 ml of R2YE medium and cultivated on an orbital shaker (set at 180 rpm) for 6 days at 28° C. *Streptomyces hygroscopicus* var. *ascomyceticus* ATCC 14891 was incubated in a baffled 50-ml flask containing 50 ml of SY medium and grown on an orbital shaker for 6 days at 30° C.

*Streptomyces lividans* TK24, which was used as a heterologous host for preparing recombinant TcsD, was grown in YEME liquid medium. *Escherichia coli* DH5α was used for routine subcloning, while *E. coli* BL21 (DE3) and *E. coli* BL21(DE3)pLysS (NOVAGEN®) were used as heterologous hosts for expression of recombinant TcsC and $ACP_{tcsA}$. *E. coli* ET12567/pUZ8002 was the nonmethylating plasmid donor strain for intergeneric conjugation with *Streptomyces* sp. KCTC 11604BP. The *E. coli* strains were grown in LB, SOB or SOC liquid medium. Ampicillin (100 μg/ml), apramycin (50 μg/ml), chloramphenicol (25 μg/ml), kanamycin (50 μg/ml), thiostrepton (25 μg/ml), and nalidixic acid (25 μg/ml) were selectively added to the growth media as required.

Chemicals

The structure and chemical synthesis of allylmalonyl-CoA, 2-pentenyl-CoA, 3-oxopentanoyl-SNAC, trans-2-pentenyl-SNAC, pentanoyl-SNAC, allylmalonyl-SNAC, propylmalonyl-SNAC, and 4-fluorocrotonic acid are shown in the following reaction schemes or can be found in Liu et al (Liu, Y.; Hazzard, C.; Eustaquio, A. S.; Reynolds, K. A.; Moore, B. S. J. Am. Chem. Soc. 2009, 131, 10376.).

[3-Oxopentanoyl-SNAC thioester]

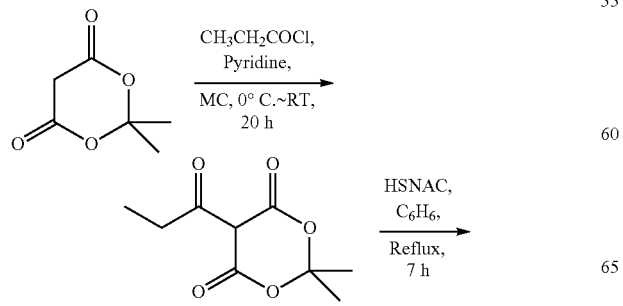

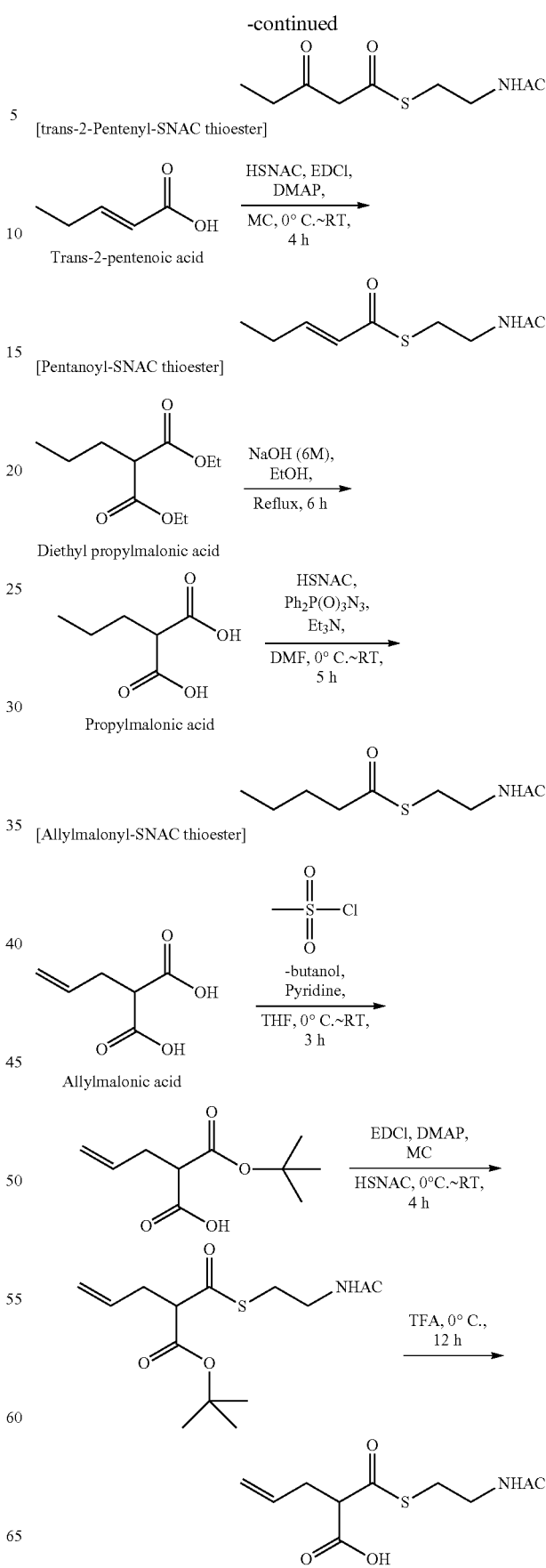

21

-continued

[Propylmalonyl-SNAC thioester]

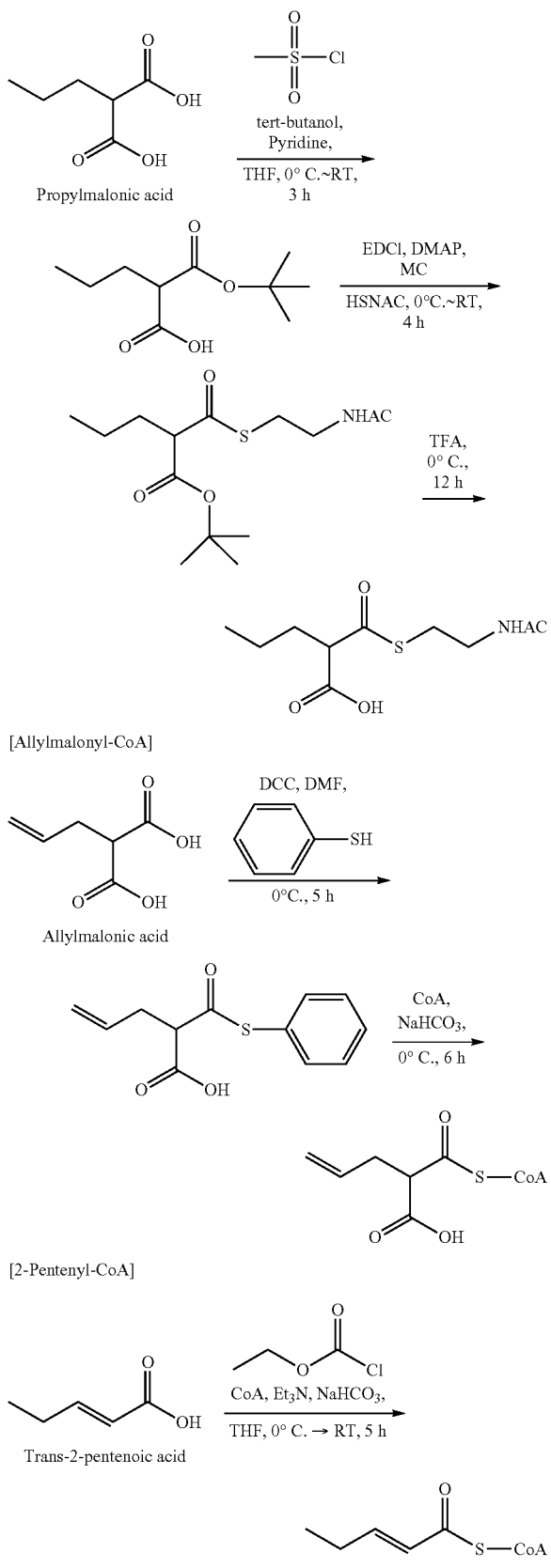

22

Example 2

Figure 2:
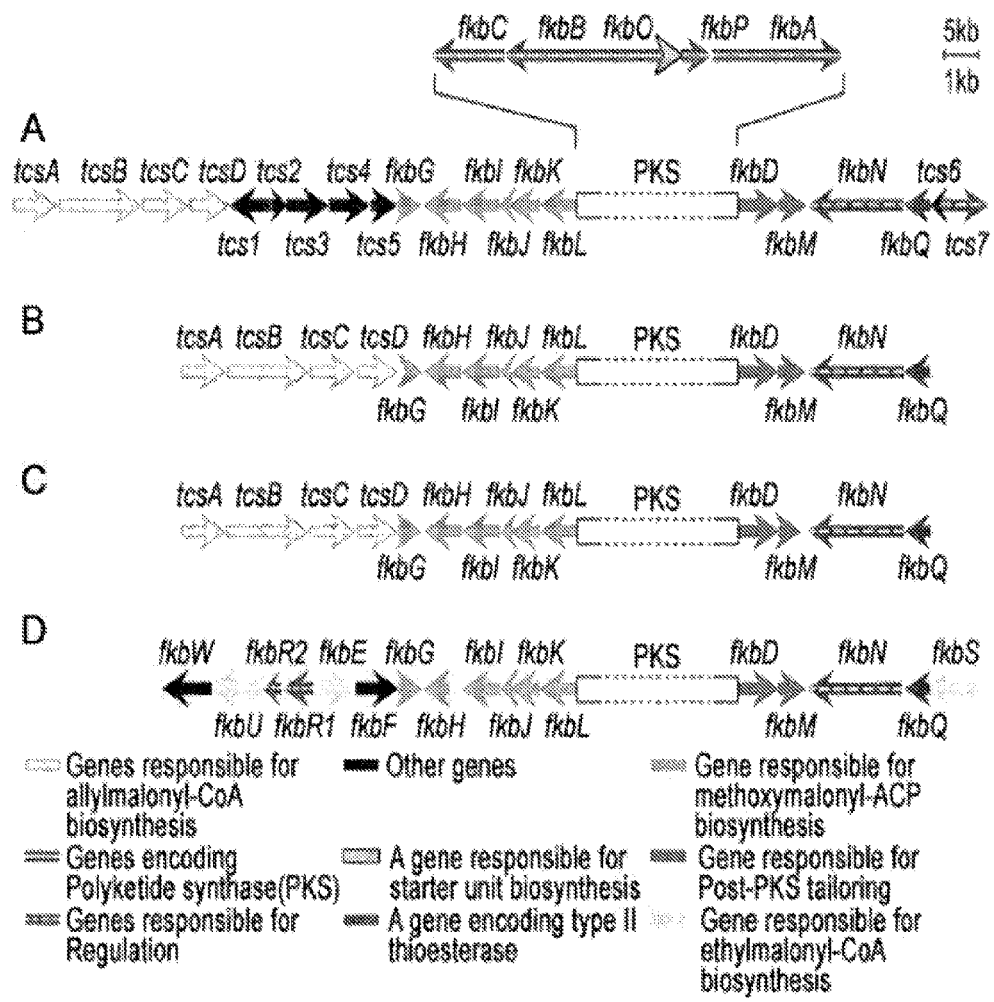
FIG. 2 shows organization of FK506 and FK520 biosynthetic gene clusters, in which (A) represents FK506 biosynthetic gene cluster from *Streptomyces* sp. KCTC 11604BP, (B) FK506 cluster from *Streptomyces* sp. ATCC55098 (MA6858), (C) FK506 cluster from *Streptomyces kanamyceticus* KCTC 9225, (D) FK520 cluster from *Streptomyces hygroscopicus* var. *ascomyceticus* ATCC14891, and based on comparison of their ORF array, four contiguous genes (tcsA, tcsB, tcsC and tcsD) are typically present in all FK506 clusters, but not in the FK520 cluster.

Analysis of FK506 Biosynthetic Gene Cluster and Biosynthetic Pathway of Allylmalonyl-CoA Analysis of FK506 Biosynthetic Gene Cluster Approximately 100 kb of the FK506 biosynthetic gene clusters and their flanking regions were sequenced from three FK506-producing strains, namely *Streptomyces* sp. ATCC 55098, *Streptomyces* sp. KCTC 9225, and *Streptomyces* sp. KCTC 11604BP. Analysis of these sequences revealed that fifteen genes are well maintained and identically organized in the FK520 and FK506 gene clusters (FIG. 2). The PKS and NRPS genes (fkbC, B, P and A), genes for methoxymalonyl-ACP biosynthesis (fkbG, H, I, J, K, and L) and a gene responsible for 4,5-dihydroxycyclohex-1-enecarboxylic acid (DHCHC) synthesis (fkbO), a 31-O-methyltransferase gene (fkbM), a C9 hydroxylase gene (fkbD), a regulatory gene (fkbN), and a type II thioesterase gene (fkbQ) are preserved among the clusters. The ethylmalonyl-CoA biosynthetic genes in the FK520 cluster (fkbE, S, and U) were not found in all of the FK506 clusters. A transcriptional regulator Tcs7, which belongs to the LysR-family, was located downstream of fkbQ only in *Streptomyces* sp. KCTC 11604BP strain.

A comparison of the FK506 clusters with that of FK520 revealed that four contiguous genes, tcsA, tcsB, tcsC, and tcsD, are commonly found in all FK506 clusters, suggesting that only these genes are involved in the biosynthesis of the unique allyl side chain of FK506. Five other genes (tcs1, tcs2, tcs3, tcs4, and tcs5) were found only in *Streptomyces* sp. KCTC 11604BP, and in-frame gene deletion experiments confirmed that neither none were involved in the biosynthesis of FK506. The genes upstream of tcsA and downstream of tcs7 in strain KCTC 11604BP strain do not have any obvious role in FK506 biosynthesis and are not conserved in all the sequenced FK506 clusters.

The products of tcsA and tcsB genes compose a distinct PKS system with noncanonical domain architecture. tcsA gene encodes an acyltransferase (AT) and an ACP domains, and tcsB codes for two unusual β-ketoacyl synthase (KS) domains similar to the uncharacterized PKS system of *Burkholderia* species. This unusual domain organization is analogous to the type II PKS priming system comprised of an initiating KS (KSIII), AT and ACP as reported in the biosynthetic gene clusters of doxorubicin, frenolicin, and R1128, but unique in that both AT and ACP domains are encoded by a single tcsA gene. TcsC shares >60% identity with crotonyl-CoA carboxylase/reductase which is shown to catalyze the reductive carboxylation of an enoyl-CoA ester in the ethylmalonyl-CoA pathway, suggesting that TcsC has a unique substrate specificity. TcsD is phylogenetically related to FkbI, an acyl-ACP dehydrogenase involved in the biosynthesis of methoxymalonyl-ACP of the FK520 gene cluster.

Analysis for Biosynthetic Pathway of Allylmalonyl-CoA

Figure 3:
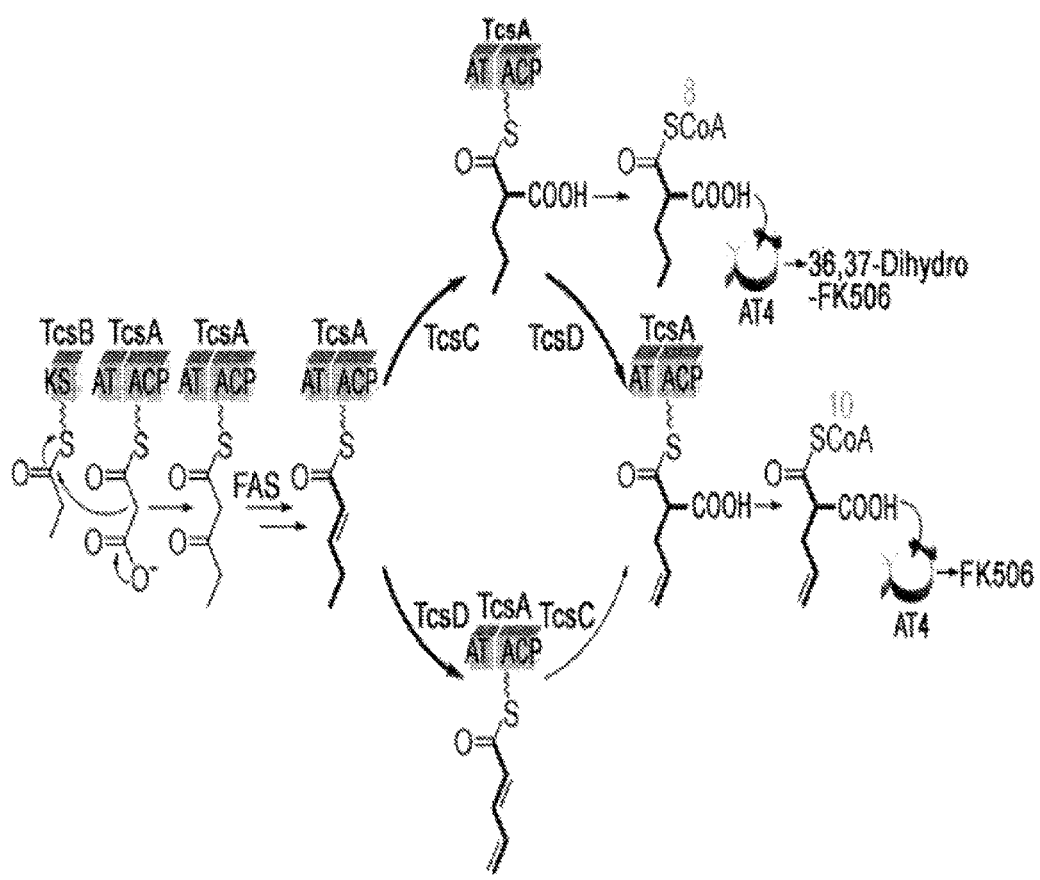
FIG. 3 shows a proposed biosynthetic pathway of allylmalonyl-CoA as a novel five-carbon extender unit for FK506 PKS, in which the functions of four proteins, TcsA, TcsB, TcsC and TcsD, are deduced as an acyl transferase (AT) and acyl carrier protein (ACP) complex, a β-keto acyl synthase (KS), a 2-pentenoyl-ACP carboxylase/reductase, and an acyl-ACP dehydrogenase, respectively, and bold lines indicate the biosynthetic steps characterized in vitro (8, propylmalonyl-CoA; 10, allylmalonyl-CoA)

It has been proposed that the five-carbon PKS extender unit, propylmalonyl-CoA, could be synthesized by reductive carboxylation of trans-2-pentenyl-CoA, which is likely to be derived from the β-oxidation of odd chain fatty acids. However, our discovery of a distinct PKS in the FK506 cluster strongly implies that the five-carbon extender unit in *Streptomyces* is PKS-derived, a finding that is consistent with a previous study showing that five carbons (C20, C21, C35, C36, and C37) of FK506 are derived from acetate and propionate (Byrne, K. M. et al. Dev. Ind. Microbiol. 32, (1993)). Based on the detailed sequence analysis of these four unique tcs genes as well as the gene deletion, chemical complementation, and biochemical experiments described later, it was proposed that the biosynthetic route to allylmalonyl-CoA is as shown in FIG. 3.

TcsB functions as a priming KS acylated by propionyl-CoA and catalyzes the condensation with malonate loaded on TcsA. The resulting ACP-tethered β-keto-pentanoate is converted into trans-2-pentenyl-ACP before the chain is further processed. Because no genes encoding β-keto processing enzymes, namely the ketoreductase and dehydratase, responsible for this reductive process were found in any of the sequenced FK506 clusters, it was hypothesized that these activities are shared with the FAS-like enzyme of the host, as is the case with type II PKS initiation modules. Indeed, SC01815, a FabG (the β-ketoacyl-ACP reductase of fatty acid biosynthesis) homolog from the genome of *Streptomyces coelicolor* A3 (2), was shown to function as the β-ketoacyl-ACP reductase component of the R1128 initiation module. The next reductive carboxylation reaction, giving propylmalonyl-ACP, is catalyzed by TcsC in a manner analogous to SalG. It was proposed that TcsD catalyzes the reaction to allylmalonyl-ACP, which is subsequently loaded onto module 4 of FK506 PKS through allylmalonyl-CoA. Alternatively, TcsD might convert trans-2-pentenyl-ACP to (2E)-2,4-pentadienyl-ACP, which in turn undergoes reductive carboxylation by TcsC to allylmalonyl-ACP. Skipping the TcsD-catalyzed dehydrogenation reaction would produce propylmalonyl-CoA. No gene encoding an ACP:CoA transacylase-like enzyme, which might be required for the conversion of propylmalonyl- and allylmalonyl-ACP to propylmalonyl-CoA and allylmalonyl-CoA, respectively, was located in the FK506 gene clusters.

Figure 5A:
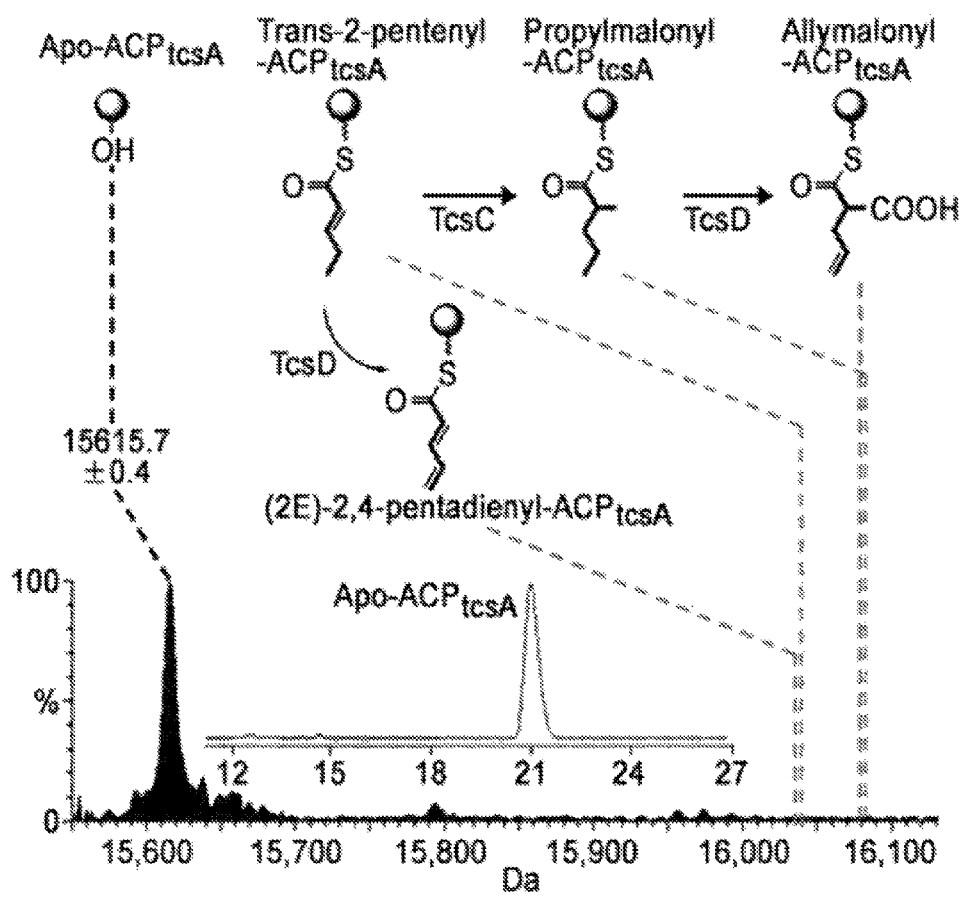
FIG. 5 shows ESI-MS spectra of the biosynthetic intermediates during allylmalonyl-$ACP_{tcsA}$ biosynthesis, in which the top of the figure illustrates acyl-$ACP_{tcsA}$ intermediates of interest, from left to right: apo-$ACP_{tcsA}$, trans-2-pentenyl-$ACP_{tcsA}$, (2E)-2,4-pentadienyl-$ACP_{tcsA}$, propylmalonyl-$ACP_{tcsA}$, and allylmalonyl-$ACP_{tcsA}$, each dashed line in the mass spectra indicates the five kinds of ACP-linked five-carbon units (see also FIG. 3); (A) Apo-$ACP_{tcsA}$ as a control (calculated mass: 15,615.85 Da, assuming the N-terminal methionine residue is removed), (B) Sfp-catalyzed reaction with trans-2-pentenyl-CoA and apo-$ACP_{tcsA}$. Trans-2-pentenyl-$ACP_{tcsA}$(calculated mass: 16,037.95 Da), (C) TcsC-catalyzed reaction with trans-2-pentenyl-$ACP_{tcsA}$. Propylmalonyl-$ACP_{tscA}$ (calculated mass: 16,083.98 Da), (D) TcsD-catalyzed reaction with propylmalonyl-$ACP_{tscA}$. Allymalonyl-$ACP_{tscA}$ (calculated mass: 16,081.78 Da), and (E) TcsD-catalyzed reaction with trans-2-pentenyl-ACP$_{tcsA}$. (2E)-2,4-pentadienyl-ACP$_{tcsA}$ (calculated mass: 16,035.75 Da)
Figure 5B:
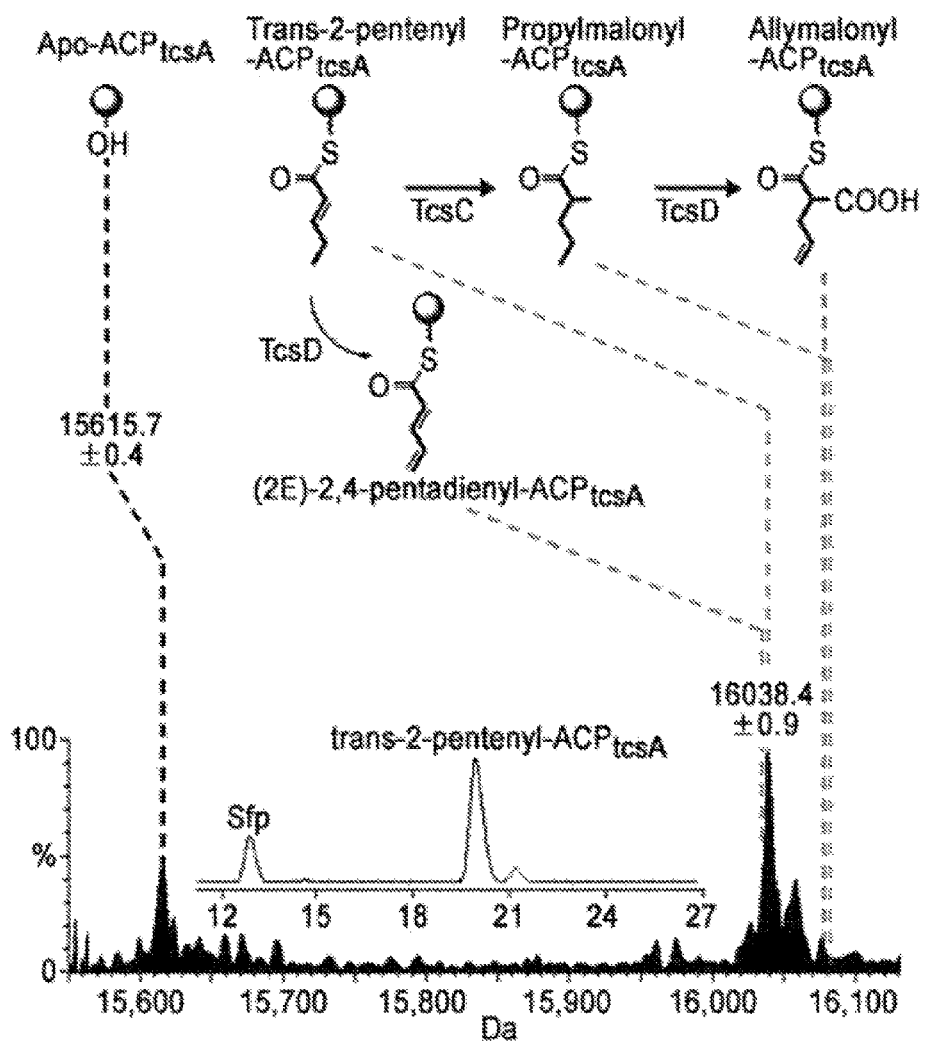
Figure 5C:
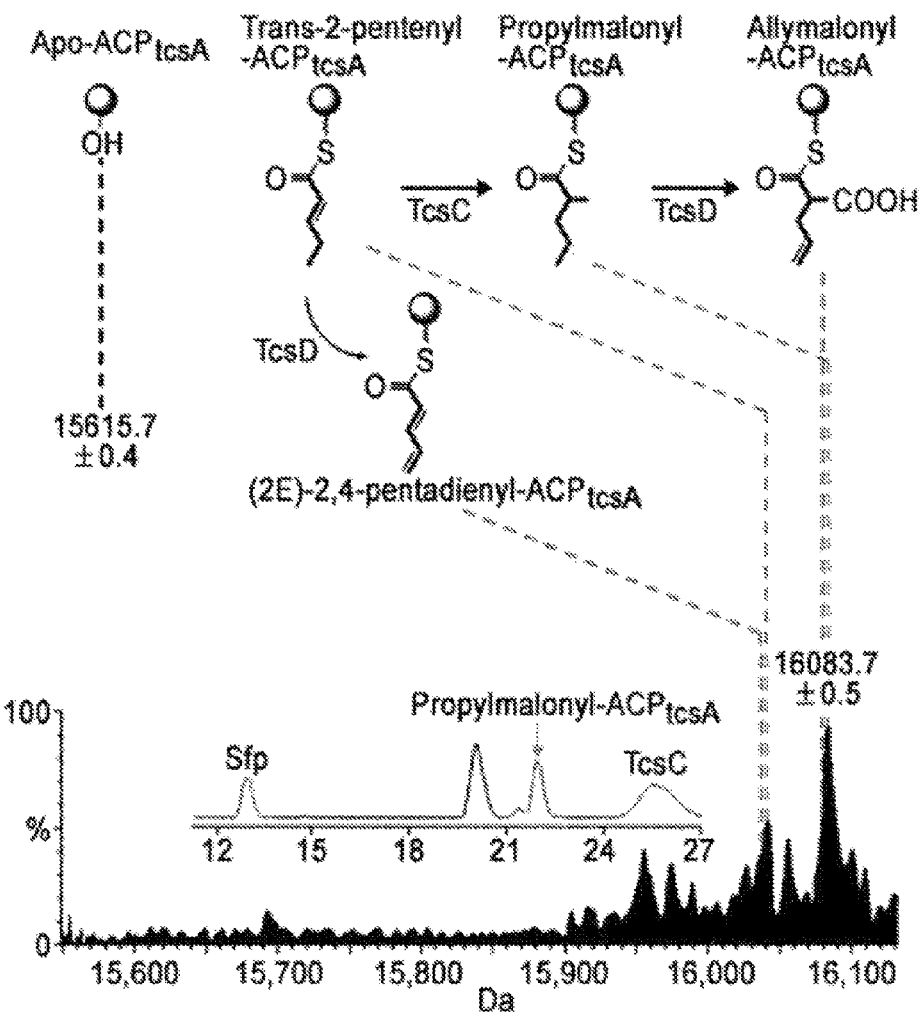
Figure 5D:
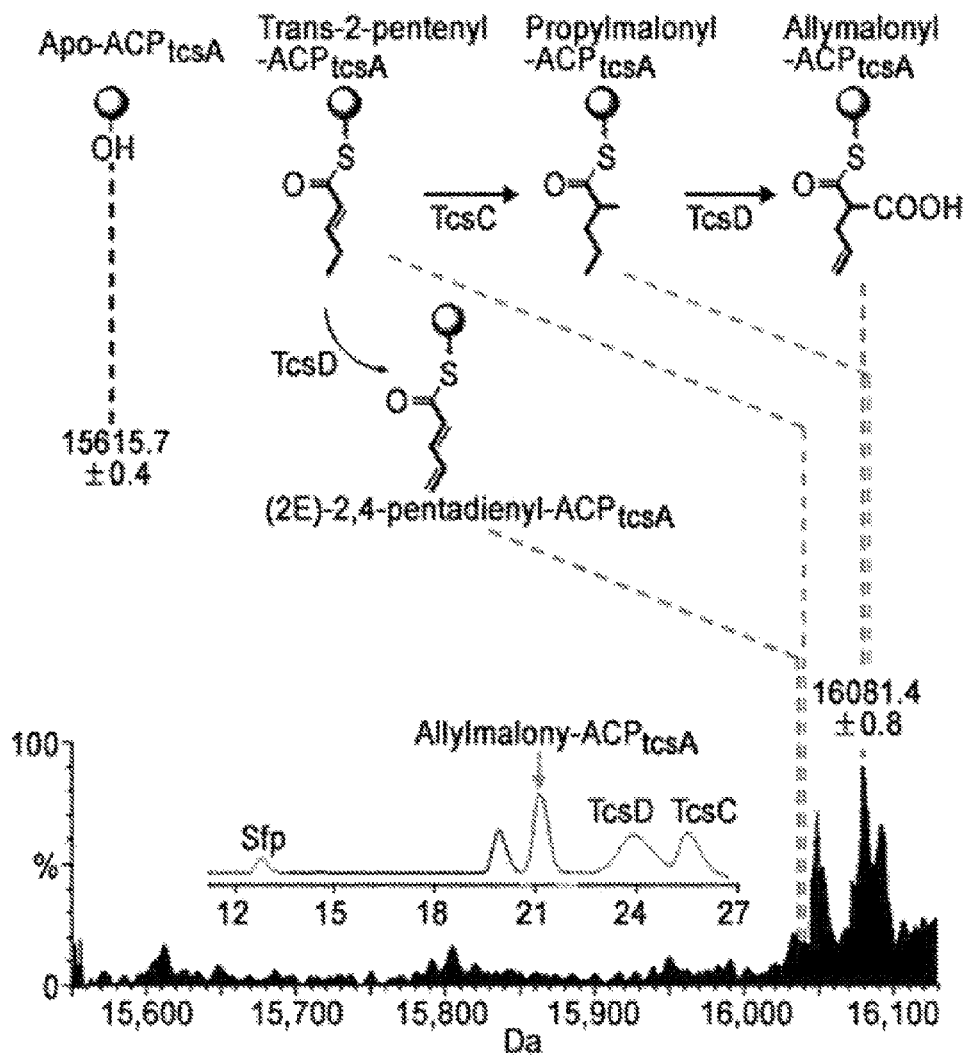
Figure 5E:
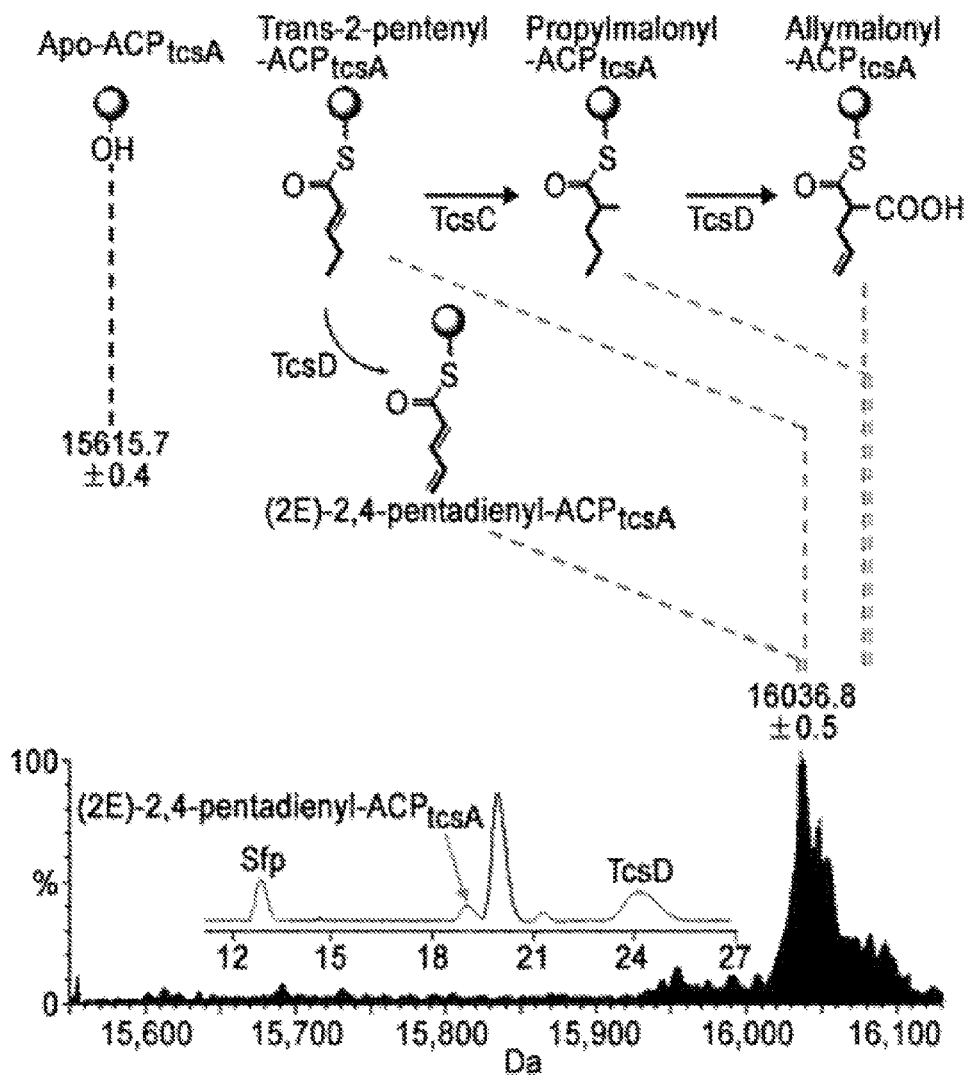

To demonstrate the precise roles of TcsC and TcsD, a biochemical and mass spectral approach was employed to reconstitute and measure allylmalonyl-ACP formation in vitro. The recombinant TcsC and ACP domain of TcsA ($ACP_{tcsA}$) were expressed in *E. coli* as histidine-tagged proteins and purified by nickel-affinity chromatography. Domain boundaries of $ACP_{tcsA}$ were chosen according to literature precedent. Soluble recombinant histidine tagged TcsD was instead obtained by expression in *Streptomyces lividans* TK24. On the basis of the in vivomutagenesis results, the most likely substrate for TcsC or TcsD is trans-2-pentenyl-$ACP_{tscA}$. By using the broad specificity phosphopantetheinyl transferase Sfp from *Bacillus subtilis* and chemically synthesized trans-2-pentenyl-CoA, apo-$ACP_{tcsA}$ was biochemically converted to trans-2-pentenyl-$ACP_{tcsA}$ (FIG. 5a, b). Upon incubation with TcsC, its NADPH-dependent reductive decarboxylation to propylmalonyl-$ACP_{tcsA}$ was measured by ESI-MS (FIG. 5c). A further FAD-dependent dehydrogenation reaction catalyzed by TcsD resulted in a subtle change in mass consistent with the formation of allylmalonyl-$ACP_{tcsA}$, a conclusion also supported by the observed shift in HPLC elution time (FIG. 5d). Alternatively, incubation of trans-2-pentenyl-$ACP_{tcsA}$ with TcsD generated a mass consistent with the formation of (2E)-2,4-pentadienyl-$ACP_{tcsA}$ at a low rate of conversion (FIG. 5e), which precluded it from being reacted with TcsC due to its low yield. These results suggest that the major biosynthetic pathway leading to allylmalonyl-ACP and thus allylmalonyl-CoA is through propylmalonyl-ACP (FIG. 3). Although the CoA thioesters, crotonyl-CoA and trans-2-pentenyl-CoA were also converted by TcsC to ethylmalonyl-CoA and propylmalonyl-CoA, respectively, the relatively low activity of TcsC toward crotonyl-CoA and trans-2-pentenyl-CoA compared with trans-2-pentenyl-$ACP_{tcsA}$ supports the deduced preference of TcsC for the ACP-linked substrate, although the absolute kinetic parameters for TcsC toward crotonyl-CoA, trans-2-pentenyl-CoA, and trans-2-pentenyl-$ACP_{tcsA}$ were not measured. The behavior of TcsC demonstrates an unprecedented example of a CCR-like carboxylase/reductase for ACP versus CoA-bound substrates. This preference for ACP-based substrates was also observed with TcsD (which did not accept trans-2-pentenyl-CoA as an alternative substrate).

Example 3

Construction of Plasmids and Mutants tcsgenes were inactivated in the FK506-producing strain *Streptomyces* sp. KCTC 11604BP by in-frame deletion via double cross-over homologous recombination. Details regarding DNA isolation and manipulation, and construction of plasmids for gene deletion and heterologous expression as well as the resulting mutant strains are described below.

Construction of in-Frame Gene Deletion Plasmids pGEM®-T Easy Vector (Promega) and Litmus28 (New England Biolabs) were used for routine subcloning. *E. coli*-*Streptomyces* shuttle vector pKC1139 was used for in-frame gene deletion. To delete nine tcs genes (tcsA, tcsB, tcsC, tcsD, tcs1, tcs2, tcs3, tcs4, and tcs5) and fkbA in *Streptomyces* sp. KCTC 11604BP, the construction of recombinant plasmids was carried out by PCR amplification of the left- and right flanking fragments from fosmid (fos1004F01) DNA derived from *Streptomyces* sp. KCTC 11604BP. One gene was targeted in each reaction. The primer pairs TcsALF/TcsALR, TcsBLF/TcsBLR, TcsCLF/TcsCLR, TcsDLF/TcsDLR, Tcs1LF/Tcs1LR, Tcs2LF/Tcs2LR, Tcs3LF/Tcs3LR, Tcs4LF/Tcs4LR, Tcs5LR/Tcs5LF, and FkbALF/FkbALR were designed for the amplification of left-flanking fragments of target genes, whereas TcsARF/TcsARR, TcsBRF/TcsBRR, TcsCRF/TcsCRR, TcsDRF/TcsDRR, Tcs1RF/Tcs1RR, Tcs2RF/Tcs2RR, Tcs3RF/Tcs3RR, Tcs4RF/Tcs4RR, Tcs5RR/Tcs5RF, and FkbARF/FkbARR were for right flanking fragments. A total of 20 PCR fragments were separately cloned in pGEM-T Easy vector and sequenced. After digestion with appropriate restriction enzymes, the fragments were cloned into pKC1139 digested with HindIII-EcoRI or HindIII-XbaI, to construct 10 different in-frame deletion plasmids: pΔTCSA, pΔTCSB, pΔTCSC, pΔTCSD, pΔTCS1, pΔTCS2, pΔTCS3, pΔTCS4, pΔTCS5 and pΔFKBA. Information regarding the strains, plasmids, and primers used in the present Example are described in the following Table. To construct tscB deletion mutant, tcsB gene was used and TcsBLF/TcsBLR and TcsBRF/TcsBRR primers were used.

```
TcsBLF:
                                   (SEQ ID NO. 2)
GACAAGCTTATGCTGGCGGTGAAGGCG(HindIII)

TcsBLR:
                                   (SEQ ID NO. 3)
CCGTCTAGACCAGAAGGAATCGAGCCGGAA(XbaI)

TcsBRF:
                                   (SEQ ID NO. 4)
CAGTCTAGAGTGATCCGTGCCCTGCACTCC(XbaI)

TcsBRR:
                                   (SEQ ID NO. 5)
GCCGAATTCGATGACGATGTCCGGGTCG(EcoRI)
```

TcsALF:
(SEQ ID NO. 6)
TTTAAGCTTCCGTCGGATCGGGGCGGCAG(HindIII)

TcsALR:
(SEQ ID NO. 7)
AAAGGATCCGAAGAGGAACGCCACCCCAC(BamHI)

TcsARF:
(SEQ ID NO. 8)
TTTAGATCTTGATCCGGTCGTGATCTCCC(BglII)

TcsARR:
(SEQ ID NO. 9)
AAAGAACTTCGTCGCCGGGCAGGTGCGC(EcoRI)

TcsCLF:
(SEQ ID NO. 10)
TTTAAGCTTAACAAGTCCCTGCTCGGTCA(HindIII)

TcsCLR:
(SEQ ID NO. 11)
AACGGATCCGTCTTCGACGGGGCTCCCGG(BamHI)

TcsCRF:
(SEQ ID NO. 12)
AAAAGATCTTCCCGGGTCTACCCCCTCGA(BglII)

TcsCRR:
(SEQ ID NO. 13)
TTTGAATTCCTCACCCAGGCCCTGACGC(EcoRI)

TcsDLF:
(SEQ ID NO. 14)
GCTAAGCTTCTCAGGCGTCTGCGGATGC(HindIII)

TcsDLR:
(SEQ ID NO. 15)
ATCGGATCCTTCGCTCACCGGGGCTGCC(BamHI)

TcsDRF:
(SEQ ID NO. 16)
AGCaAGATCTGGCATGTTCTGGTCAGTCC(Bg/II)

TcsDRR:
(SEQ ID NO. 17)
GTCGAATTCCATGCCACGAACGGGTCGA(EcoRI)

Tcs1LF:
(SEQ ID NO. 18)
TATAAGCTTACTCGTCGCACGCGGCAGC(HindIII)

Tcs1LR:
(SEQ ID NO. 19)
ATATCTAGACTCACCCAGGCCCTGACGC(XbaI)

Tcs1RF:
(SEQ ID NO. 20)
ATATCTAGACCAGTGATGCGAAGGCATG(XbaI)

Tcs1RR:
(SEQ ID NO. 21)
GACGAATTCCAGGAGGTTGACGGTGGTT(EcoRI)

Tcs2LF:
(SEQ ID NO. 22)
ATTAAGCTTGGGCGAACTCCTCGTTCG(HindIII)

Tcs2LR:
(SEQ ID NO. 23)
ATTTTTGGATCCCGCACGAGTCTCGGG(BamHI)

Tcs2RF:
(SEQ ID NO. 24)
GACGGATCCTCTGAATCGGAGATTCGT(BamHI)

Tcs2RR:
(SEQ ID NO. 25)
TTAGAATTCGTGGCCGTTGGAGATGAA(EcoRI)

Tcs3LF:
(SEQ ID NO. 26)
AGCAAGCTTAGTCCTCTGAGGAGCTGGTAG(HindIII)

Tcs3LR:
(SEQ ID NO. 27)
TCGAGATCTCACGAGGTCTCCTTGGAGACA(BglII)

Tcs3RF:
(SEQ ID NO. 28)
AAAGGATCCGTCATCATCGACCCGTAG(BamHI)

Tcs3RR:
(SEQ ID NO. 29)
TTTGAATTCTCCTTGCTGGTCTGGACG(EcoRI)

Tcs4LF:
(SEQ ID NO. 30)
TTTAAGCTTCGGCGTGGAGGCGTGGTCG(HindIII)

Tcs4LR:
(SEQ ID NO. 31)
AAAGGATCCCGTGAGGCCCTCGGCGACA(BamHI)

Tcs4RF:
(SEQ ID NO. 32)
AAAGGATCCGACGAGGTGGACTCCCACG(BamHI)

Tcs4RR:
(SEQ ID NO. 33)
TTTGAATTCCCAGCACCCTGTCGTCCCG(EcoRI)

Tcs5LF:
(SEQ ID NO. 34)
CCGAAGCTTACAGCACGGGGATACTCTG(HindIII)

Tcs5LR:
(SEQ ID NO. 35)
GGATCTAGACAGCCGTTCGGCGATCGCG(XbaI)

Tcs5RF:
(SEQ ID NO. 36)
AAATCTAGAATGCGCTGACGCGGCCCCG(XbaI)

Tcs5RR:
(SEQ ID NO. 37)
TTTGGATCCACGGTCGACTCACGCCGCC(BamHI)

FkbALF:
(SEQ ID NO. 38)
GTTACCAAGCTTGTACCGAGGACCACGTAC(HindIII)

FkbALR:
(SEQ ID NO. 39)
GAATCCGGATCCGACCGT TTTGTCCTGTTC(BamHI)

FkbARF:
(SEQ ID NO. 40)
TTTACCGGATTCTTCACCGGCTCCACCGAT(BamHI)

FkbARR:
(SEQ ID NO. 41)
GGGTCCTCTAGAAGAGAGTGTCGAGGAGATCG(XbaI)

TABLE 1

| Strain/vector | Relevant characteristics | Reference |
|---|---|---|
| Bacterial strains | | |
| *Escherichia coli* | | |
| DH5α | Host for general cloning | New England Biolabs |
| BL121(DE3) | Host for protein expression | Novagen |
| BL21(DE3)pLysS | Host for protein expression | Novagen |
| EPI300TM | Host for gene library construction | Epicentre Biotechnol. |
| ET12567/pUZ8002 | Donor strain for intergeneric conjugation between *E. coli* and *Streptomyces* | MacNeil, D. J. et al.[1] |
| BL21 (DE3)pLysS/pTCSA ACP | Strain for $ACP_{tcsA}$ protein expression | This study |
| BL21(DE3)/pTCSC | Strain for TcsC protein expression | This study |
| BL21(DE3)pLysS/pSFP | Strain for Sfp (PPTase) protein expression | This study |
| *Streptomyces* | | |
| ATCC 55098 (MA6858) | Wild-type FK506 (1)-producing strain | Motamedi, H. et al.[2] |
| KCTC 11604BP | Wild-type 1-producing strain | This study |
| KCTC 9225 | Wild-type 1-producing strain | Muramatsu, H. et al.[3] |
| ATCC 14891 | Wild-type FK520 (2)-producing strain | Wu. K. et al.[4] |
| ΔtcsA | Mutant of KCTC 11604BP with an in-frame deletion of tcsA, produces 2 & FK523 (21) | This study |
| ΔtcsB | Mutant of KCTC 11604BP with an in-frame deletion of tcsB, produces 2 & 21 | This study |
| ΔtcsC | Mutant of KCTC 11604BP with an in-frame deletion of tcsC, produces 2 & 21 | This study |
| ΔtcsD | Mutant of KCTC 11604BP with an in-frame deletion of tcsD, produces 2 & dihydro-FK506 (27) | This study |
| Δtcs1 | Mutant of KCTC 11604BP with an in-frame deletion of tcs1, produces 1 & 2 | This study |
| Δtcs2 | Mutant of KCTC 11604BP with an in-frame deletion of tcs2, produces 1 & 2 | This study |
| Δtcs3 | Mutant of KCTC 11604BP with an in-frame deletion of tcs3, produces 1 & 2 | This study |
| Δtcs4 | Mutant of KCTC 11604BP with an in-frame deletion of tcs4, produces 1 & 2 | This study |
| Δtcs5 | Mutant of KCTC 11604BP with an in-frame deletion of tcs5, produces 1 & 2 | This study |
| ΔfkbA | Mutant of KCTC 11604BP with an in-frame deletion of fkbA, does not produce 1 or 2 | This study |
| *S. lividans* TK24 | Host for protein expression | Walczak, R. J. et al[5] |
| *S. lividans* TK24/pTCSD | TK24 mutant, expresses heterologous tcsD using pTCSD | This study |
| Plasmids | | |
| pCCFOS1 (fosmid) | Vector for genomic library construction | Epicentre Biotechnol. |
| Litmus 28 | Multi-purpose *E. coli* cloning vector | New England Biolabs |
| pGEM-Teasy | PCR fragment cloning vector | Promega |
| pKC1139 | High-copy-number temperature-sensitive *E. coli*-*Streptomyces* shuttle vector | Bierman, M. et al.[6] |
| pET15b, pET28a | *E. coli* protein expression vector | Novagen |
| pGF101 | Sfp expression plasmid based on pET30a(+) | Zhou, P. et al.[7] |
| pSE34 | pWHM3 with $P_{ermE}$* promoter | Yoon, Y. J. et al.[8] |
| pΔTCSA | Deletion plasmid with in-frame deletion of 1,287-bp internal tcsA fragment | This study |
| pΔTCSB | Deletion plasmid with in-frame deletion of 2,088-bp internal tcsB fragment | This study |
| pΔTCSC | Deletion plasmid with in-frame deletion of 1,041-bp internal tcsC fragment | This study |
| pΔTCSD | Deletion plasmid with in-frame deletion of 1,152-bp internal tcsD fragment | This study |
| pΔTCS1 | Deletion plasmid with in-frame deletion of 1,110-bp internal tcs1 fragment | This study |
| pΔTCS2 | Deletion plasmid with in-frame deletion of 171-bp internal tcs2 fragment | This study |
| pΔTCS3 | Deletion plasmid with in-frame deletion of 1,209-bp internal tcs3 fragment | This study |
| pΔTCS4 | Deletion plasmid with in-frame deletion of 864-bp internal tcs4 fragment | This study |
| pΔTCS5 | Deletion plasmid with in-frame deletion of 666-bp internal tcs5 fragment | This study |
| pΔFKBA | Deletion plasmid with in-frame deletion of 18,171-bp internal fkbA fragment | This study |
| pTCSC | N,C-terminal $His_6$-tagged TcsC expression plasmid based on pET28a(+) | This study |

TABLE 1-continued

| Strain/vector | Relevant characteristics | Reference |
|---|---|---|
| pTCSA-ACP | N-terminal His$_6$-tagged ACP$_{tcsA}$ expression plasmid based on pET15b(+) | This study |
| pSFP | N-terminal His$_6$-tagged Sfp expression plasmid based on pET15b(+) | This study |
| pTCSD1 | N-terminal His$_6$-tagged plasmid based on pET15b(+), contains tcsD ORF | This study |
| pTCSD | N-terminal His$_6$-tagged TcsD expression plasmid based on pSE34 | This study |
| Fosmid clones | | |
| From KCTC 11604BP | | |
| fos1004F01 | Fosmid clone, contains bases 1-40,366 of FK506 biosynthetic gene cluster | This study |
| fos1005D02 | Fosmid clone, contains bases 39,116-80,661 of FK506 biosynthetic gene cluster | This study |
| fos1006D05 | Fosmid clone, contains bases 58,172-97,743 of FK506 biosynthetic gene cluster | This study |
| From KCTC 9225 | | |
| fos1006G02 | Fosmid clone, contains bases 1-35,521 of FK506 biosynthetic gene cluster | This study |
| fos1012A09 | Fosmid clone, contains bases 31,026-67,758 of FK506 biosynthetic gene cluster | This study |
| fos1004E04 | Fosmid clone, contains bases 41,430-85,253 of FK506 biosynthetic gene cluster | This study |
| fos1010E10 | Fosmid clone, contains bases 76,978-111,990 of FK506 biosynthetic gene cluster | This study |
| From ATCC 55098 | | |
| fos1011B11 | Fosmid clone, contains bases 1-41,779 of FK506 biosynthetic gene cluster | This study |
| fos1010H09 | Fosmid clone, contains bases 9,843-44,811 of FK506 biosynthetic gene cluster | This study |
| fos1012B03 | Fosmid clone, contains bases 27,398-72,806 of FK506 biosynthetic gene cluster | This study |
| fos1001F05 | Fosmid clone, contains bases 59,900-95,979 of FK506 biosynthetic gene cluster | This study |

TABLE 2

| Primer | Sequence 5' to 3' (restriction site underlined) | Restriction enzyme |
|---|---|---|
| TcsALF | TTT<u>AAGCTT</u>CCGTCGGATCGGGGCGGCAG | HindIII |
| TcsALR | AAA<u>GGATCC</u>GAAGAGGAACGCCACCCCAC | BamHI |
| TcsARF | TTT<u>AGATCT</u>TGATCCGGTCGTGATCTCCC | BglII |
| TcsARR | AAA<u>GAATTC</u>GTCGCCGGGCAGGTGCGC | EcoRI |
| TcsBLF | GAC<u>AAGCTT</u>ATGCTGGCGGTGAAGGCG | HindIII |
| TcsBLR | CCG<u>TCTAGA</u>CCAGAAGGAATCGAGCCGGAA | XbaI |
| TcsBRF | CAG<u>TCTAGA</u>GTGATCCGTGCCCTGCACTCC | XbaI |
| TcsBRR | GCC<u>GAATTC</u>GATGACGATGTCCGGGTCG | EcoRI |
| TcsCLF | TTT<u>AAGCTT</u>AACAAGTCCCTGCTCGGTCA | HindIII |
| TcsCLR | AAC<u>GGATCC</u>GTCTTCGACGGGGCTCCCGG | BamHI |
| TcsCRF | AAA<u>AGATCT</u>TCCCGGGTCTACCCCCTCGA | BglII |
| TcsCRR | TTT<u>GAATTC</u>CTCACCCAGGCCCTGACGC | EcoRI |
| TcsDLF | GCT<u>AAGCTT</u>CTCAGGCGTCTGCGGATGC | HindIII |

TABLE 2-continued

| Primer | Sequence 5' to 3' (restriction site underlined) | Restriction enzyme |
| --- | --- | --- |
| TcsDLR | ATCGGATCCTTCGCTCACCGGGGCTGCC | BamII |
| TcsDRF | AGCAGATCTGGCATGTTCTGGTCAGTCC | BglII |
| TcsDRR | GTCGAATTCCATGCCACGAACGGGTCGA | EcoRI |
| Tcs1LF | TATAAGCTTACTCGTCGCACGCGGCAGC | HindIII |
| Tcs1LR | ATATCTAGACTCACCCAGGCCCTGACGC | XbaI |
| Tcs1RF | ATATCTAGACCAGTGATGCGAAGGCATG | XbaI |
| Tcs1RR | GACGAATTCCAGGAGGTTGACGGTGGTT | EcoRI |
| Tcs2LF | ATTAAGCTTGGGCGAACTCCTCGTTCG | HindIII |
| Tcs2LR | ATTTTTGGATCCCGCACGAGTCTCGGG | BamHI |
| Tcs2RF | GACGGATCCTCTGAATCGGAGATTCGT | BamHI |
| Tcs2RR | TTAGAATTCGTGGCCGTTGGAGATGAA | EcoRI |
| Tcs3LF | AGCAAGCTTAGTCCTCTGAGGAGCTGGTAG | HindIII |
| Tcs3LR | TCGAGATCTCACGAGGTCTCCTTGGAGACA | BglII |
| Tcs3RF | AAAGGATCCGTCATCATCGACCCGTAG | BamHI |
| Tcs3RR | TTTGAATTCTCCTTGCTGGTCTGGACG | EcoRI |
| Tcs4LF | TTTAAGCTTCGGCGTGGAGGCGTGGTCG | HindIII |
| Tcs4LR | AAAGGATCCCGTGAGGCCCTCGGCGACA | BamHI |
| Tcs4RF | AAAGGATCCGACGAGGTGGACTCCCACG | BamHI |
| Tcs4RR | TTTGAATTCCCAGCACCCTGTCGTCCCG | EcoRI |
| Tcs5LF | CCGAAGCTTACAGCACGGGGATACTCTG | HindIII |
| Tcs5LR | GGATCTAGACAGCCGTTCGGCGATCGCG | XbaI |
| Tcs5RF | AAATCTAGAATGCGCTGACGCGGCCCCG | XbaI |
| Tcs5RR | TTTGGATCCACGGTCGACTCACGCCGCC | BamHI |
| FkbDF | GAGCGGCACGGTS(C/G)GGY(C/T)TCG | For fosmid selection |
| FkbDR | CGGGCAGCATCTCGGACGG | For fosmid selection |
| FkbOF | TGGGCCCGCACCGN(A/C/G/T)CGACCTGTT | For fosmid selection |
| FkbOR | GGCGATGTTGTCCAGGGCGACN(A/C/G/T)TCGC | For fosmid selection |
| FkbALF | GTTACCAAGCTTGTACCGAGGACCACGTAC | HindIII |
| FkbALR | GAATCCGGATCCGACCGT TTTGTCCTGTTC | BamHI |
| FkbARF | TTTACCGGATTCTTCACCGGCTCCACCGAT | BamHI |
| FkbARR | GGGTCCTCTAGAAGAGAGTGTCGAGGAGATCG | XbaI |
| TcsCF | ATTAGGATCCATGACCCACGTTCGCGA | BamHI |
| TcsCR | TATATACTCGAGCCGGGGCTGCCCC | XhoI |
| TcsAF | CATATGACCAGTGGGGTGGCGTTC | NdeI |
| TcsAR | GGATCCTCACCGCCGCCCGGA | BamHI |
| SfpF | ATACATATGAAGATTTACGGAATTTATATGGACC | NdeI |
| SfpR | ATAGGA TCCTTATAAAAGCTCTTCGTACGA | BamHI |

TABLE 2-continued

| Primer | Sequence 5' to 3' (restriction site underlined) | Restriction enzyme |
| --- | --- | --- |
| TcsDF | TTAACC<u>CATATG</u>AGCGAATCCGAACGCC | NdeI |
| TcsDR | TATT<u>CTCGAG</u>CTAGGTACGTTTCGCG | XhoI |

Construction of Protein Expression Plasmids pET15b (NOVAGEN®) containing an N-terminal His$_6$-tag was used for the expression of recombinant ACP$_{tcsA}$ and Sfp (PPTase), whereas N,C-terminal His$_6$-tagged pET28a (NOVAGEN®) was used for TcsC. Amplification of tcsC was accomplished with the primers TcsCF and TcsCR. The PCR product was cloned into pET28a to generate pTCSC with an N, C-terminal His$_6$-tag. Amplification of the DNA fragments containing ACP$_{tcsA}$ domain in tcsA was accomplished with the primers TcsAF and TcsAR. The PCR product was cloned into pET15b to produce pTCSA-ACP with an N-terminal His$_6$-tag. The gene sfp encoding 4'-phosphopantetheinyl transferase (PPTase) from *Bacillus subtilis* was amplified by PCR from pGF101 using primers SfpF and SfpR. The PCR product was cloned into pET15b to generate pSFP with an N-terminal His$_6$-tag. Amplification of tcsD was performed using primers TcsDF and TcsDR. The PCR product was cloned into pET15b to generate pTCSD1 with an N-terminal His$_6$-tag. This plasmid was digested with XbaI and HindIII and then cloned into pSE34, yielding pTCSD.

Gene Deletion

The plasmids used for in-frame gene deletion are summarized in the above Table 1. They were introduced into *Streptomyces* sp. KCTC 11604BP by conjugation from ET12567/pUZ8002 and then target genes were deleted by homologous recombination. A strain in which a single crossover between deletion plasmid and the KCTC 11604BP chromosome had occurred was selected by cultivation of an apramycin-resistant transconjugant at 37° C. (the non-permissive temperature for the pSG5-based replicon) in the presence of apramycin. One such colony was then subjected to three rounds of propagation in the absence of selection at 30° C. to allow for the second crossover. The ten desired double crossover mutants, ΔtcsA, ΔtcsB, ΔtcsC, ΔtcsD, Δtcs1, Δtcs2, Δtcs3, Δtcs4, Δtcs5, and ΔfkbA, were selected by their apramycin-sensitive phenotype, then verified by PCR and selectively confirmed by Southern blot analysis. In addition, using the same in-frame gene deletion method, tcsB-deleted strain (ΔtcsB) was prepared by deleting tcsB in *Streptomyces kanamyceticus* KCTC9225. The ΔtcsB strain prepared in this Example was deposited at the Korean Collection for Type Cultures (KCTC) under the Budapest Treaty in Feb. 25, 2011 under Accession No. KCTC 11879BP.

Example 4

Chemical Complementation of tcsA, tcsB, tcsC, and tcsD Deletion Mutants

Figure 4:
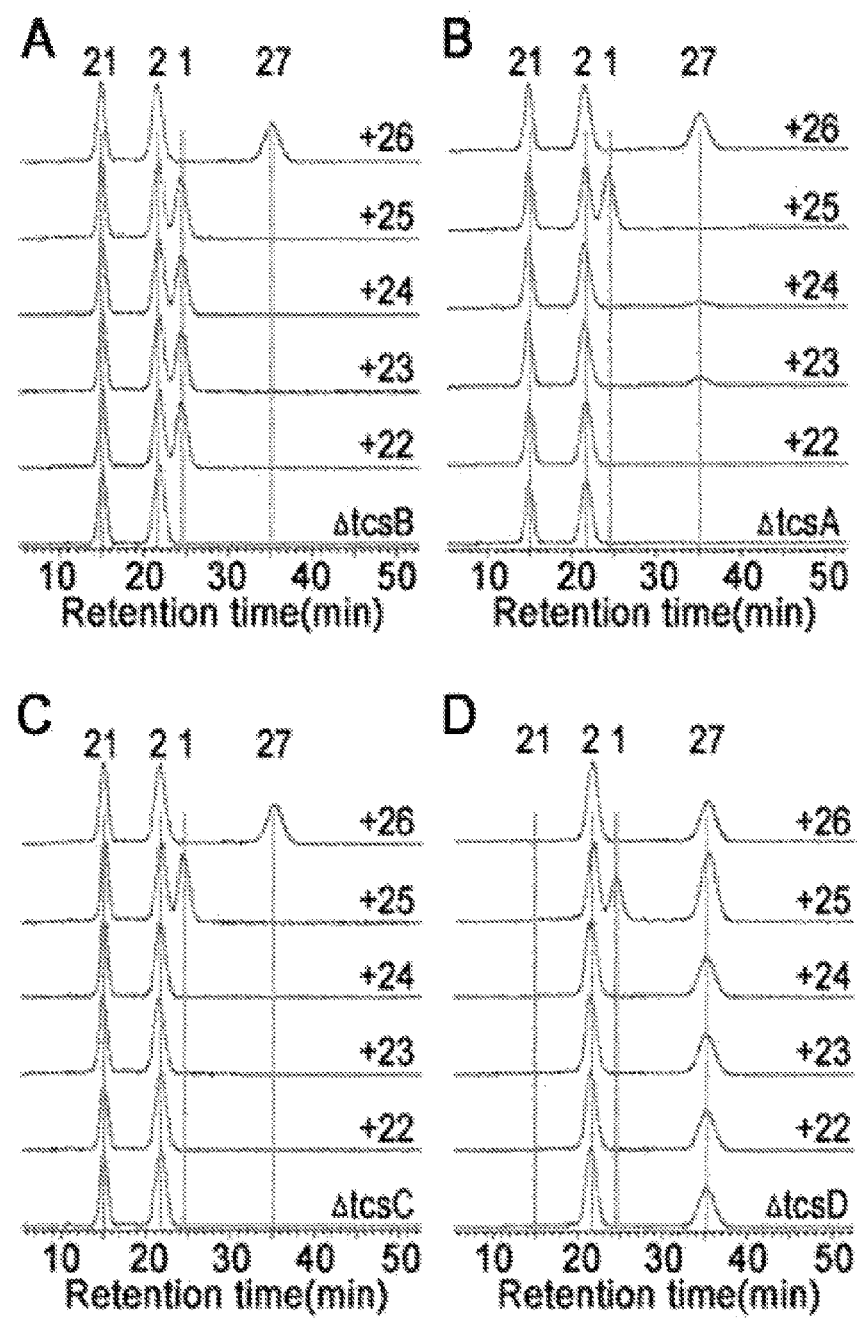
FIG. 4 shows chemical complementation of four different tcs deletion mutants with a variety of acyl-SNAC thioesters, in which chromatograms obtained from the culture of (A) tcsB deletion mutant (ΔtcsB strain), (B) tcsA deletion mutant (ΔtcsA strain), (C) tcsC deletion mutant (ΔtcsC strain), and (D) tcsD deletion mutant (ΔtcsD strain) are supplemented with one of the acyl-SNAC thioesters, 3-oxopentanoyl-SNAC (22), trans-2-pentenyl-SNAC (23), pentanoyl-SNAC (24), allylmalonyl-SNAC (25) or propylmalonyl-SNAC (26), and each vertical bluedotted line indicates the identity of one of the FK506 congeners (FK523 (21), FK520 (2), FK506 (1) or 36,37-dihydro-FK506 (27))

To obtain experimental evidence for the functions of tcsA, tcsB, tcsC, and tcsD in FK506 biosynthesis, each postulated gene in *Streptomyces* sp. KCTC 11604BP was inactivated by in-frame deletion. Synthetic acyl-N-acetylcysteamine thioesters (SNACs) that mimic the corresponding intermediates proposed in FIG. 3 were next fed to each deletion mutant to probe their effect on FK506 biosynthesis (FIG. 4).

The deletion of tcsB led to the selective loss of FK506 production in contrast to FK520, confirming the dedicated involvement of TcsB in the biosynthesis of FK506. It was also observed that the production of FK523 (35-desmethyl-FK520), which can be detected only in trace amounts in the wild-type strain by HPLC-ESI-MS/MS analysis, was significantly increased as a result of the misincorporation of methylmalonyl-CoA in the absence of the five-carbon extender unit. Supplementing two synthetic acyl-SNACs (3-oxopentanoyl-SNAC and trans-2-pentenyl-SNAC) restored FK506 production in the tcsB deletion mutant (ΔtcsB strain, KCTC 11879BP), probably after loading onto TcsA per the proposed pathway (FIG. 3). FK506 production was also restored by pentanoyl-SNAC, possibly via β-oxidation to trans-2-pentenyl-SNAC by acyl-CoA dehydrogenase. Lastly, restoration of FK506 biosynthesis by allylmalonyl-SNAC suggests that the in vivo extender unit is CoA-linked instead of ACP-linked. Although tcsD, which is responsible for the formation of the C36-C37 double bond of FK506, is intact in the ΔtcsB strain, propylmalonyl-SNAC supported the biosynthesis of only 36,37-dihydro-FK506 as determined by HPLC-ESI-MS/MS. This result suggests that the exogenously fed carboxylated SNAC thioester is not loaded onto the TcsA ACP domain, which is required for the desaturation activity of TcsD (FIG. 4a).

To confirm the incorporation of an intact five-carbon extender unit into the FK506 polyketide chain, [1-$^{13}$C] pentanoic acid was provided as a precursor to the ΔtcsB mutant. As anticipated, $^{13}$C NMR analysis of [1-$^{13}$C]pentanoic acid-enriched FK506 revealed the specific isotopic labeling of C20 at approximately 23% enrichment. C8 and C22, corresponding to the positions of incorporated acetate, were also labeled at a lower percentage of 8-15% presumably from the degradation of [1-$^{13}$C]pentanoic acid by β-oxidation. These acetate-derived carbons were also enriched in FK520 and FK523 purified from the same [1-$^{13}$C]pentanoic acid-fed ΔtcsB mutant.

The tcsA deletion mutant (ΔtcsA strain) also produced only FK520 and FK523. Because the 3-oxopentanoate moiety bound to ACP is believed to be processed to trans-2-pentenyl-ACP by the recruited FAS-like system (FIG. 3), 3-oxopentanoyl-SNAC did not restore FK506 production in the absence of TcsA as it did in the absence of TscB. Supplementation of the ΔtcsA strain with trans-2-pentenyl-SNAC and pentanoyl-SNAC resulted in the production of trace amounts of 36,37-dihydro-FK506, but no FK506 production, thereby supporting our previous observation that the dehydrogenase TcsD operates with the ACP bound substrate. Furthermore, this finding suggests that the reductive carboxylase TcsC also prefers ACP-linked substrates but can default operate with acyl-CoAs, which is typical of enzymes in this family. As expected, the addition of allylmalonyl-SNAC and propylmalonyl-SNAC produced FK506 and 36,37-dihydro-FK506, respectively (FIG. 4b).

To further explore the in vivo function of tcsC, this gene was inactivated which also resulted in the selective loss of FK506. Chemical complementation of the tcsC deletion mutant (ΔtcsC strain) with 3-oxopentanoyl-SNAC, trans-2-pentenyl-SNAC, and pentanoyl-SNAC did not restore production of FK506 or 36,37-dihydro-FK506, thereby confirming its central role in functionalizing the five-carbon extender unit by reductive carboxylation. Again, addition of the malonates, allylmalonyl-SNAC and propylmalonyl-SNAC yielded FK506 or 36,37-dihydro-FK506, respectively (FIG. 4c). The lack of FK506 production in the ΔtcsC strain fed with propylmalonyl-SNAC provides further support for the previous speculation that the TcsA ACP domain is not acylated with propylmalonyl-SNAC and that TcsD is an acyl-ACP dehydrogenase.

Lastly, the tcsD deletion mutant (ΔtcsD strain) produced FK520 and large amounts of 36,37-dihydro-FK506, thus confirming its central role in the formation of the C36/C37 olefin of FK506. While exogenous 3-oxopentanoyl-SNAC, trans-2-pentenyl-SNAC, pentanoyl-SNAC and propylmalonyl-SNAC did not change the production profile of the ΔtcsD strain, the addition of allylmalonyl-SNAC restored FK506 production (FIG. 4d). 36,37-dihydro-FK506 produced in both the ΔtcsB and ΔtcsC mutants by chemical complementation was not further transformed into FK506 despite the presence of tcsA and tcsD, indicating that the double bond of the C21 allyl group of FK506 is not generated through post-PKS modification. The above results suggest that TcsA, TcsB, TcsC, and TcsD are involved in the biosynthesis of the C21 allyl group of tacrolimus in the Streptomyces sp. strain producing tacrolimus, demonstrating that if one or more of the above enzymes has the reduced activity FK506 cannot be produced properly. Also, together with the results of Example 2, it is demonstrated that the TcsA functions as an acyltransferase while TcsB works as keto synthase. TcsC is 2-Pentenoyl-ACP carboylase/reductase and TcsD works as Acyl-ACP dehydrogenase. That is, allylmalonyl-CoA extender unit required for the synthesis of C21 allyl group of tacrolimus is synthesized by a successive action of the TcsA, TcsB, TcsC, and TcsD.

Example 5

Mutasynthesis of FK506 Analogues

Production of FK506 Analogues

The ΔtcsB mutant of Streptomyces sp. KCTC 11604BP was grown as described above. Trans-2-hexenoic acid, 4-methylpentanoic acid, and 4-fluorocrotonic acid were supplemented in 50-ml cultures at a final concentration of 10 mM.

Analysis of FK506 Analogues

FK506-related biosynthetic intermediates and their analogues, which were generated by FK506-producing Streptomyces sp. KCTC 11604BP, its deletion mutants, and deletion mutants supplemented with the SNAC thioesters (3-oxopentanoyl-SNAC, trans-2-pentenyl-SNAC, pentanoyl-SNAC, allylmalonyl-SNAC, and propylmalonyl-SNAC) and a series of carboxylic acids, as well as Streptomyces hygroscopicus var. ascomyceticus ATCC 14891, were extracted with EtOAc from the fermentation broth, then analyzed by HPLC-ESI-MS/MS. Samples were separated on an ACQUITY UPLCTh BEH $C_{18}$ column (50×2.1 mm, 1.7 μm; Waters) interfaced with a Waters/Micromass Quattro micro/MS instrument tracing by MS/MS using a gradient of MeCN at a flow rate of 0.2 ml/min over 50 min starting with 40% (v/v) aqueous MeCN containing 10 mM ammonium acetate and 0.1% acetic acid. Tracing was done by MS/MS operated in multiple reactions monitoring mode choosing mass pairs specific for the selected analytes to detect the transition from parent ion as an ammonium adduct to product ion. Three separate cultivations and independent extractions were performed.

Since the biosynthesis of FK506 analogs is more efficient in the absence of competition from the natural extender unit, a series of carboxylic acids, including 4-halocrotonic acids, branched/4-halobutanoic acids, branched/unsaturated/5-halopentanoic acids, branched/unsaturated hexanoic acids, and heptanoic acid, were fed to the ΔtcsB strain. New metabolites were produced by feeding trans-2-hexenoic acid, 4-methylpentanoic acid, and 4-fluorocrotonic acid resulting in 36,37-dihydro-37-methyl-FK506, 36-methyl-FK506, and 36-fluoro-FK520, respectively (FIG. 6). Novel analogs, 36-methyl-FK506 and 36-fluoro-FK520 were confirmed here by NMR (FIGS. 9 to 22).

Example 6

Analysis of Biological Activities of FK506 Analogues

In Vitro T-Cell Activation Assay

Figure 7:
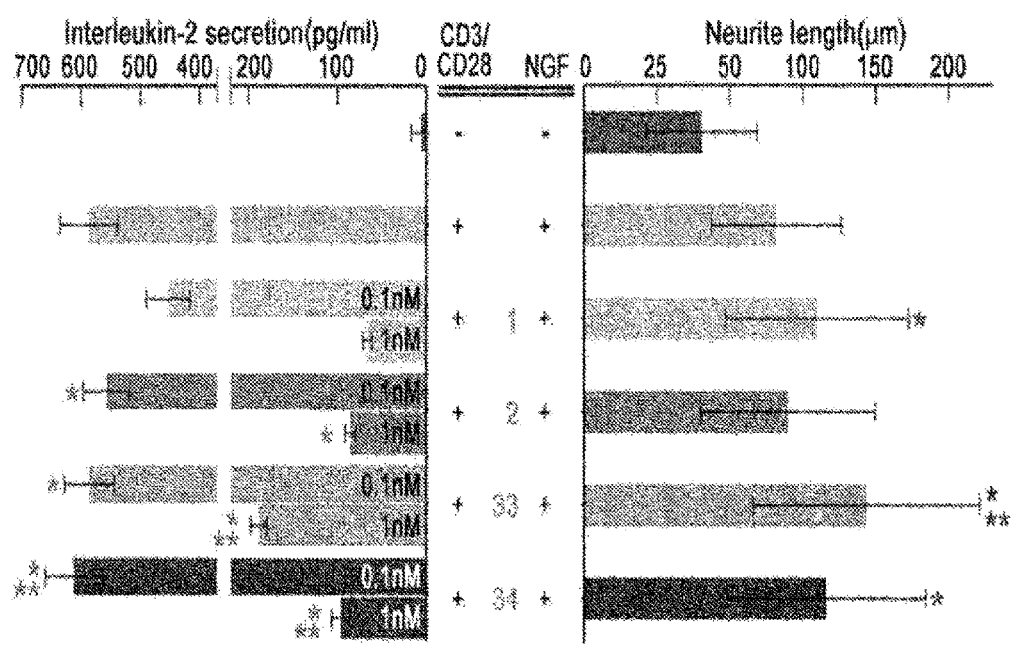
FIG. 7 shows immunosuppressive and neurite outgrowth activities of the FK506 analogues, in which immunosuppressive properties of two FK506 analogues, methyl-FK506 (33) and 36-fluoro-FK520 (34), were compared with those of authentic FK506 (1) and FK520 (2) by quantification of interleukin (IL)-2 secreted from CD3/CD28-stimulated human T lymphocytes (left horizontal bar graph), each bar indicates the result of cell culture in the absence (red) or presence (orange) of CD3/CD28 antibodies, in addition to FK506 (dark yellow), FK520 (green), methyl-FK506 (dark cyan) or 36-fluoro-FK520 (blue) at two different concentrations (0.1 and 1 nM) (*$P<0.001$ as compared with FK506-treated samples at the same concentration; **$P<0.001$ as compared with FK520-treated samples at the identical concentration), nerve regenerative properties of the FK506 analogues, 36-methyl-FK506 (33) and 36-fluoro-FK520 (34) were compared with those of FK506 (1) and FK520 (2) by measuring the neurite lengths of the nerve growth factor (NGF)-activated human neuroblastoma cell line SH-SY5Y (right horizontal bar graph), and each bar indicates the result of cell culture in the absence (red) or presence (orange) of NGF, in addition to 1 nM of FK506 (dark yellow), FK520 (green), methyl-FK506 (dark cyan) or 36-fluoro-FK520 (blue) (*$P<0.001$ as compared with NGF-treated samples; **$P<0.001$ as compared with 1-treated samples)

The relative immunosuppressive properties of the mutasynthetic analogues, 36-methyl-FK506 and 36-fluoro-FK520, compared with authentic FK506 and FK520, were determined using T lymphocytes. In brief, human T-cells ($1 \times 10^6$ cells/well) were activated with CD3/CD28 antibodies (BD Pharmingen; 0.5 μg/ml for each), then treated with two different concentrations (0.1 and 1.0 nM) of FK506, FK520, 6-methyl-FK506 and 36-fluoro-FK520 for 16 to 20 hr. After removal of cell debris by routine centrifugation, the supernatant was subjected to ELISA (R&D Systems) to quantify the level of interleukin-2 secreted from activated T-cells. The level of interleukin-2 obtained from T cells activated with CD3/CD28 without further treatment with the above compounds was used as a control (FIG. 7). Evaluation of interleukin-2 (IL-2) secretion from activated human T lymphocytes treated with FK506, FK520, 36-methyl-FK506 and 36-fluoro-FK520 showed that the in vitro immunosuppressive activity of 36-methyl-FK506 was not improved against FK506 and FK520, but showed a significant immunosuppressive activity as compared with the control group (FIG. 7).

The above results demonstrate that the novel tacrolimus analogues of the present invention, i.e. 36-methyl-FK506 and 36-fluoro-FK520 have the immunosuppressive activity, suggesting that the composition comprising the above analogues can be used for suppressing the immune response and furthermore for the prevention or treatment of the diseases associated with the immune hypersensitivity.

In Vitro Neurite Outgrowth Assay Using Human Neuroblastoma Cells.

Figure 8:
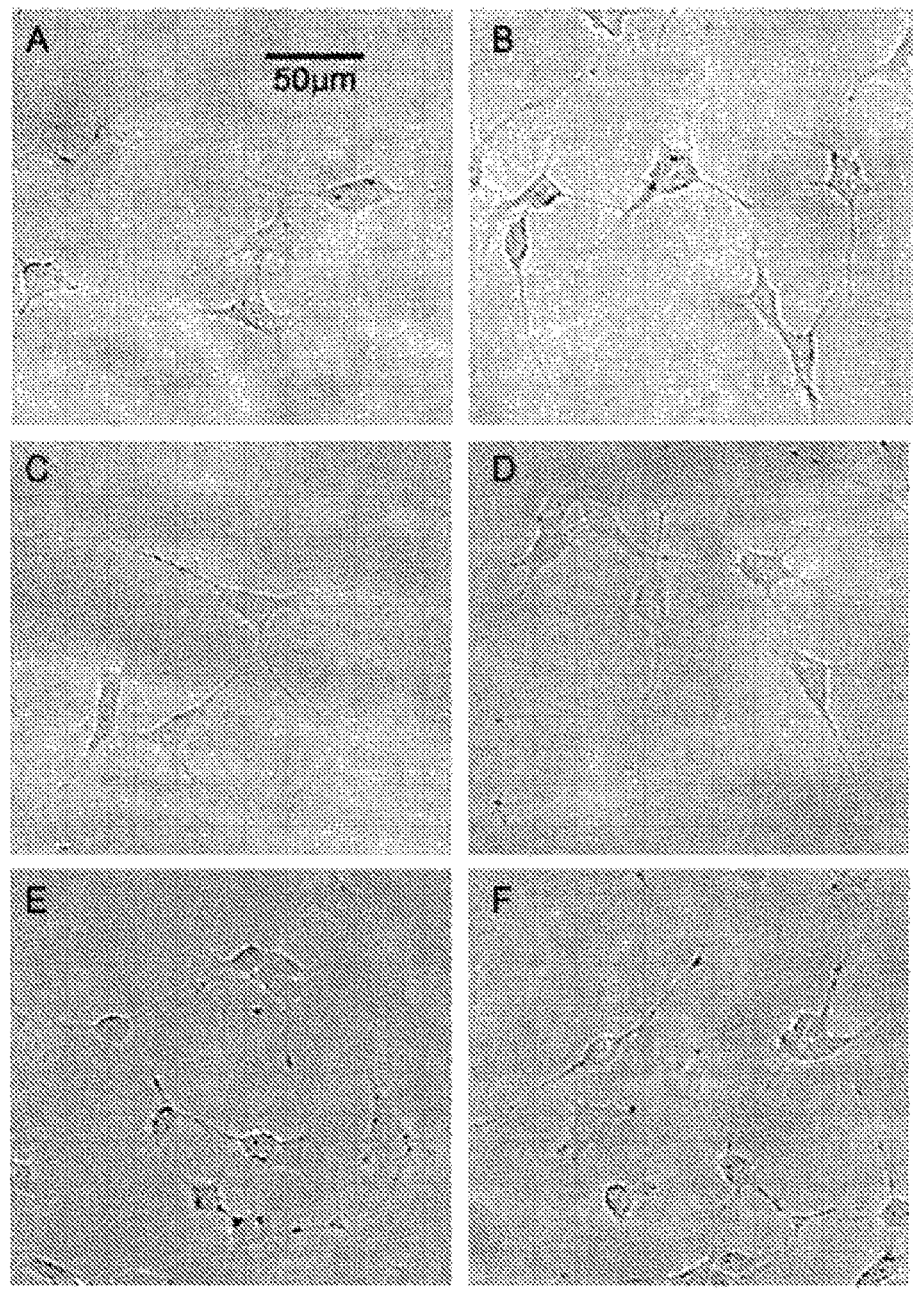
FIG. 8 shows representative micrographs of neurite outgrowth activities of the FK506 analogues in SH-SY5Y neuroblastoma cells, in which untreated cells (A), cells treated with NGF alone (B), and cells treated with NGF in the presence of FK506 (C), FK520 (D), 36-methyl-FK506 (E) and 36-fluoro-FK520 (F) at a concentration of 1 nM after 96 h of cultivation, and neurite processes are longer in treated cells, with the exception of those treated with FK520 (D), compared with those treated with NGF alone (B)
Figure 9A:
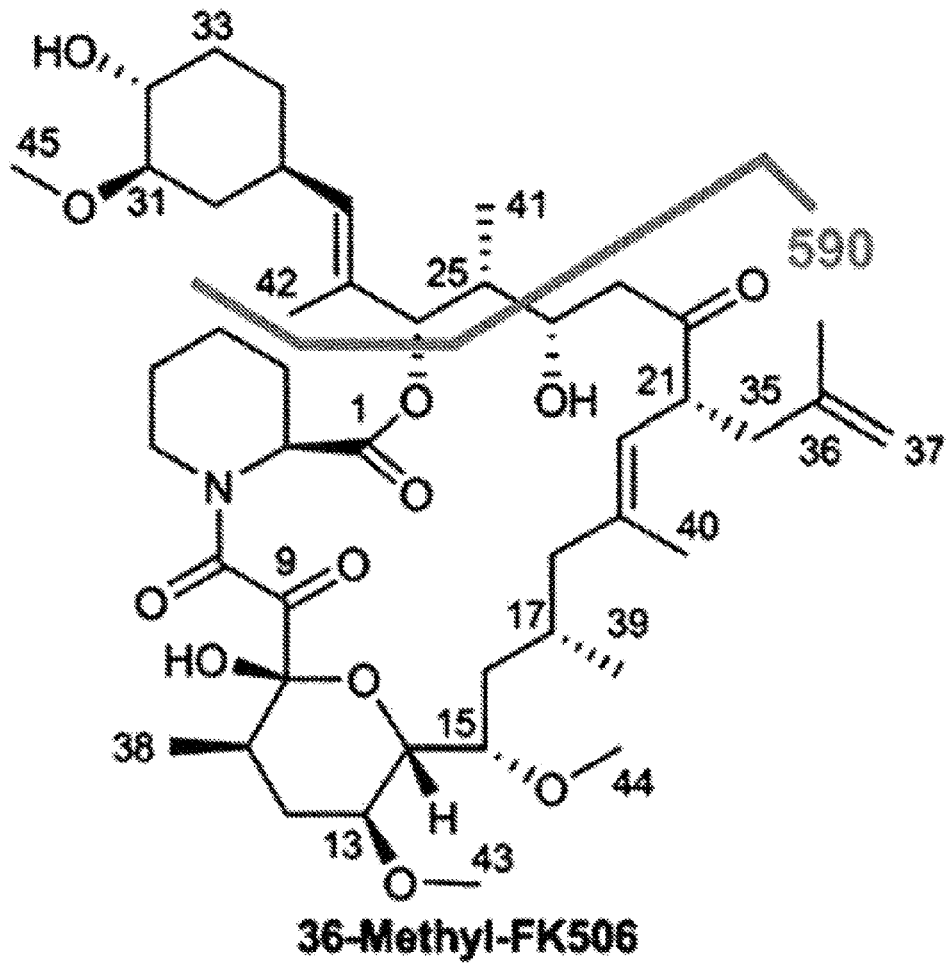
FIG. 9 shows ESI-MS/MS analysis of a novel FK506 analogue, 36-methyl-FK506 obtained from the tcsB deletion mutant of Streptomyces sp. KCTC 11604BP (ΔtcsB strain) supplemented with 4-methylpentanoic acid, in which (A) ESI-MS/MS fragmentation pattern of 36-methyl-FK506, and (B) MS/MS spectra of 36-methyl-FK506.
Figure 9B:
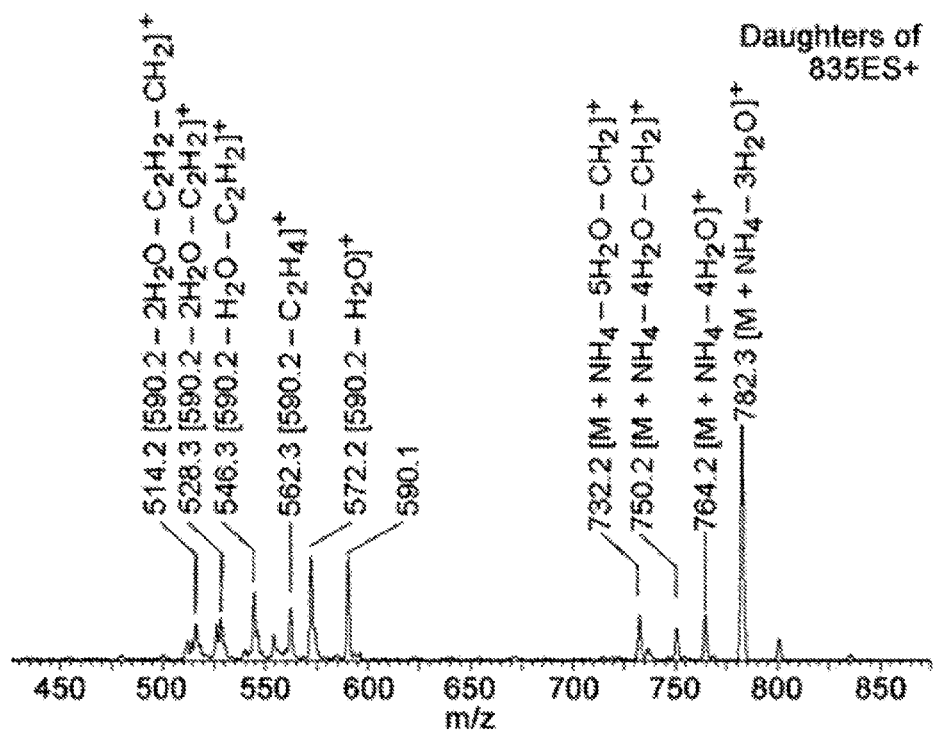
Figure 10:
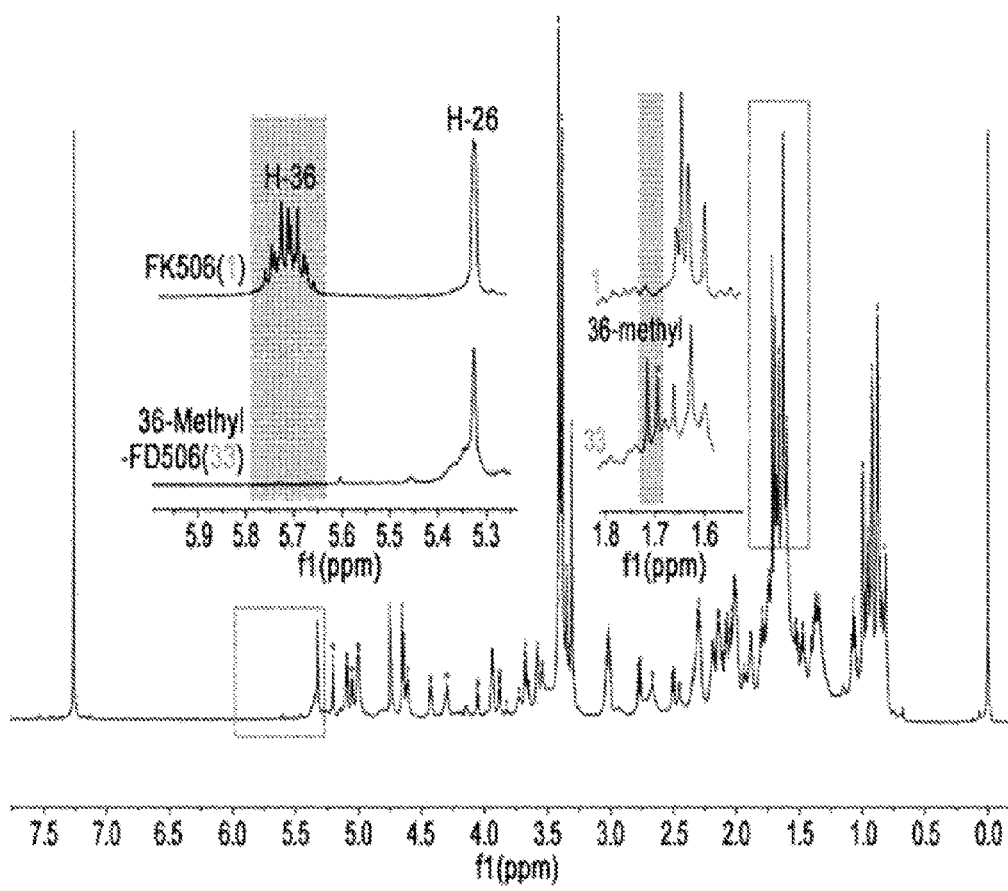
FIG. 10 shows $^1$H NMR (900 MHz, CDCl$_3$) spectrum of 36-methyl-FK506, in which '*' indicates the coexistence of tautomer (1, FK506; 33, 36-methyl-FK506)
Figure 11:
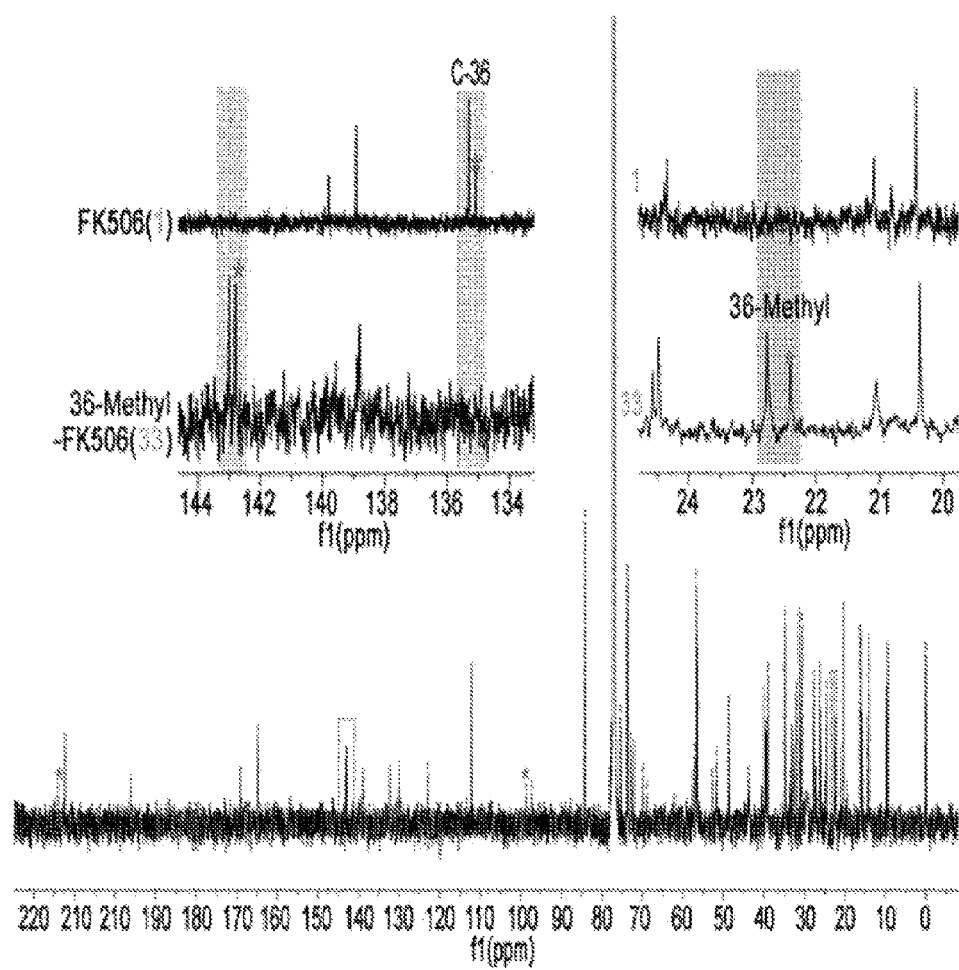
FIG. 11 shows $^{13}$C NMR (225 MHz, CDCl$_3$) spectrum of 36-methyl-FK506, in which '*' indicates the coexistence of tautomer (1, FK506; 33, 36-methyl-FK506)
Figure 12:
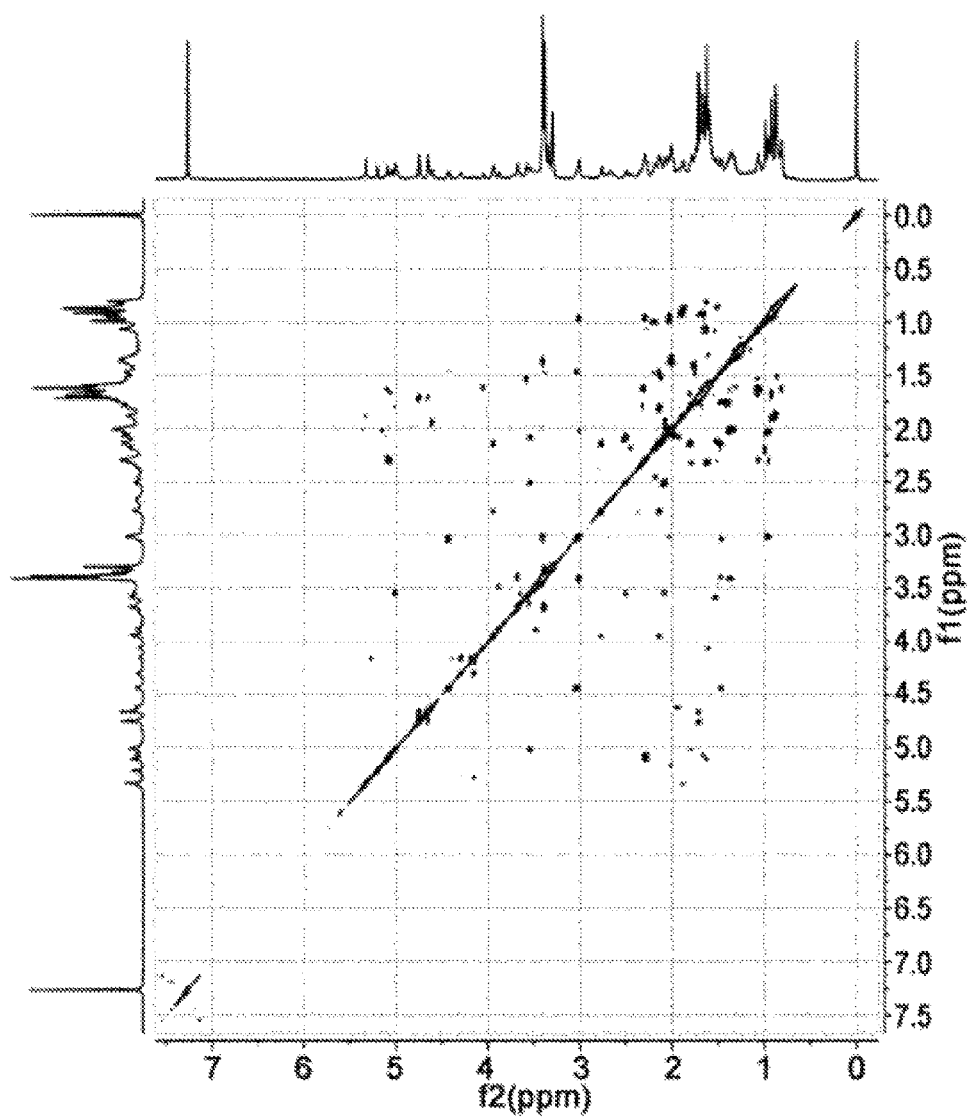
FIG. 12 shows 2D $^1$H-$^1$H COSY NMR spectrum of 36-methyl-FK506.
Figure 13:
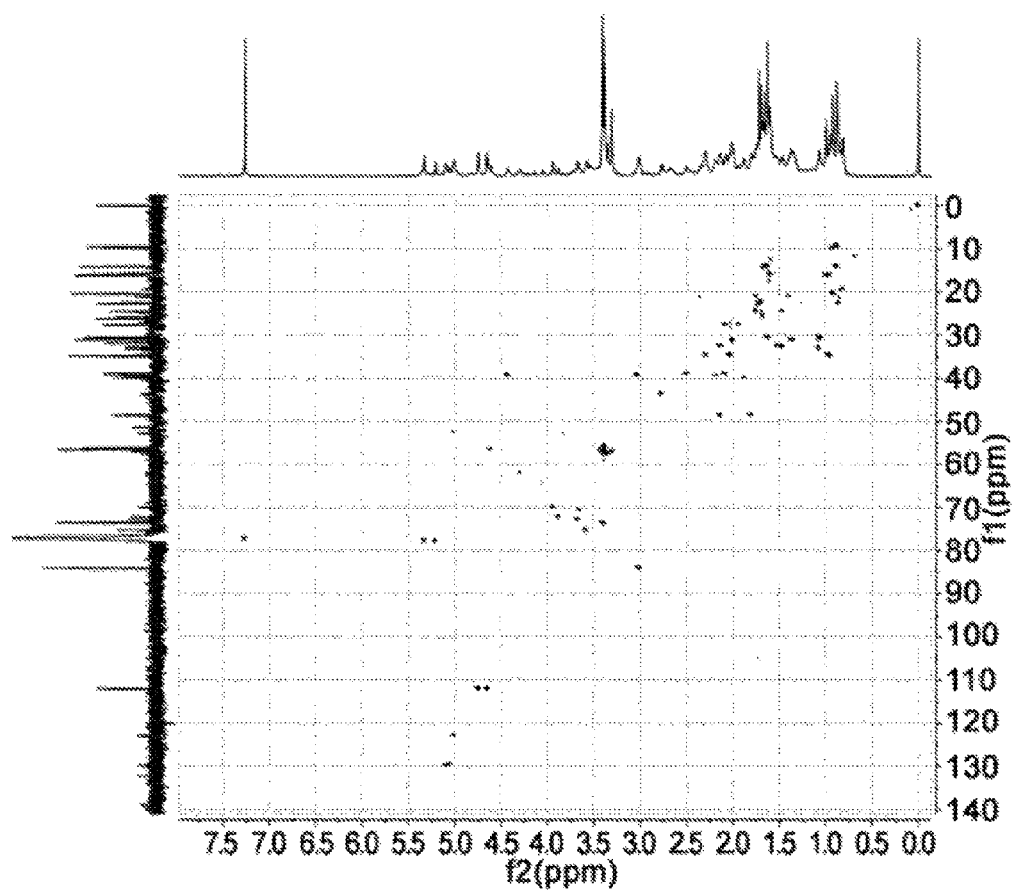
FIG. 13 shows 2D HMQC NMR spectrum of 36-methyl-FK506.
Figure 14:
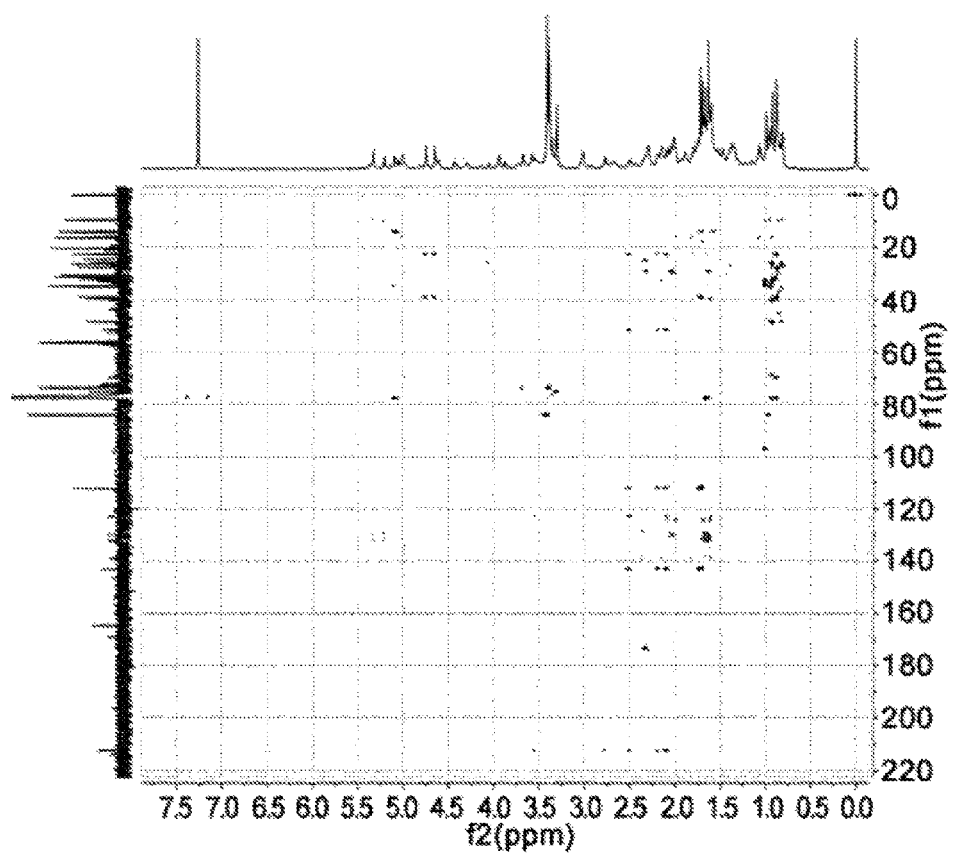
FIG. 14 shows 2D HMBC NMR spectrum of 36-methyl-FK506.
Figure 16A:
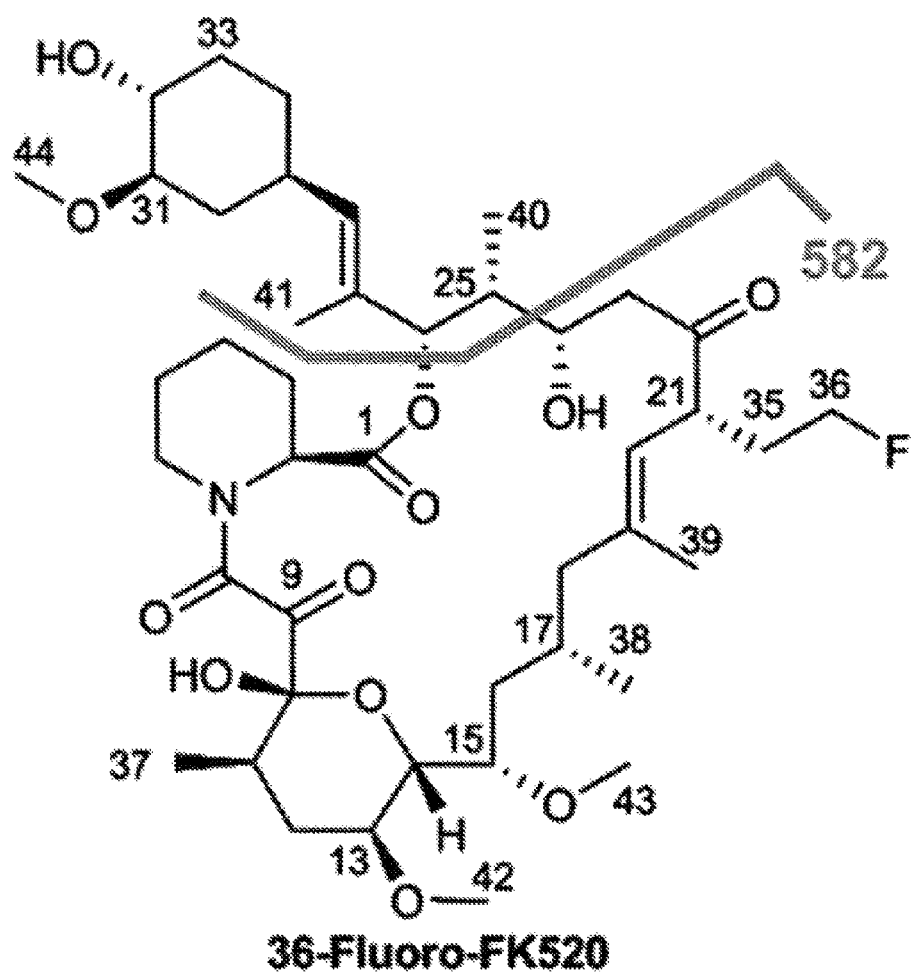
FIG. 16 shows ESI-MS/MS analysis of a novel FK506 analogue, 36-fluoro-FK520 obtained from the tcsB deletion mutant of Streptomyces sp. KCTC 11604BP (ΔtcsB strain) supplemented with 4-fluorocrotonic acid, in which (A) ESI-MS/MS fragmentation pattern of 36-fluoro-FK520, and (B) MS/MS spectra of 36-fluoro-FK520.
Figure 16B:
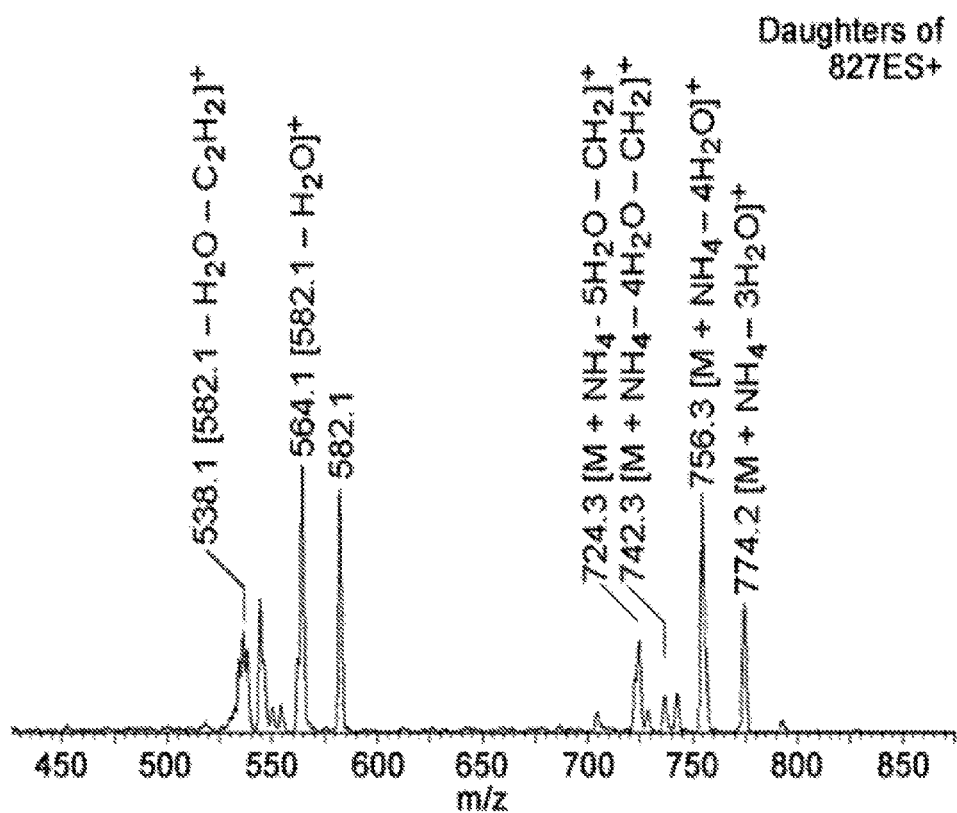
Figure 17:
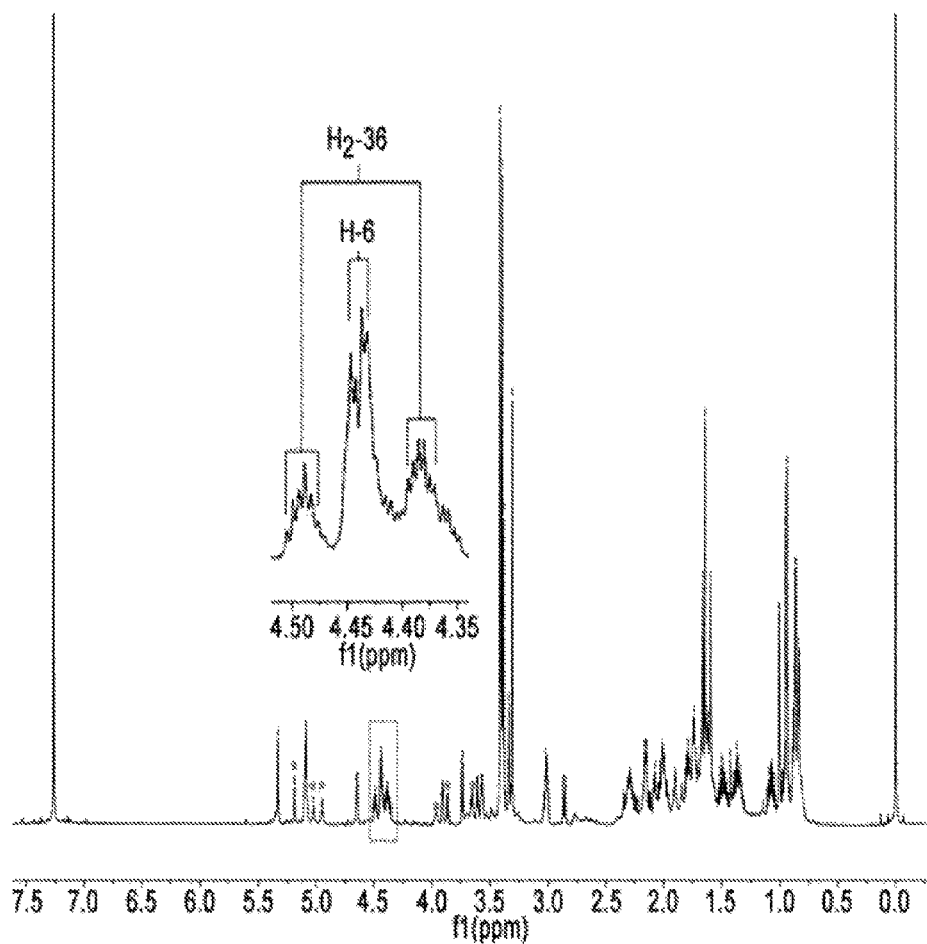
FIG. 17 shows $^1$H NMR (900 MHz, CDCl$_3$) spectrum of 36-fluoro-FK520, in which '*' indicates the coexistence of a tautomer.
Figure 18:
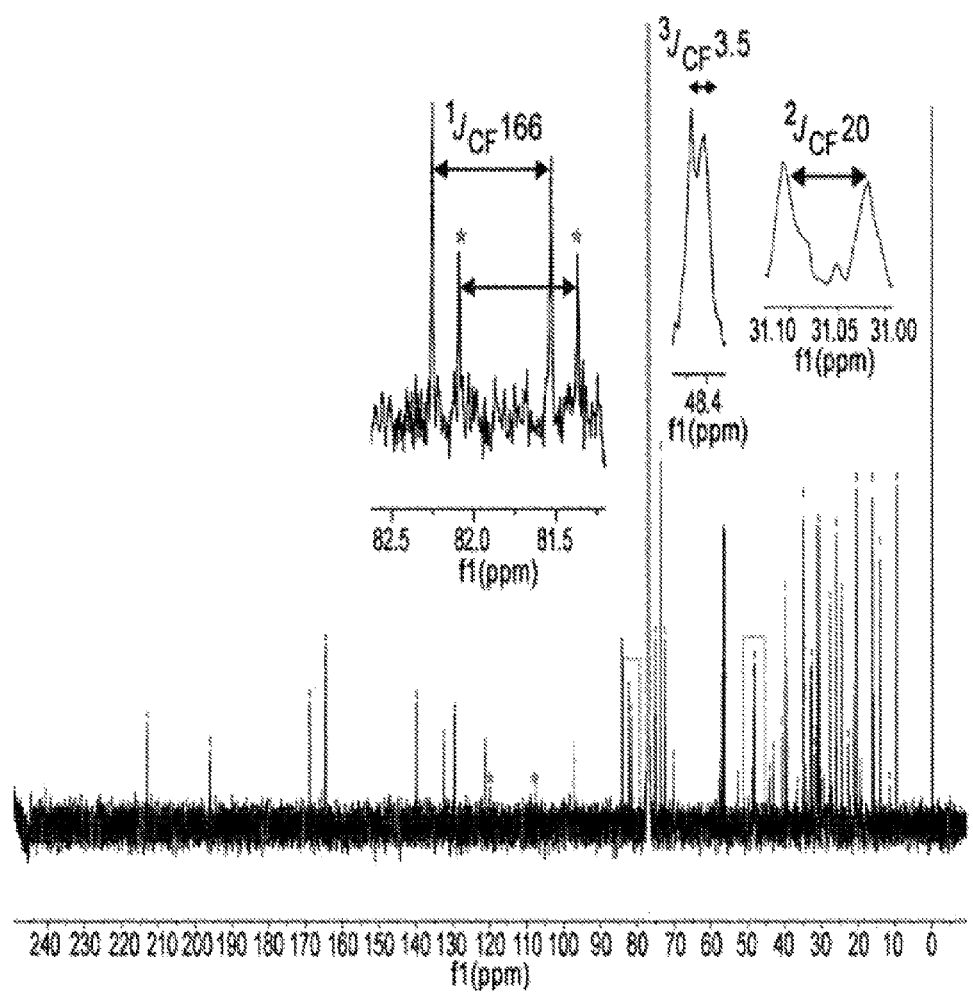
FIG. 18 shows $^{13}$C NMR (225 MHz, CDCl$_3$) spectrum of 36-fluoro-FK520, in which '*' indicates the coexistence of a tautomer.
Figure 19:
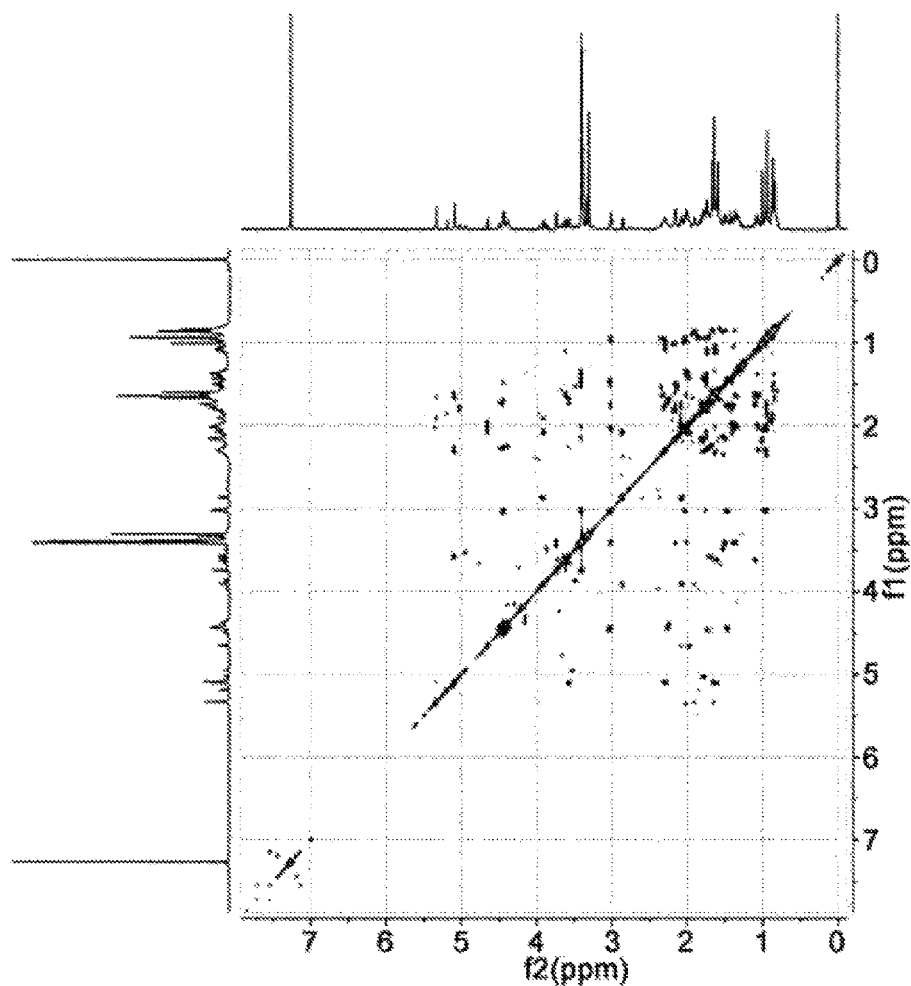
FIG. 19 shows 2D $^1$H-$^1$H COSY NMR spectrum of 36-fluoro-FK520.
Figure 20:
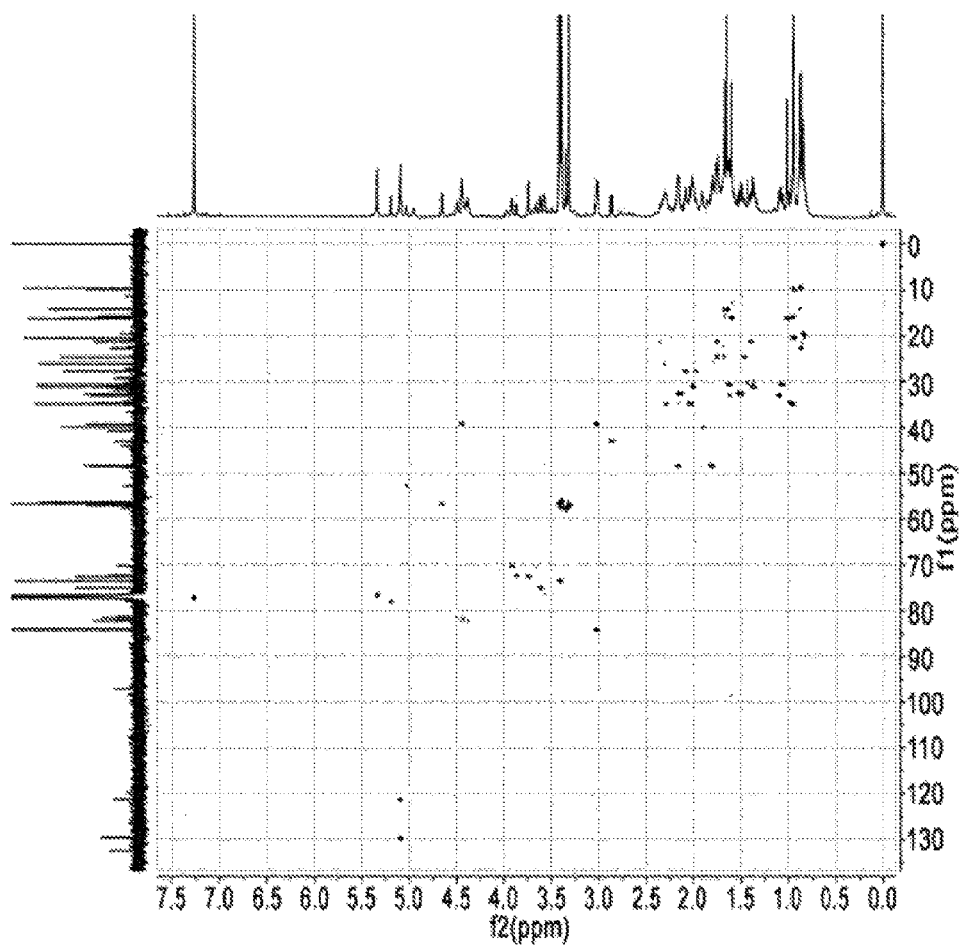
FIG. 20 shows 2D HMQC NMR spectrum of 36-fluoro-FK520.
Figure 21:
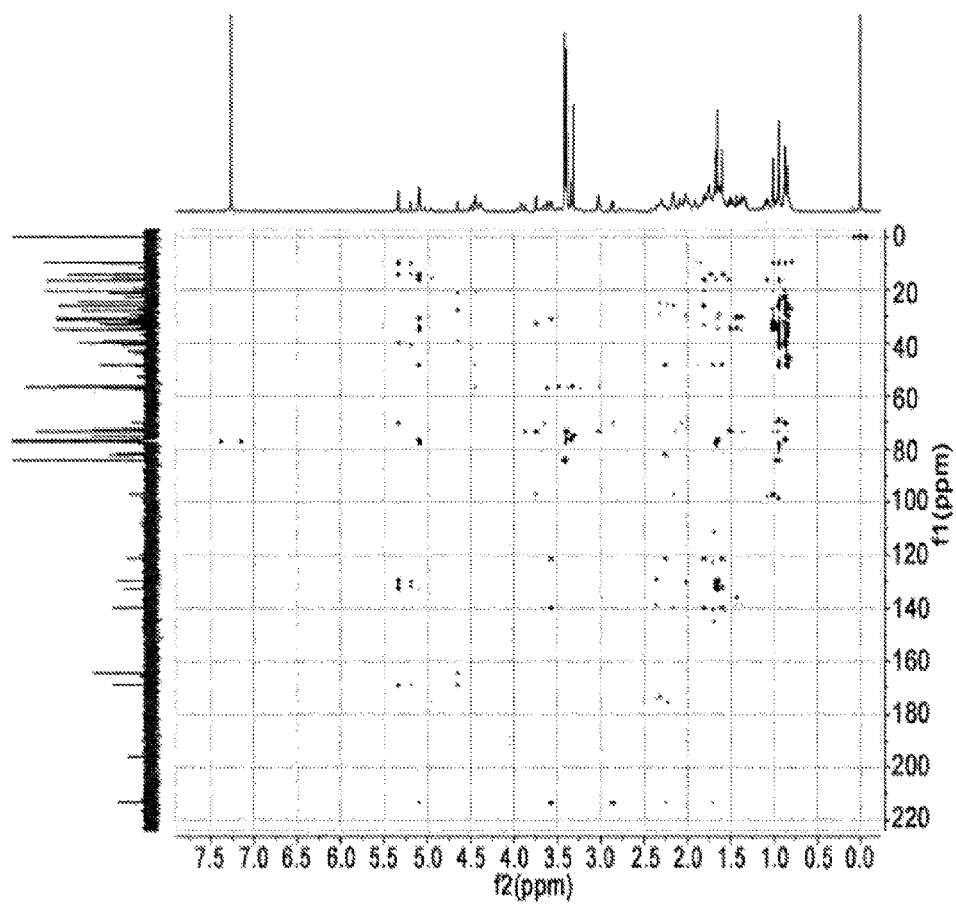
FIG. 21 shows 2D HMBC NMR spectrum of 36-fluoro-FK520.
Figure 22:
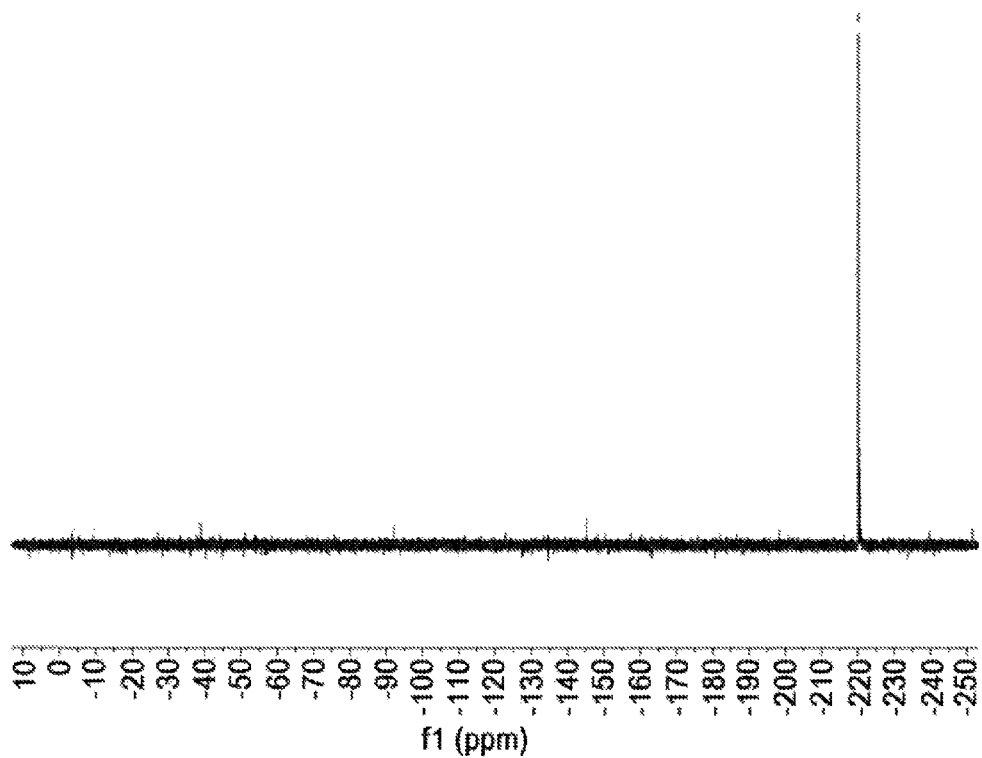
FIG. 22 shows 19F NMR spectrum of 36-fluoro-FK520.

The relative nerve regeneration activities of the mutasynthetic analogues, 36-methyl-FK506 and 36-fluoro-FK520, compared with authentic K506 and FK520, were determined using human neuroblastoma cells. The human neuroblastoma SH-SY5Y cells were cultured and treated with nerve growth factor (NGF; KOMA Biotech; 10 ng/ml) to induce neurite outgrowth in the presence or absence of 1 nM FK506, FK520, 6-methyl-FK506 and 36-fluoro-FK520. The cells (n=90) were randomly photographed after 96 hr of cultivation, then the number of cells with outgrowth was counted. The neurite lengths were measured on photographic prints. Duplicate wells were run in all experiments, and the entire experiment was replicated three times. Neurite length estimated from samples treated with NGF alone was used as a control (FIGS. 7 and 8).

Analysis of Binding of FKBP12-36-Methyl-FK506/36-Fluoro-FK52 Complexes to Calcineurin In silico docking experiments were conducted to probe the binding of the FKBP12-36-methyl-FK506/36-fluoro-FK520 complexes to calcineurin in comparison to FK506 and FK520. The binding free energy of the FKBP12-36-methyl-FK506-calcineurin complex (~7.78 Kcal/mol) is smaller than that of FKBP12-FK506-calcineurin (~6.42 Kcal/mol) (FIG. 24), suggesting that the relatively stronger interaction of the FKBP12-36-methyl-FK506-complex with calcineurin may lead to higher immunosuppressive activity. In contrast, the binding free energy between FKBP12-36-fluoro-FK520 and calcineurin was relatively higher at −5.82 Kcal/mol. 36-methyl-FK506 had a ~20% greater effect on neurite outgrowth in cultures of the human neuroblastoma cell line SH-SY5Y treated with nerve growth factor compared with FK506 (FIGS. 7 and 8).

The above results demonstrate that the novel tacrolimus analogues of the present invention, i.e. 36-methyl-FK506 and 36-fluoro-FK520, but especially 36-methyl-FK506, have the strong neurite outgrowth activity, suggesting that the composition comprising the above analogues can be used for promoting neurite outgrowth, furthermore for the prevention or treatment of the neurological diseases.

Statistical Analysis

For statistical comparisons of group differences, especially for both the T cell activation and neurite outgrowth assays, quantitative data were analyzed by one-way analysis of variance (ANOVA) followed by Fisher's t-test according to the statistical program SigmaStat® (Jandel Scientific; version 3.1).

INDUSTRIAL APPLICABILITY

The tacrolimus analogues, which are excellent in neuroprotective and immunosuppressive effects, can be efficiently produced by using the method for producing tacrolimus analogues of the present invention. The novel tacrolimus analogues, which are more excellent in neuroprotective and immunosuppressive effects than the known tacrolimus, can be used for the treatment of neurological diseases and immune hypersensitivity disorders.

What is claimed is:

1. A method for preparing a tacrolimus analogue which is substituted at position C21 of tacrolimus (Formula A), comprising:
   (a) culturing an isolated modified *Streptomyces* sp. strain in which the activity of one or more enzymes selected from the group consisting of endogenous TcsA, TcsB, TcsC and TcsD is reduced; and
   (b) feeding carboxylic acids to the strain,

[Formula A]

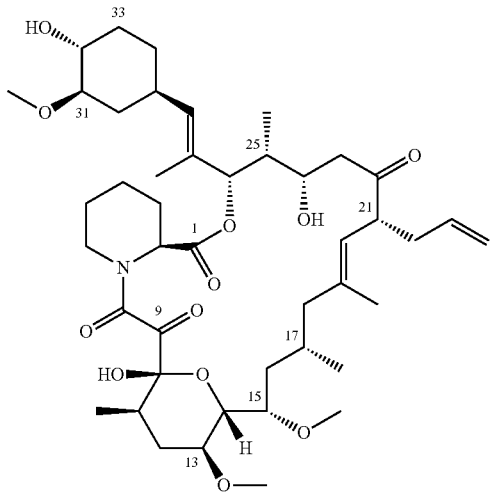

wherein the carboxylic acid is incorporated as an extender unit of C21 ally side chain of tacrolimus;

the carboxylic acid in step (b) is trans-2-hexenoic acid or 4-methylpentanoic acid; and the tacrolimus analogue is 36,37-dihydro-37-methyl-FK506 or 36-methyl-FK506.

2. The method according to claim 1, whereby the tacrolimus analogue is produced having an immunosuppressive effect, neuroprotective effect, or neuroprotective and immunosuppressive effects, wherein the effects are accomplished by administering a composition comprising tacrolimus analogue to a subject in need thereof in a therapeutically or prophylactically effective amount.

3. The method according to claim 1, wherein the activity of endogenous TcsA is reduced.

4. The method according to claim 1, wherein the activity of endogenous TcsB is reduced.

5. The method according to claim 1, wherein the activity of endogenous TcsC is reduced.

6. The method according to claim 1, wherein the activity of endogenous TcsD is reduced.

7. The method according to claim 1, wherein the carboxylic acid in step (b) is trans-2-hexenoic acid.

8. The method according to claim 1, wherein the carboxylic acid in step (b) is 4-methylpentanoic acid.

9. The method according to claim 1, wherein the tacrolimus analogue is 36,37-dihydro-37-methyl-FK506.

10. The method according to claim 1, wherein the tacrolimus analogue is 36-methyl-FK506.

11. The method according to claim 1, wherein the carboxylic acid in step (b) is trans-2-hexenoic acid and the tacrolimus analogue is 36,37-dihydro-37-methyl-FK506.

12. The method according to claim 1, wherein the carboxylic acid in step (b) is 4-methylpentanoic acid and the tacrolimus analogue is 36-methyl-FK506.

* * * * *